(12) United States Patent
Harshman et al.

(10) Patent No.: US 9,532,823 B2
(45) Date of Patent: Jan. 3, 2017

(54) MANIFOLD FOR FILLING PLURAL CANNULAE, THE MANIFOLD INCLUDING A QUICK RELEASE MECHANISM FOR SIMULTANEOUSLY HOLDING AND RELEASING THE CANNULAE TO/FROM THE MANIFOLD

(71) Applicant: Stryker Corporation, Kalamazoo, MI (US)

(72) Inventors: Gabriel J. Harshman, Kalamazoo, MI (US); David R. Boboltz, Kalamazoo, MI (US); Ross D. Thelen, Vicksburg, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 237 days.

(21) Appl. No.: 14/156,853

(22) Filed: Jan. 16, 2014

(65) Prior Publication Data

US 2014/0130937 A1    May 15, 2014

Related U.S. Application Data

(63) Continuation of application No. PCT/US2012/047462, filed on Jul. 19, 2012.
(Continued)

(51) Int. Cl.
*A61B 17/88* (2006.01)
*B01F 11/00* (2006.01)
(Continued)

(52) U.S. Cl.
CPC ....... *A61B 17/8833* (2013.01); *B01F 11/0082* (2013.01); *B01F 13/0023* (2013.01);
(Continued)

(58) Field of Classification Search
CPC .............. B01F 11/0082; B01F 13/0023; B01F 15/00506; B01F 15/0279; B01F 2215/0029; A61B 2017/8838
See application file for complete search history.

(56) References Cited

U.S. PATENT DOCUMENTS 3,470,893 A * 10/1969 Nelson .................. B60K 25/04
                                                              137/351
5,190,525 A *  3/1993 Oswald ................. A61M 39/02
                                                              604/83
(Continued)

FOREIGN PATENT DOCUMENTS

GB          2 042 137 A      9/1980
WO         02/34378 A2      5/2002
(Continued)

OTHER PUBLICATIONS

PCT "International Search Report and Written Opinion" for PCT/US2012/047462, dated Oct. 23, 2012.

*Primary Examiner* — Tony G Soohoo

(57) ABSTRACT

A system for loading plural cannulae with a substance that is to be injected into living tissue. This invention provides an efficient means of providing plural substance-filled cannulae for surgical procedures, such as vertebral augmentations. The system includes a mixing and delivery system, including a manifold. The manifold includes a housing with a plurality of channels that route the flow of the mixed substance from a single central channel to multiple sub-channels for the simultaneous filling of attached cannulae. The manifold also includes valves that regulate the flow of the substance out of the manifold. The open/closed states of these valves are inherently set as a function of the presence/absence of cannulae. A cartridge/plate releasably holds the multiple cannulae to the manifold. The release of the car-
(Continued)

tridge/plate results in the simultaneous release of the substance-filled cannulae from the manifold.

21 Claims, 56 Drawing Sheets

Related U.S. Application Data

(60) Provisional application No. 61/549,091, filed on Oct. 19, 2011, provisional application No. 61/510,022, filed on Jul. 20, 2011.

(51) Int. Cl.
    *B01F 13/00*      (2006.01)
    *B01F 15/00*      (2006.01)
    *B01F 15/02*      (2006.01)

(52) U.S. Cl.
    CPC .... *B01F 15/00506* (2013.01); *B01F 15/0279* (2013.01); *A61B 2017/8838* (2013.01); *B01F 2215/0029* (2013.01)

(56) References Cited

U.S. PATENT DOCUMENTS

| | | | | |
|---|---|---|---|---|
| 5,192,269 A | * | 3/1993 | Poli | A61M 5/1408 137/606 |
| 5,232,024 A | * | 8/1993 | Williams | A61M 39/223 137/606 |
| 5,304,165 A | * | 4/1994 | Haber | A61J 1/2089 604/411 |
| 5,423,791 A | | 6/1995 | Bartlett | |
| 5,431,185 A | * | 7/1995 | Shannon | A61M 39/04 137/512.4 |
| 5,674,394 A | * | 10/1997 | Whitmore | A61M 1/3496 210/321.6 |
| 5,695,478 A | * | 12/1997 | Haindl | A61M 5/1408 128/DIG. 12 |
| 5,738,662 A | * | 4/1998 | Shannon | A61M 5/1408 137/606 |
| 6,171,287 B1 | * | 1/2001 | Lynn | A61M 39/02 251/149 |
| 6,398,765 B1 | * | 6/2002 | Hung | A61B 10/0045 604/284 |
| 6,547,432 B2 | | 4/2003 | Coffeen et al. | |
| 7,175,336 B2 | * | 2/2007 | Voellmicke | A61F 2/4644 366/160.4 |
| 7,658,537 B2 | | 2/2010 | Coffeen et al. | |
| 8,308,340 B2 | * | 11/2012 | Ferrante | A61B 17/00491 222/137 |
| 2002/0193752 A1 | * | 12/2002 | Lynn | A61M 39/02 604/249 |
| 2004/0016475 A1 | | 1/2004 | Navaro | |
| 2006/0095017 A1 | * | 5/2006 | Hung | A61B 10/0045 604/514 |
| 2007/0225635 A1 | * | 9/2007 | Lynn | A61M 39/045 604/30 |
| 2008/0243129 A1 | * | 10/2008 | Steffen | A61B 17/8822 606/93 |
| 2009/0137951 A1 | * | 5/2009 | Buisson | A61M 5/1408 604/87 |

FOREIGN PATENT DOCUMENTS

| | | |
|---|---|---|
| WO | 2004/096113 A2 | 11/2004 |
| WO | 2005/123162 A1 | 12/2005 |
| WO | 2007/122006 A1 | 11/2007 |

* cited by examiner

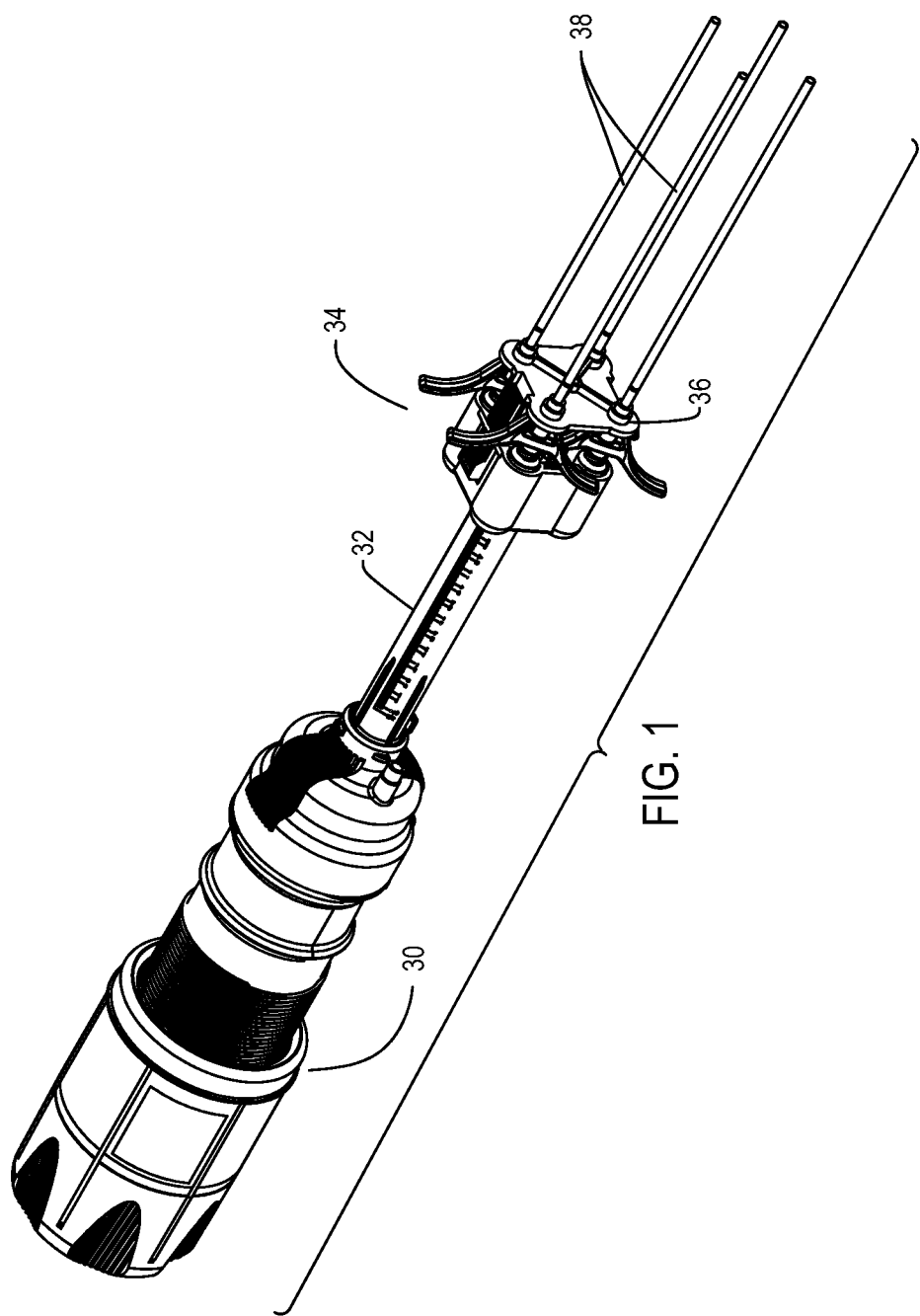

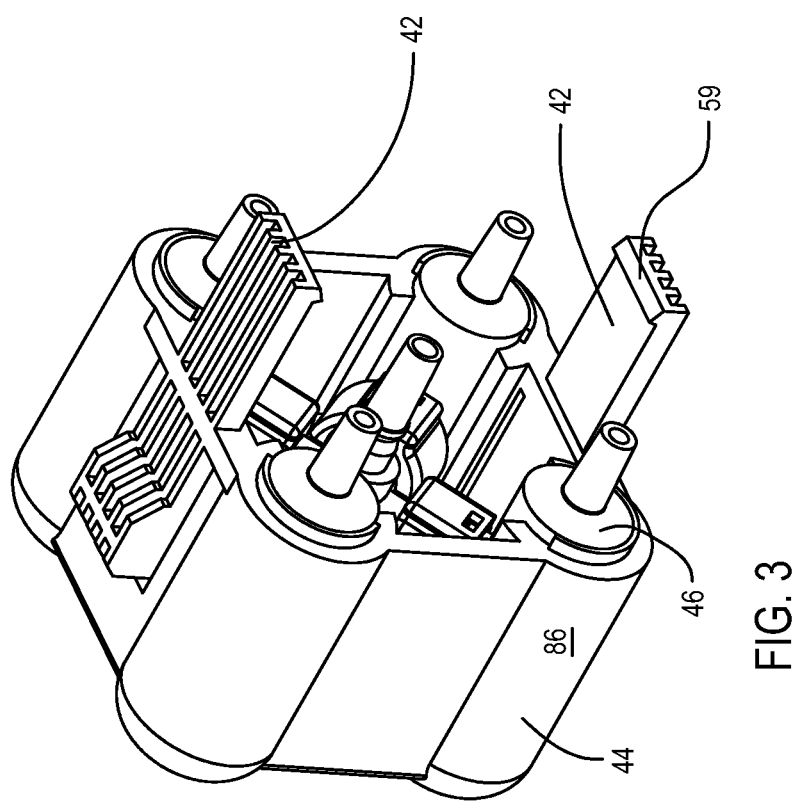

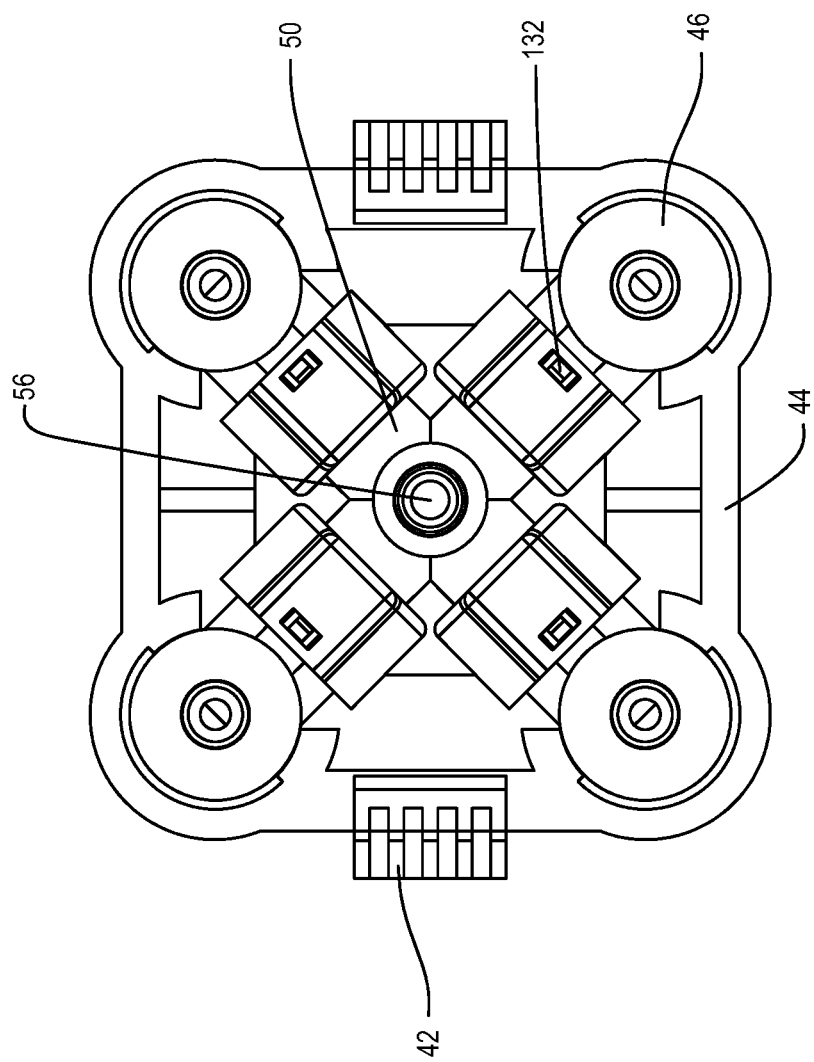

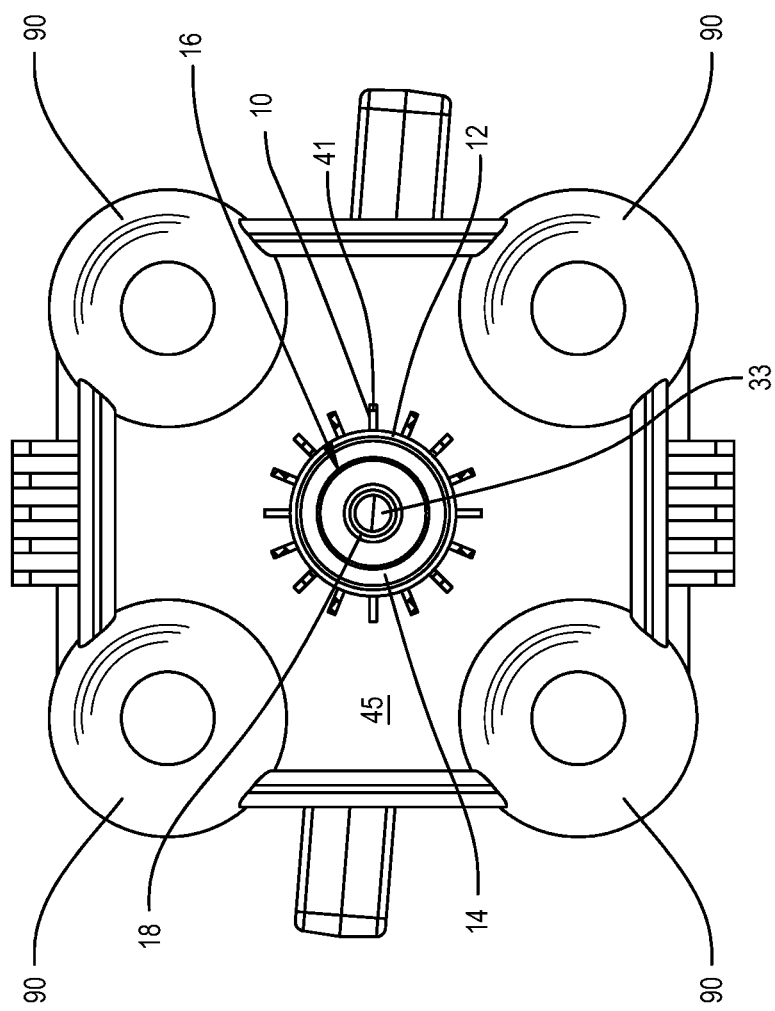

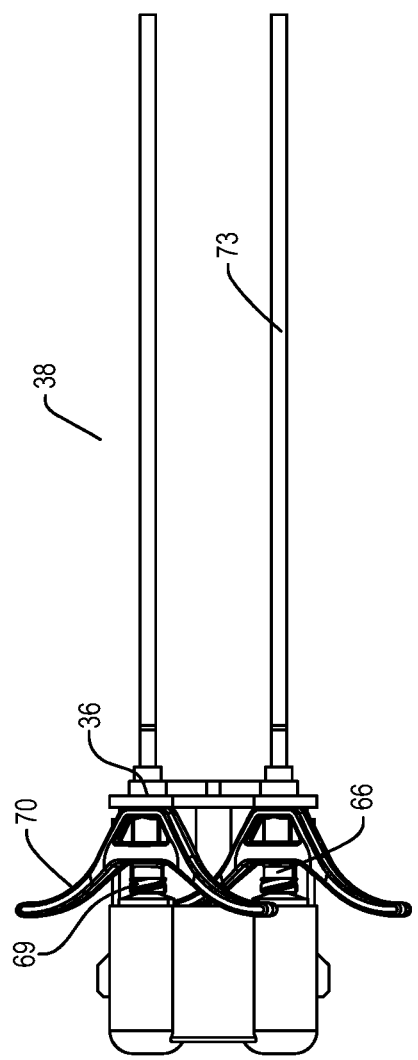

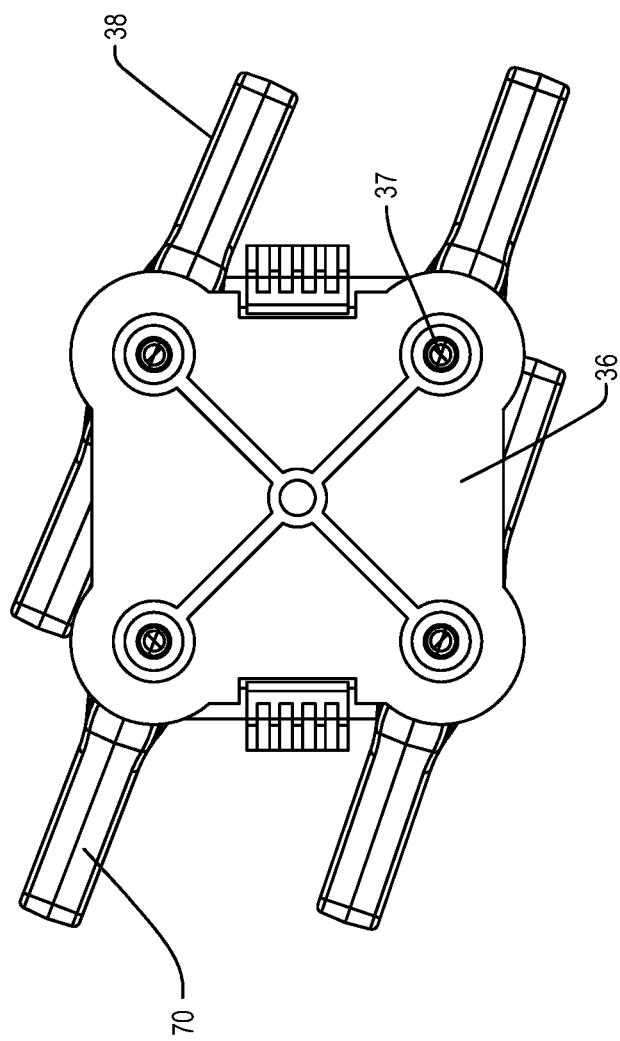

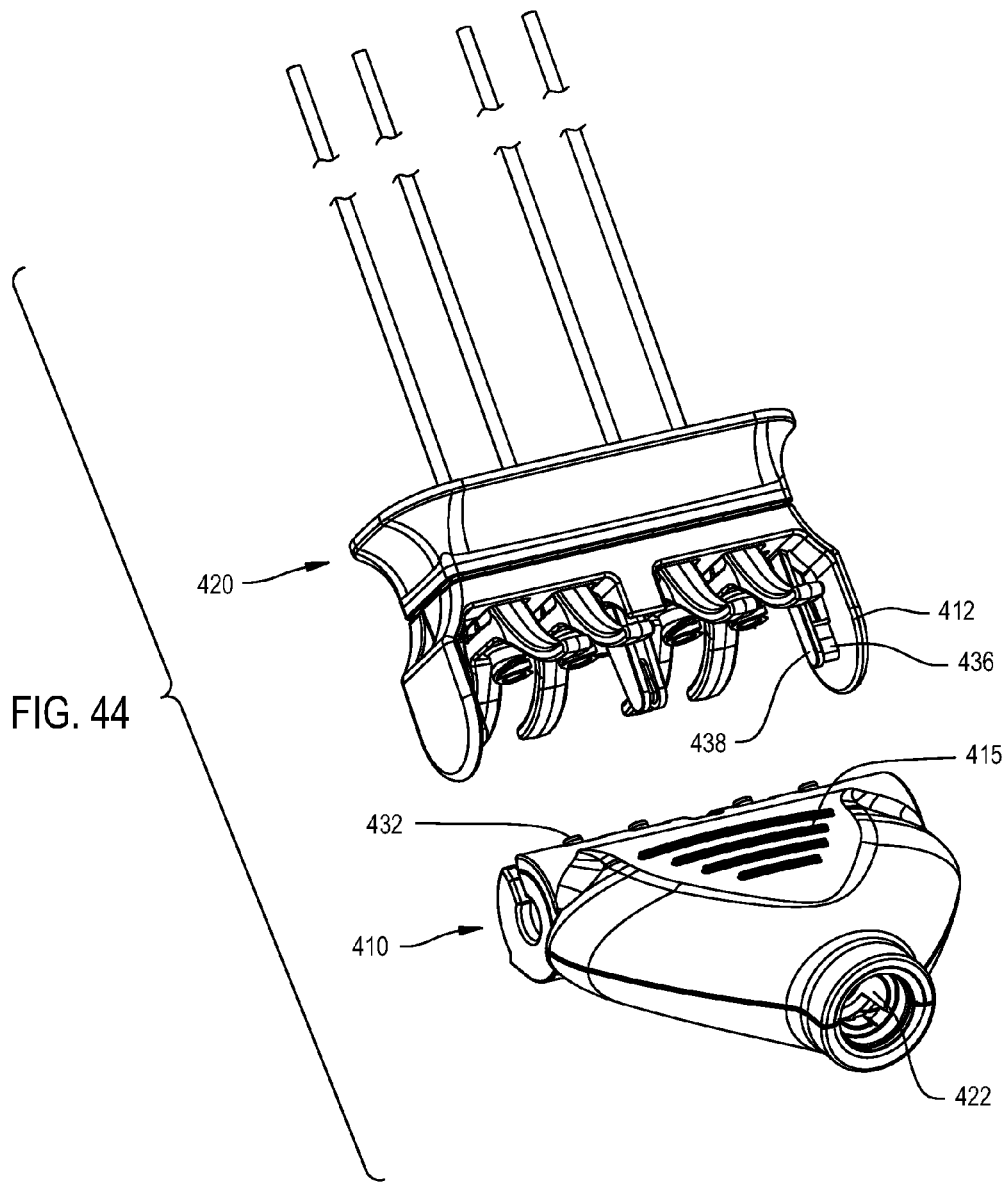

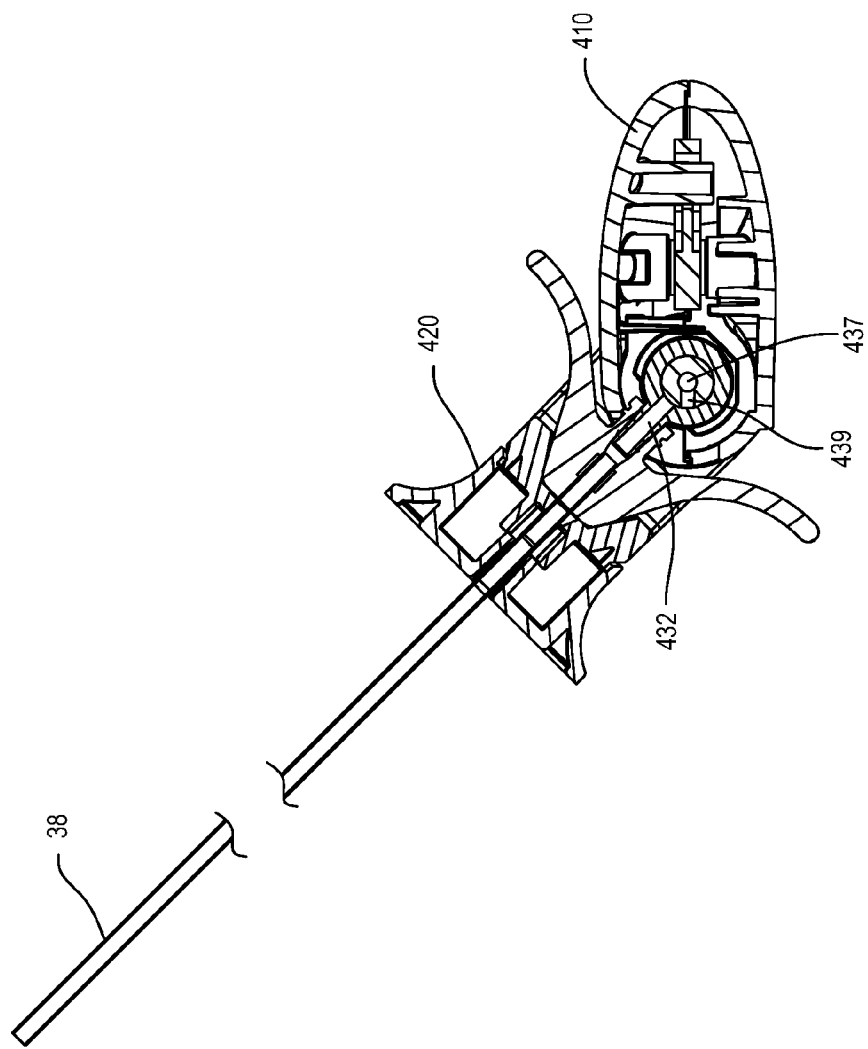

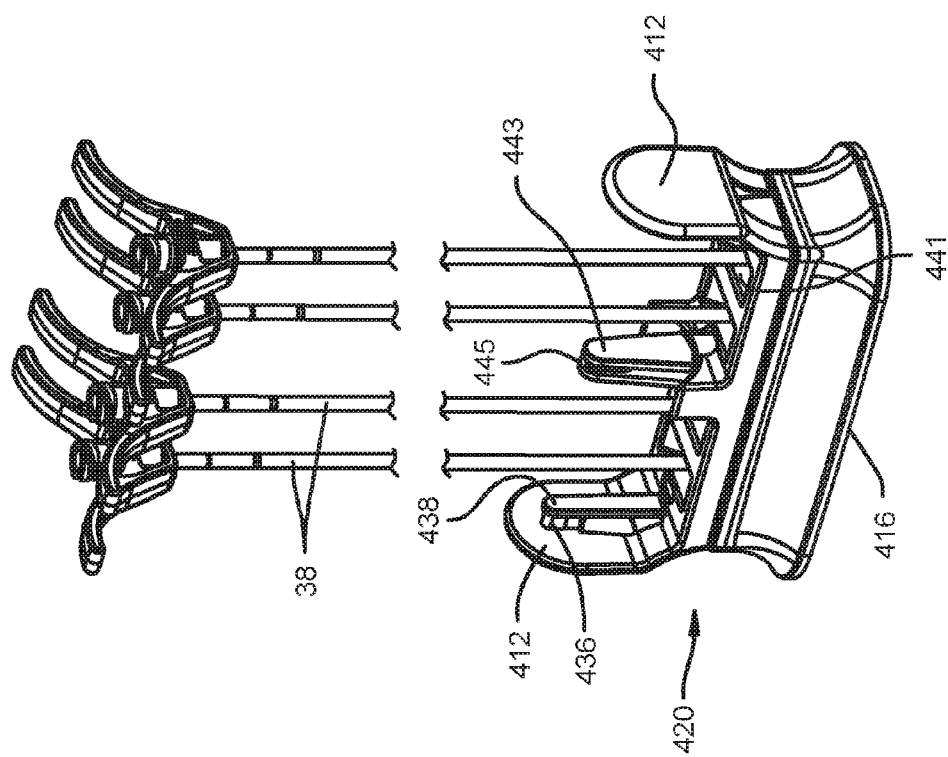

MANIFOLD FOR FILLING PLURAL CANNULAE, THE MANIFOLD INCLUDING A QUICK RELEASE MECHANISM FOR SIMULTANEOUSLY HOLDING AND RELEASING THE CANNULAE TO/FROM THE MANIFOLD

RELATIONSHIP TO EARLIER FILED APPLICATIONS

This application is a continuation of PCT Pat. App. No. PCT/US2012/047462 filed 19 Jul. 2011. PCT Pat. App. No. PCT/US2012/047462 is a non provisional application that claims priority from both U.S. Provisional Pat. App. No. 61/510,022 filed 20 Jul. 2011 and No. 61/549,091 filed 19 Oct. 2011. The contents of the above-identified priority applications are explicitly incorporated herein by reference.

FIELD OF THE INVENTION

The present invention is generally related to bone cement mixing and delivery systems. More particularly, the system of this invention is able to, after the cement is mixed, simultaneously fill plural bone cement cannulae.

BACKGROUND OF THE INVENTION

Bone cement mixing and delivery systems are well known for mixing separate components of bone cement together to form a uniform bone cement mixture and then delivering that mixture to a target site. Typically, such systems employ a mixer having a handle for manually mixing the components. Once mixed, the mixture is then transferred to a delivery device such as a syringe or cannula. A cement cannula is a type of syringe with a large length to diameter ratio. This ratio provides a user with a large mechanical advantage and good tactile feedback. Physicians fill cannulae with bone cement. These cannulae are filled prior to delivering said cement to the target site of a body.

The syringe or cannula is used to inject the bone cement mixture into the target site. The target site may be an anatomical site such as a vertebral body or the target site may be in or near an implant. Examples of target sites include medullary canals for total hip arthroplasty procedures, vertebral bodies for vertebroplasty or kyphoplasty procedures, and other sites in which bone cement is required.

Often, bone cements used in these procedures have working times of 20 minutes or less before the cement begins to harden. Once the cement starts to harden, it is difficult, if not impossible, for the practitioner to continue to use the cement. Current systems require a great deal of user interaction in set-up, including mixing the bone cement components and manually transferring the cement to the delivery device. This allows for only a small amount of working time. Current delivery devices are available, as previously mentioned, in the form of a syringe or cannula, and each delivery device must be filled with bone cement before use.

There are a number of different medical procedures wherein prior to the start of the procedure, it is useful to have a number of cannulae prefilled with cement. One such procedure is a vertebral augmentation procedure, which includes kyphoplasty and vertebroplasty, where cannulae are preloaded with cement. Each cement filled cannula is, one at a time, placed in an access cannula. A plunger forces the cement into the target bone. In a vertebral augmentation procedure, it may be necessary to inject the cement from multiple cannulae into the patient. Accordingly often, prior to the start of most procedures, at least four cannulae are preloaded with cement.

A number of bone cement mixing and transfer systems allow cannulae to be filled only one at a time. In the event multiple cannulae prefilled with cement are required for a procedure, the person responsible for filling the cannulae must work quickly to pre-fill the cannulae in order not to delay the surgical procedure.

In the prior art, currently there exists a delivery system which provides for the filling of bone cement within multiple syringes. In this system, multiple syringes are sequentially spaced apart and are attached perpendicularly to a distal end of a delivery device. Each syringe is equipped with a valve. Once cement has filled the entire reservoir of a first syringe, the user turns the valve into the "OFF" position. Once in the "OFF" position, cement can no longer flow to the syringe. The cement is then able to fill a next syringe in the sequence. Once all syringes are filled, one at a time, syringes are then removed from the mixer.

While the above system offers some benefits over a single fill cement mixing and delivery system, it is not without its own disadvantages. The system does not simultaneously fill the syringes. The user is required to set the on/off states of the individual valves. Having to set these valves can add to the time it takes to fill the cannulae. Moreover, having to set these valves introduces the possibility of human error into the cannula filling process.

SUMMARY OF THE INVENTION

This invention is related to a new and useful system for loading substances that are to be injected into living tissue into plural cannulae. One such substance is bone cement. It is a further feature of this invention to provide a quick release of the substance filled cannulae from the rest of the system. Owing to the quick drying time of bone cement during surgical procedures, this invention provides an efficient means of providing plural cement filled cannulae for surgical procedures, such as vertebral augmentations.

The bone cement mixing and delivery device of this invention includes a cement mixing and delivery system including: a mixer housing, a mixing paddle for mixing the bone cement components, a plunger to push mixed bone cement through the mixer housing, and a manifold. The manifold includes a housing with a plurality of channels that route the flow of bone cement from a single central channel to multiple sub-channels for the simultaneous filling into attached cement cannulae. The manifold also includes valve assemblies that regulate the flow of bone cement out of the manifold. The open/closed states of these valves are inherently set as a function of the presence/absence of cannulae. A plate releasably holds the multiple cannulae to the manifold. The release of the plate results in the simultaneous release of the cement filled cannulae from the manifold.

In one embodiment of the present invention, the manifold of this system is able to fill plural cement cannulae ranging from two to four with bone cement. Bone cement travels through a central channel, whereby flow is then diverted into five sub-channels. Depending on the number of cannulae present and the presence of the plate, each sub-channel is active for cement filling. A sub-channel is only active if a cannula is present. The user may select anywhere from two to four plural cement cannulae for simultaneous filling. This is called selective, plural filling mode for simultaneous cannulae. When the plate is removed after a first fill, only the sub-channel extending longitudinally from the central channel is active, and the user then may fill one cannula at a time. This is called single fill mode where only one cement cannula is able to be filled.

In a second embodiment, the manifold of this invention is capable of simultaneously filling plural cement by flow to divert from a central channel to a series of multiple sub-channels, which then enter plural cannulae. Multiple cannulae are then simultaneously released using a gear assembly to rotate a two-cap system, which then unwinds cannulae from the manifold allowing for a simultaneous release.

BRIEF DESCRIPTION OF THE DRAWINGS

The invention is pointed out with particularity in the claims. The above and further features of this invention may be better understood by reference to the following description taken in conjunction with the accompanying drawings in which:

FIG. 1 is a perspective view of a first embodiment of a cement mixing and delivery system, which includes a mixing device, a delivery tube, and a manifold with plural cement cannulae;

FIG. 3 is a perspective view of the manifold housing, including a block secured within the housing, and a plurality of valve assemblies;

FIG. 4 is a plan view of the distal face of the manifold, without cement cannulae, illustrating the block, a central channel, a plurality of sockets attached to the block, and a plurality of valve assemblies secured to the block and within the manifold housing;

FIG. 4A is a plan view of the proximal face of the manifold illustrating a Luer fitting, a rim, a molded-in snap feature, a cylindrical boss, and a manifold inlet opening;

FIG. 6 is a plan view of the manifold in a plural fill mode with plural cement cannulae attached;

FIG. 7 is a plan view of the distal end of the manifold illustrating the plate, and further showing the orientation of four loaded cannulae;

FIG. 44 is an exploded perspective view of an alternative embodiment of the manifold;

FIG. 45 is a cross-sectional view of an alternative embodiment of the manifold;

FIG. 48 is a perspective view of an alternative embodiment of the manifold.

DETAILED DESCRIPTION OF THE INVENTION

I. First Embodiment

For the purpose of promoting and understanding the present invention, references are made in the text hereof to exemplary embodiments of a bone cement mixing and delivery device, with a manifold for simultaneously filling plural cement cannulae, only some of which are depicted in the figures. It should nevertheless be understood that no limitations on the scope of the invention are thereby intended. One of ordinary skill in the art will readily appreciate that modifications such as those involving the materials from which the components are made, the size of the components, functional equivalents of the elements, and the inclusion of additional elements do not depart from the spirit and scope of the present invention. Some of these possible modifications are discussed in the following description. Therefore, specific details disclosed herein are not to be interpreted as limiting, but rather as support for the claims and as a representative basis for teaching one skilled in the art to employ the present invention in virtually any appropriately detailed system, structure, or manner.

As used herein, "distal" refers to the end of the delivery device from which the bone cement mixture is discharged, and "proximal" refers to the end of the delivery device opposite the end from which the bone cement mixture is discharged and closest to the user. The terms "substantially" and "approximately," as used herein, may be applied to modify any quantitative representation that could permissibly vary without resulting in a change in the basic function to which it is related.

The terms "mixing," "transferring," and "delivery" are all three distinct stages generally found in most bone cement mixing and delivery systems. "Mixing," as used herein, is the process where separate bone cement-forming components are mixed together using a mixer to create bone cement. "Transferring," as used herein, is the process where mixed bone cement is transferred from a mixing chamber into a delivery tube for delivering the mixed bone cement. "Delivery," as used herein, is the final process where mixed cement exits from the cannula or other delivery device and enters the target site during the surgical procedure.

Figure 1A:
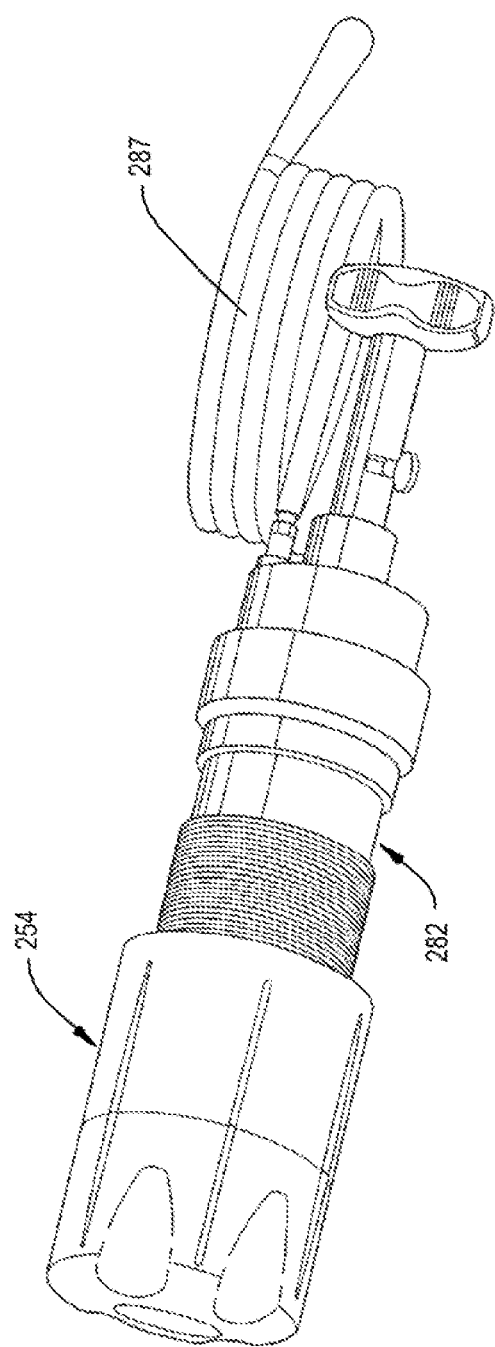
FIG. 1A is a perspective view of a first embodiment of a cement mixing and delivery system.
Figure 1B:
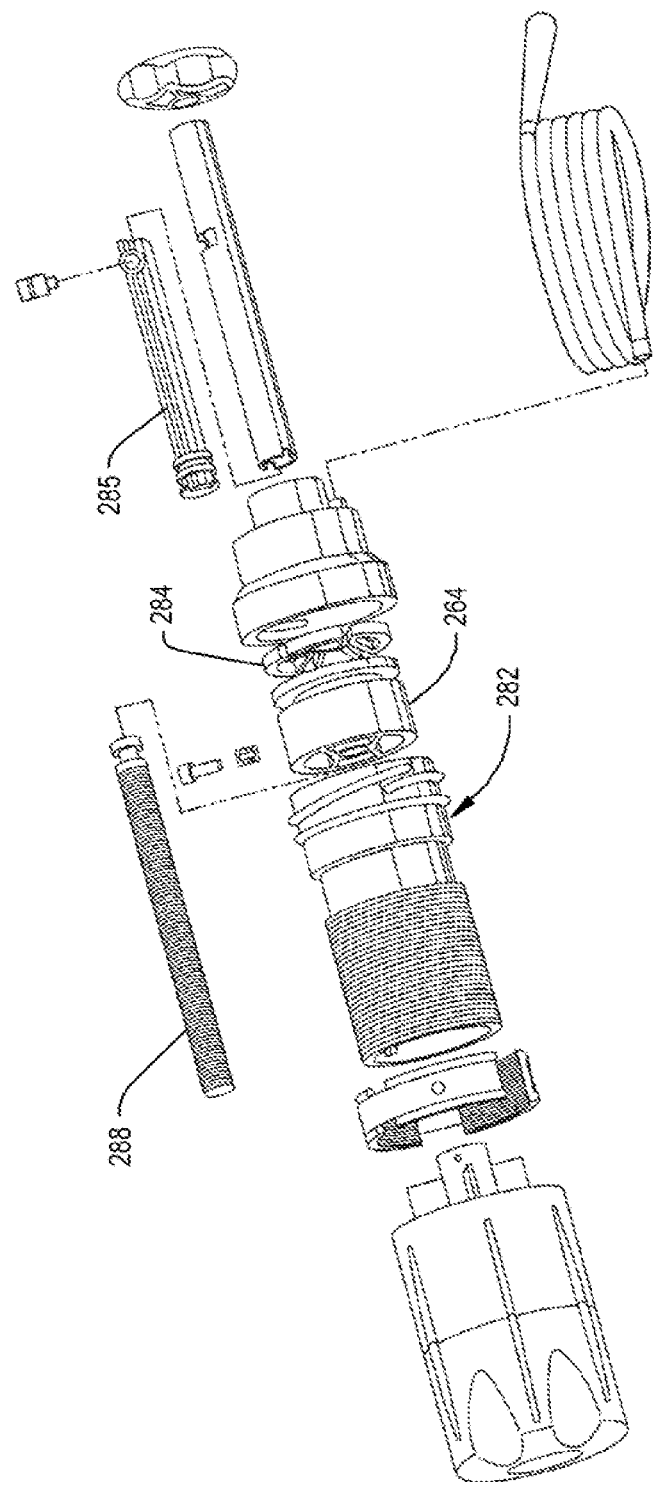
FIG. 1B is an exploded view of the embodiment of FIG. 1.
Figure 1C:
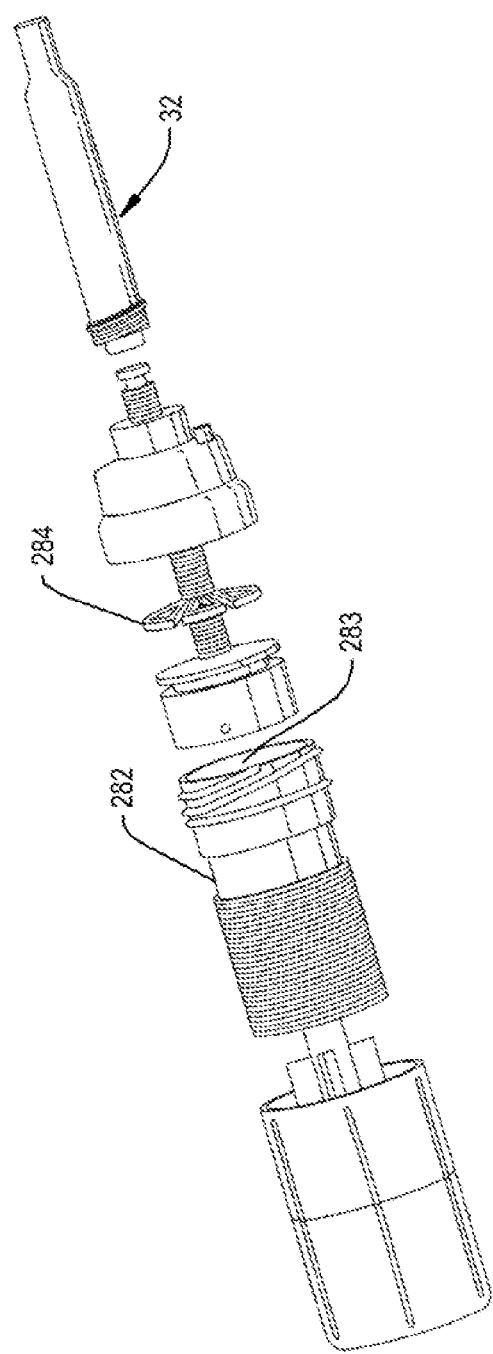
FIG. 1C is an exploded perspective view of the embodiment of FIG. 1 shown in a delivery phase.

Referring in more detail to the drawings, a bone cement mixing and delivery system of the present invention is generally shown at 30 in FIGS. 1, 1A, 1B, and 1C. Mixing system 30 is able to fill one or a plural set of cannulae 38. Mixing system 30 generally includes a mixer housing 282, a mixing paddle 284, and a plunger 288. The mixer housing 282 defines a chamber 283 for receiving the bone cement forming components. The mixer housing 282 has an outlet opening (not identified) into a tube 32, as shown in FIG. 1C. The mixing paddle 284 is disposed within the mixing chamber 283. Mixing paddle 284 is attached to a manually actuated shaft 285 that extends out of the housing. The actuation of the shaft 285 results in the like actuation of the paddle 284 in order to mix the bone cement forming components together. The piston 264 is moveably mounted to the housing 282 for movement through the mixing chamber 283. Piston 264 is displaced to move the mixed bone cement from the mixing chamber into tube 32. System 30 also includes plunger 288 that initially moves with piston 264. Plunger 288 operates like a second piston. As discussed below, plunger 288 is advanced beyond piston 264 to move the mixed cement out of the tube 32 into the cannulae 38 of a manifold 34, also part of this invention.

Mixing system 30 further includes a vacuum line 287 for attachment to vacuum pump (not illustrated and not part of the invention). The vacuum is drawn to remove gas from the chamber 283. The removal of the gas decreases the porosity and increases the strength of the bone cement.

A detailed discussion of the construction of housing 282, piston 264 and plunger 288 can be found in the Applicant's Assignee's U.S. Pat. No. 6,547,432, issued on Apr. 15, 2003, the contents of which are herein incorporated by reference.

In brief, manifold 34 includes channels 56, 58, 60, 62 and 64 that are in fluid communication with tube 32 to receive the mixed cement discharged from the chamber 283. A plate 36 is removably coupled to the distally directed front end of the manifold. The plate 36 holds the cannulae 38 to the manifold 34. A set of valves 52 are disposed in the manifold. The valves 52 regulate cement flow out of the channels internal to the manifold.

Figure 8:
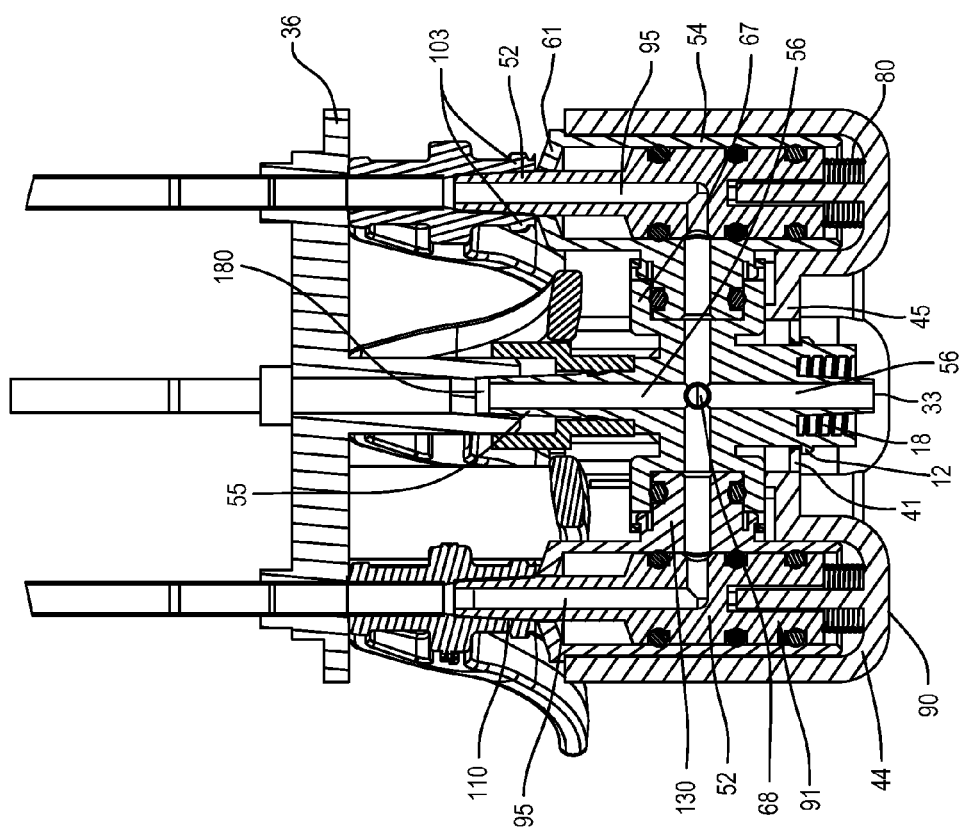
FIG. 8 is a cross-sectional view of the manifold in the plural fill mode illustrating a continuous flow path from a central channel to a plurality of sub-channels and a collar attached to a distal end of a block central channel male fitting.
Figure 8A:
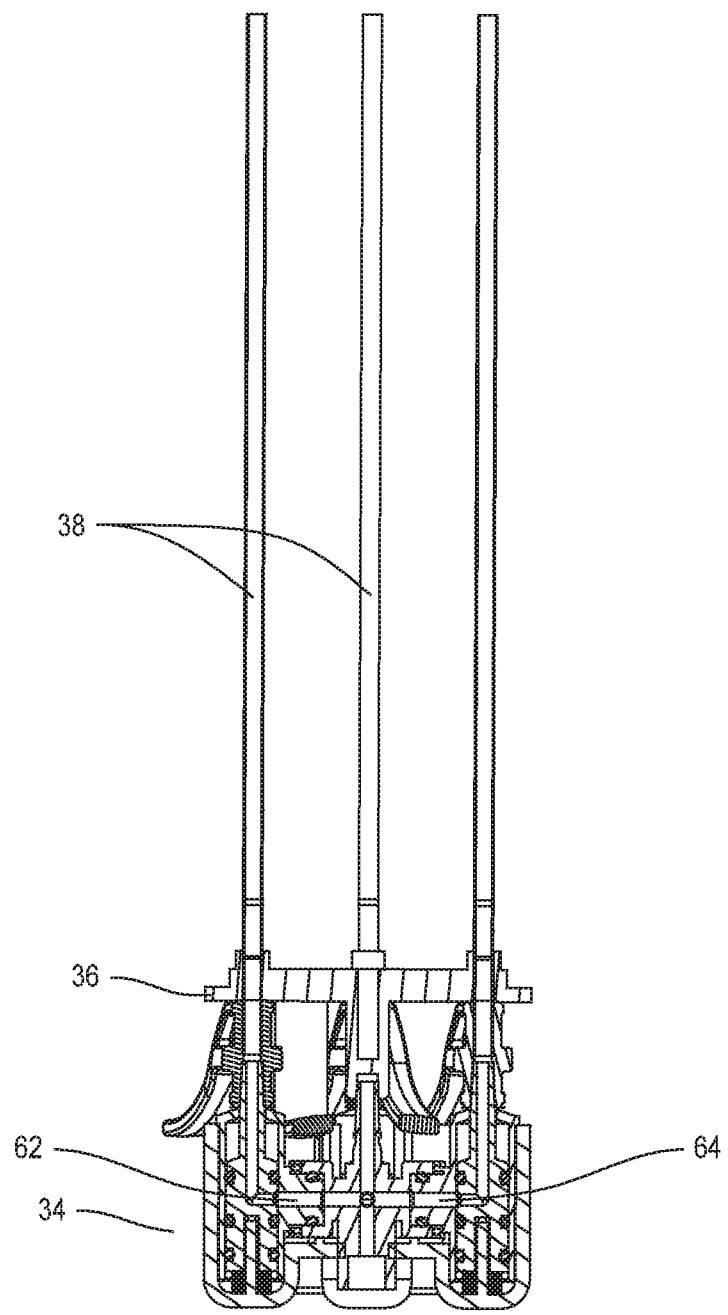
FIG. 8A is a cross-sectional view of the manifold in the plural fill mode illustrating the alignment of sub-channels with central channel, the plate, and four cannulae.

The manifold 34 includes a housing 44, now described by reference to FIGS. 4A, 8 and 13. The housing 44 includes a base 45. Base 45 is formed with a center located manifold inlet opening 33. Base 45 is further formed to have a plurality of circumferentially spaced apart slots 41 that extend radially inwardly from the outer perimeter of manifold housing inlet opening 33. Slots 41, as shown in FIG. 8, do not extend the whole length across the opening 33. Slots 41 have a cross-sectional width that is less than the thickness of base 45. The reduced thickness of slots 41 makes the slots 41 flexible relative to the rest of the base 45. Housing 44 also is comprised of four side walls 47, 49, 51 and 53 that extend upwardly from the side edges of the base 45.

Figure 5:
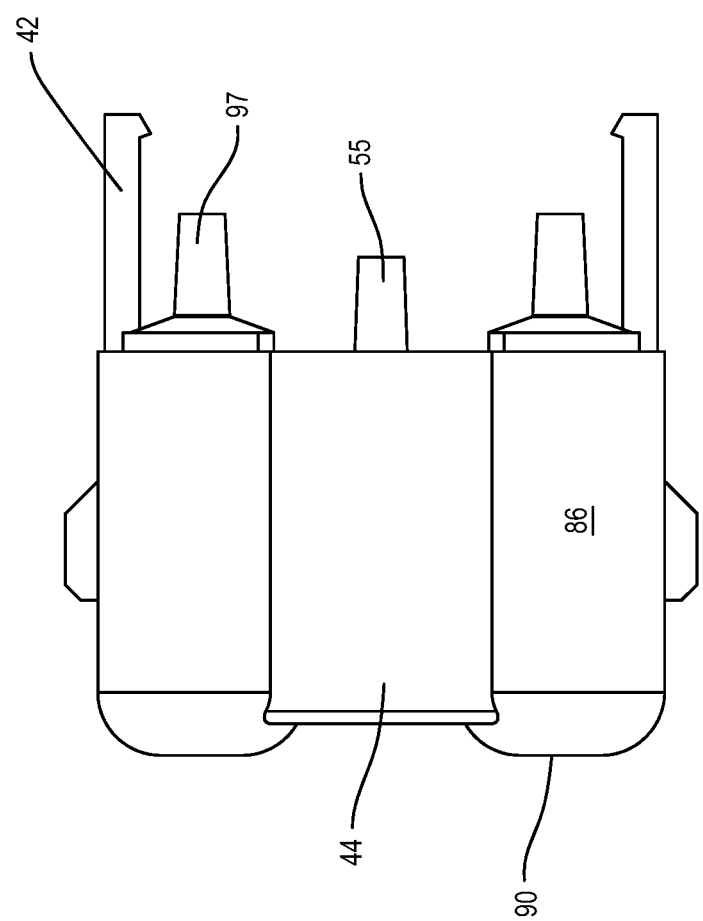
FIG. 5 is a plan view of the manifold housing illustrating a manifold housing foot and arm.
Figure 13:
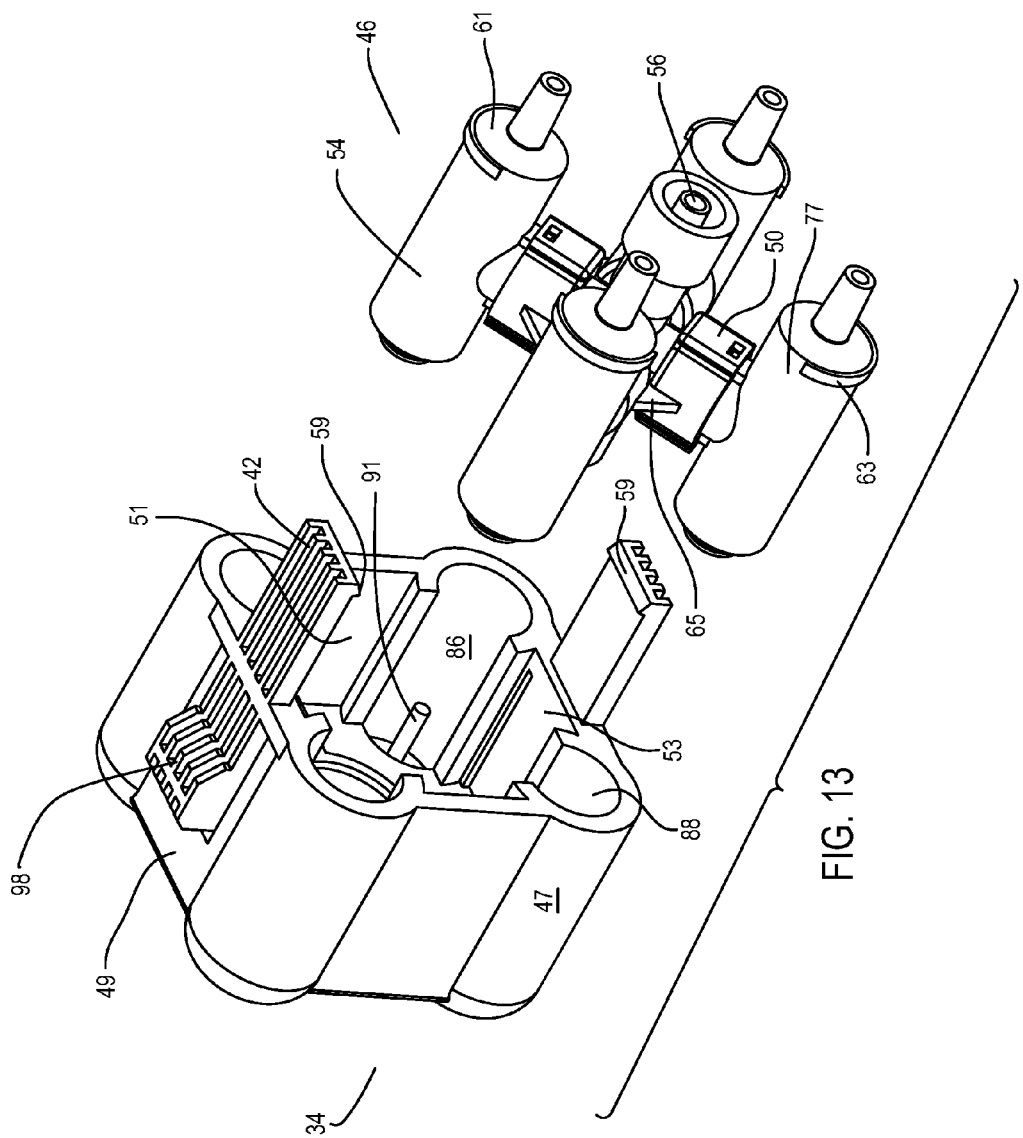
FIG. 13 is an exploded view of the manifold illustrating the manifold housing and the block with all four valve assemblies attached.

A turret 86, as shown in FIGS. 3 and 13, is located between each pair of adjacent side walls 47, 49, 51 and 53. Each manifold housing turret 86 in cross-section appears C-shaped. The turret has an outer section, not identified, that curves outwardly from outer surfaces of the side walls with which the turret is integral. Each turret has two inner sections, not identified. The turret inner sections, which are located inside the housing 44, curve inwardly towards each other but do not meet. Each C-shaped turret 86 defines within the housing 44 a bore 88 that extends the length of the turret 86. As shown in FIGS. 4A and 5, a foot 90 extends below each turret 86. Each foot 90 has a slightly flattened semi-spherical shape. Feet 90 project proximally outwardly of housing base 45. A post 91 extends upwardly from the base of each foot 90, as shown in FIG. 8. Each post 91 extends upwardly along the center axis of the bore 88 internal to the turret 86 with which the foot is integral.

A pair of opposed arms 42 are integrally molded with manifold housing 44. Each arm 42 extends forward from a separate one of the side walls 49 and 53. Each arm 42 has a shoulder 98 located below the top of the associated side wall 49 or 53. Shoulders 98 project outwardly beyond side walls 49 and 53. The arm shoulder 98 is separate from the associated side wall 49 or 53 (gap between the arm and adjacent side wall not identified). Each arm 42 is able to flex relative to the associated side wall 49 or 53. A finger 59 extends along the top surface of each arm 42. Each finger 59 extends inwardly, towards the opposed arm 42.

Figure 14:
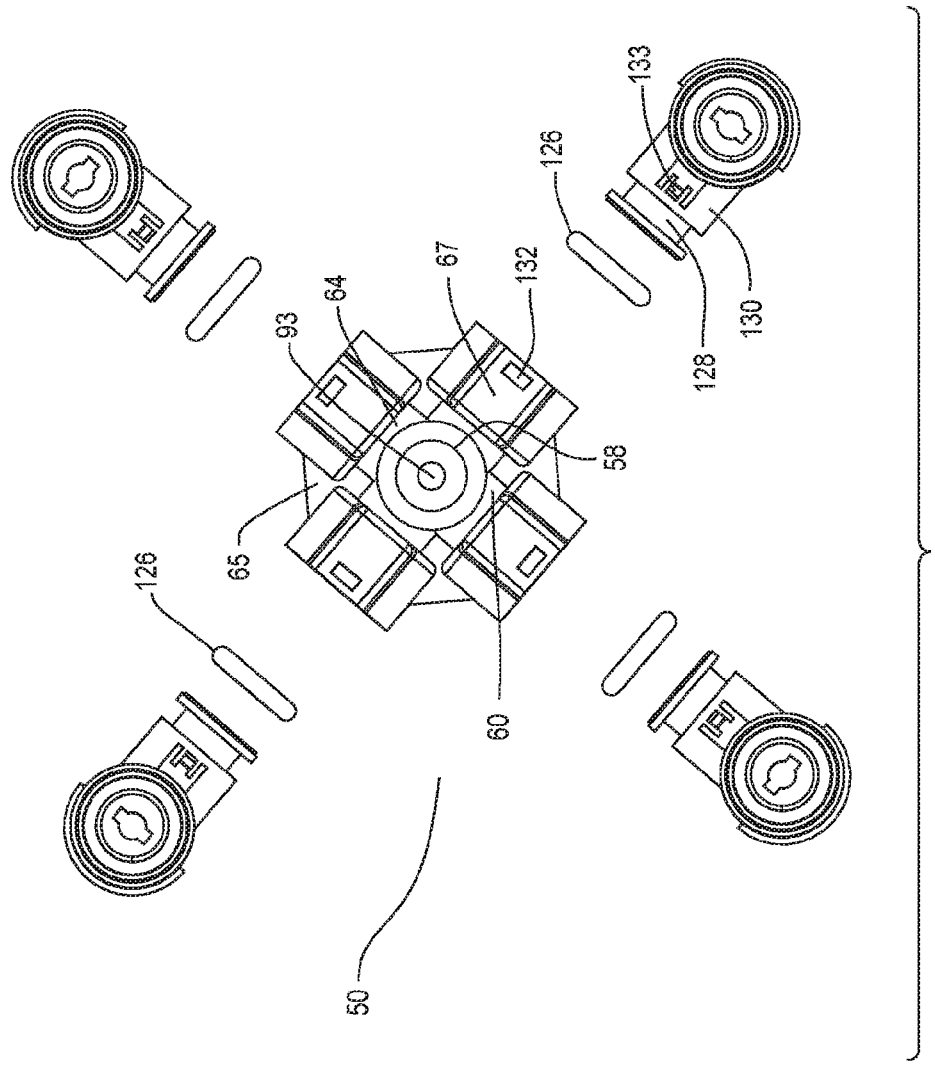
FIG. 14 is an exploded view of the manifold block and a plurality of valve seats and O-rings.
Figure 15:
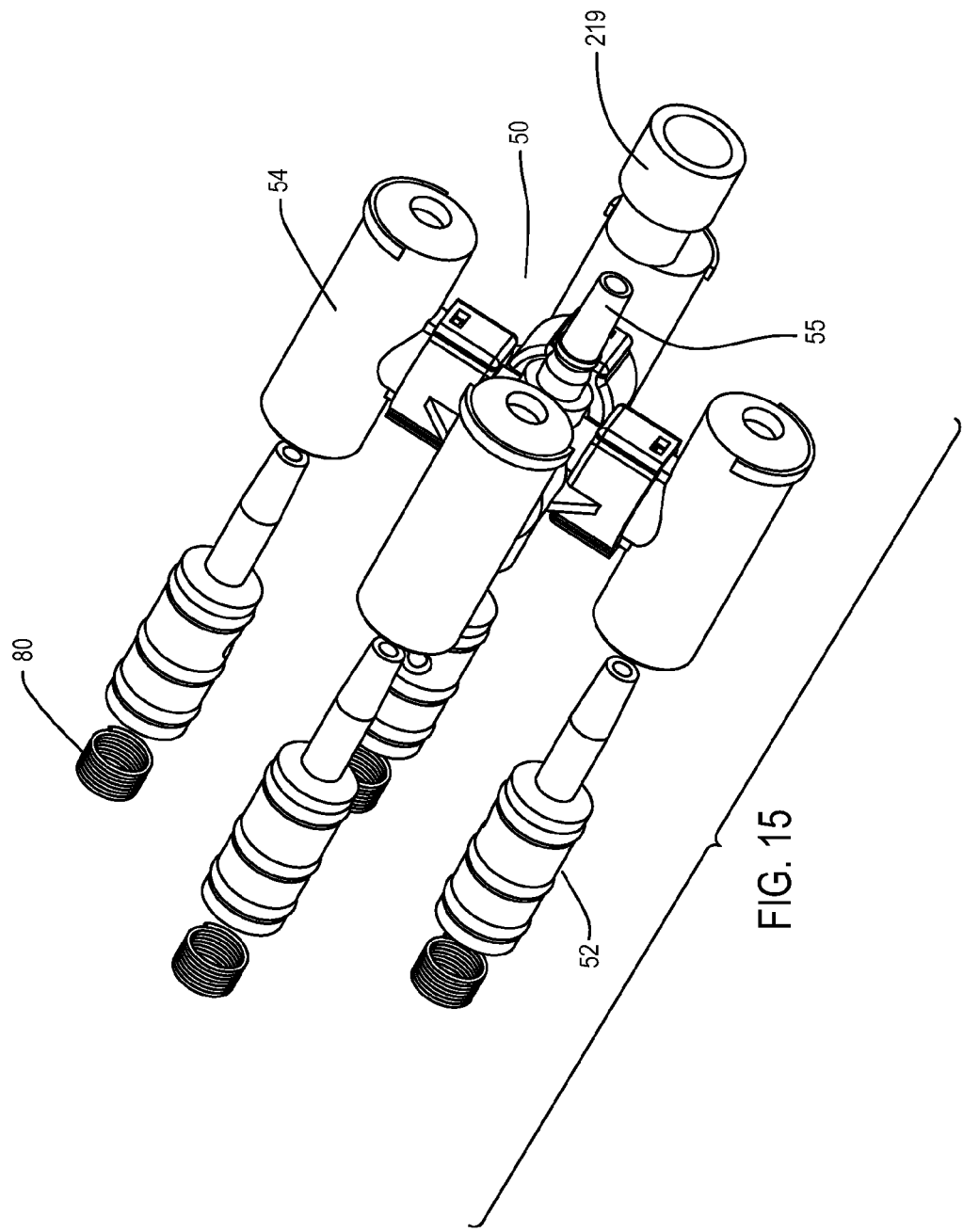
FIG. 15 is an exploded view of the manifold valve assembly, block and a spring.

A block 50 is seated within manifold housing 44. The block, initially described by reference to FIGS. 14 and 15, is formed from a single piece of plastic. The block 50 has a center core 93. Four equiangular spaced apart sockets 67 project outwardly from the core 93. In alternative embodiments of this invention, sockets 67 are not equiangularly spaced apart. Sockets 67 are located above the base of block core 93. Each socket 67 has a generally cylindrical void space (not identified). Each socket 67 is further formed so that in the top and bottom wall of the socket there are opposed small rectangular openings 132 into the void space. A reinforcing web 65 extends between each pair of adjacent sockets 67 as shown by FIG. 14. In one version of the invention, block web 65 is defined by only two separate webs. A tapered male fitting 55 extends distally away from block center core 93. Male fitting 55 has opposed proximal and distal sections.

Block core 93 has a proximal end section (not identified) that is generally cylindrically shaped. A ring 12 extends circumferentially around the core proximal end section, as shown by FIGS. 4A and 8. Ring 12 extends from the proximal face of block 50. A cylindrical boss 14 extends proximally outward from ring 12. Boss 14 is formed to have a closed end threaded bore 16 that extends upwardly from the proximal end of the boss. More specifically, bore 16 is formed to engage with the complementary threaded end of the delivery tube 32 of mixing system 30, as seen in FIG. 1. A Luer fitting 18 extends proximally away from block center core 93 along its longitudinal axis. Fitting 18 extends proximally away from the proximal directed face of bore 16. The Luer fitting 18 extends proximally away from the proximal open end of bore 16. Luer fittings of this invention are either standard ISO 594-1 or 594-2.

Figure 9:
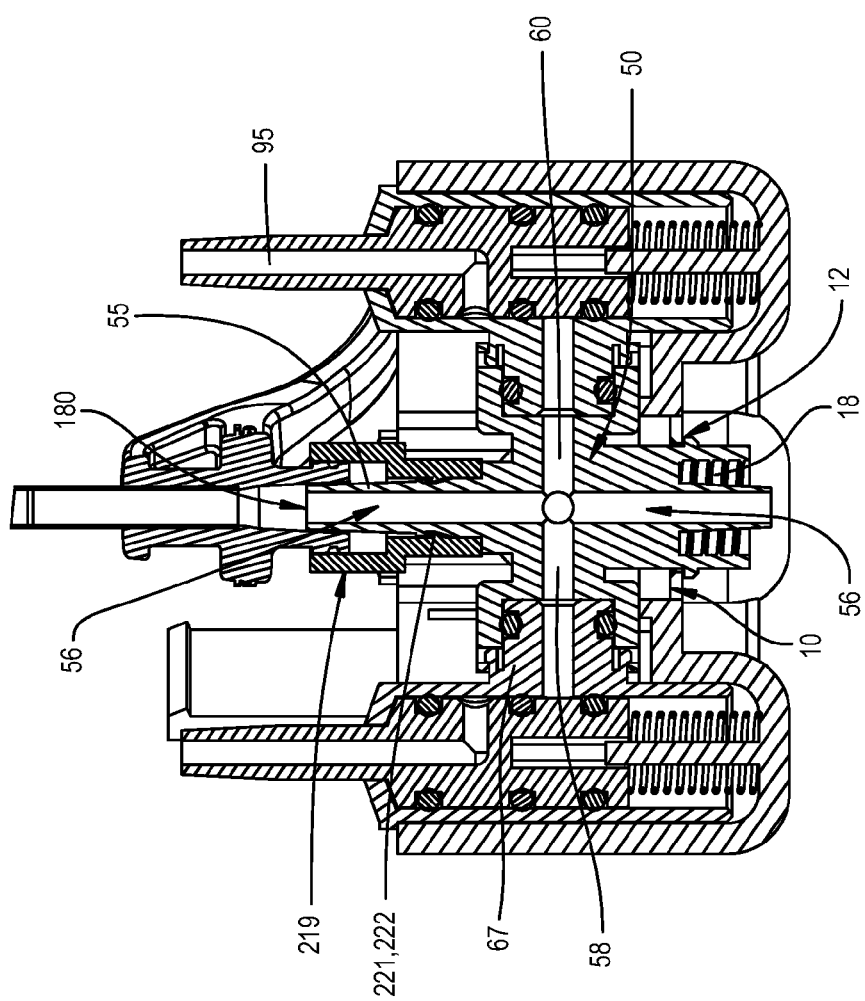
FIG. 9 is a cross-sectional view of the manifold in a single fill mode illustrating a non-continuous flow path and the absence of the plate.

As seen best in FIGS. 4A and 9, block 50 has a plurality of angularly spaced apart tabs 10 that extend radially from proximal end section of block core 93. Tabs 10 have a cross-section that facilitates seating of the tabs 10 in the manifold housing slots 41.

Block 50 is further formed with a number of internal channels. A central channel 56 extends distally forward through Luer fitting 18. Central channel 56 extends axially through the block center core 93. In a preferred embodiment of this invention, central channel 56 has a diameter ranging from approximately 1 mm to 5 mm. The most distal portion of central channel 56 functions as the lumen through male fitting 55. A distal end opening 180 defines a distally located opening of block central channel 56. As seen in FIGS. 8 and 9, a collar 219 is attached to male fitting 55 with a tapered protrusion 221. Collar 219 has a proximal and a distal section (not identified). An inner and outer diameter of collar proximal section is less than an inner and outer diameter of collar distal section, as shown by FIG. 9. A distal end of collar distal section defines an opening (not identified). A tapered protrusion 221 is circumferentially located within an inner surface of collar proximal section. Male fitting 55 has a complementary molded-in tapered recess 222. Tapered protrusion 221 secures collar 219 to the male fitting 55, as male fitting 55 is secured around distal end of block central channel 56, as shown in FIG. 9. Collar 219 is separate from block 50. In one version of the invention, collar 219 is formed from a single piece of plastic.

A set of sub-channels 58, 60, 62 and 64 extend outwardly from a cross-bore opening 68 of central channel 56. Sub-channels have a diameter ranging from approximately 1 mm to 5 mm. Each block sub-channel extends to one of the socket 67. Each sub-channel opens into the base of one of the sockets 67. In one version of the invention, sub-channels 58, 60, 62 and 64 extend perpendicularly away from the longitudinal axis of the central channel 56. In alternative embodiments of this invention, sub-channels 58, 60, 62 and 64 may be angled in any direction away from the longitudinal axis of the central channel 56.

Each valve assembly 46 as seen in FIGS. 8 and 15, includes a valve 52 housed inside a valve seat 54. Valve seat 54 is a single piece of plastic. Valve seat 54 has a tubular-shaped housing 77, as shown by FIG. 13. The outer diameter of housing 77 is designed to facilitate the slip fitting of the housing 77 in a manifold housing turret bore 88. The proximal end of valve seat housing 77 is open-ended. A cap 61 extends over the distal end of housing 77. Cap 61 is formed with a through bore center (not identified) on the longitudinal axis of the housing 77, as shown in FIG. 8. A rim 63, shown in FIG. 13, extends partially around the outer surface of valve seat housing 77. Rim 63 is located slightly below cap 61, best seen by FIGS. 3 and 13. When valve seat 54 is fitted in a turret bore 88, rim 63 abuts the outer face of the turret 86 so as to limit the movement of the valve seat 54 into the turret 86.

A boss 130, also part of the valve seat 54, is integral with the seat housing 77, as shown in FIGS. 8 and 14. Each boss 130 extends perpendicularly to the longitudinal axis of associated housing 77. Each boss 130 is cylindrical. The outer diameter of the valve seat boss 130 is such that the boss can be fitted in the void space defined by the block socket 67, as seen in FIG. 8. It should further be appreciated that the boss can fit between the spaced apart sections of the associated turret 86 internal to the housing 44. A bore (best seen in FIG. 9 though not identified) extends inwardly from the outer face of the boss 130 axially through the boss 130. The boss bore opens into the void space within valve seat housing 77. When the boss 130 is seated in the complementary socket 67 of block 50, the block sub-channels 58, 60, 62 or 64, internal to the socket 67, open into the valve seat bore. Valve seat boss 130 has a molded-in snap finger 133, shown by FIG. 14. Each finger 133 is dimensioned to seat in one of the openings 132 in one of the sockets 67 integral with block 50. Valve seat boss 130 is further formed to have a groove 128 that extends circumferentially around the outer surface of the boss 130, shown in FIG. 14. An O-ring 126 is seated in groove 128.

Figure 16:
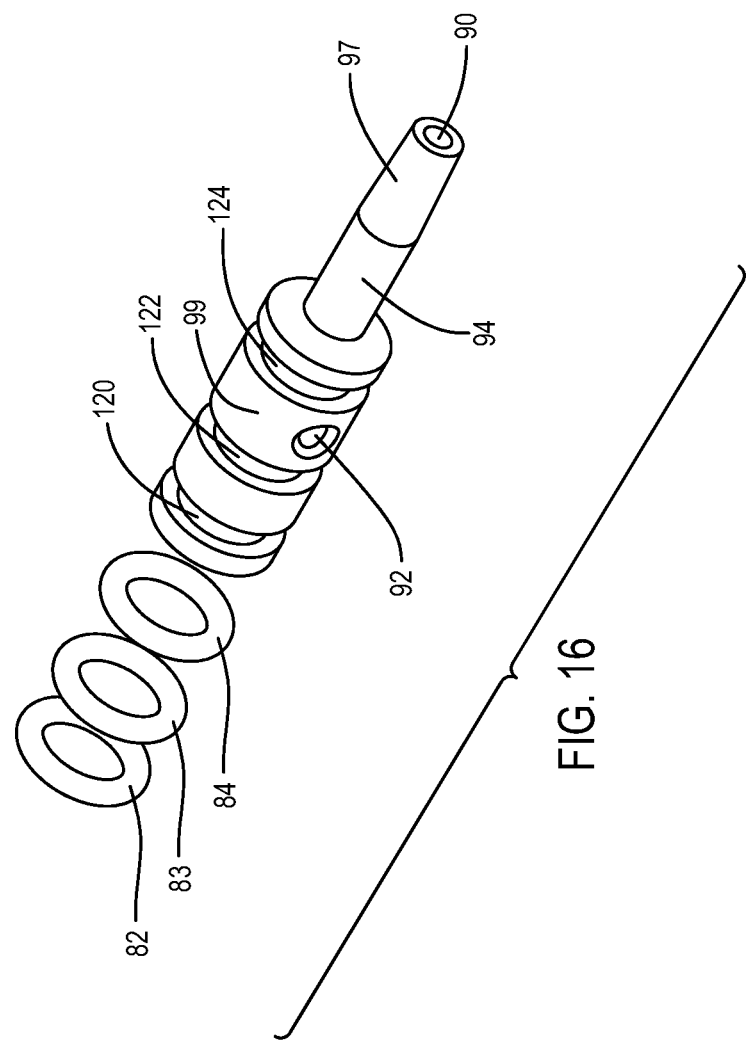
FIG. 16 is an exploded view of a valve and a plurality of valve O-rings.

Valve seat 54 houses a valve 52, and O-rings 82, 83 and 84, as shown by FIGS. 15 and 16. O-rings 82, 83 and 84 are all of equal diameter. Valve 52 includes an outlet opening 90, an inlet opening 92, a stem 94, a tapered male fitting 97, and a body 99, according to FIGS. 15 and 16. The stem 94 extends distally away from valve body 99. Valve body 99 has a larger diameter than valve stem 94. Tapered male fitting 97 is located on the distal end of valve stem 94. Valve body 99 includes three annular grooves 120, 122 and 124 spaced apart on valve body, as shown in FIG. 16. Annular grooves 120, 122 and 124 are approximately diametrically equivalent to O-rings 82, 83 and 84 so that the O-rings are seated in annular grooves. Inlet opening 92 is located on valve body 99 and between annular grooves 122 and 124. Outlet opening 90 is located at the distal end of tapered male fitting 97 of valve 52. The diameter of valve inlet opening 92 is equivalent to the diameter of each sub-channel 58, 60, 62 and 64. Inlet opening 92 aligns with openings of block sub-channels 58, 60, 62, and 64 when a cannula female fitting 69 is in compression with male fitting 97. An L-shaped channel 95 extends from each valve opening 92. The elongated portion of channel 95 functions as the lumen extending through valve body 99, valve stem 94, and valve male fitting 97. Valve outlet opening 90 is the end of the channel 95. A closed-end bore (not identified) is located at a proximal end of valve body 99, as shown in FIG. 8. This bore has a diameter approximately equal to the outer diameter of post 91. In a preferred embodiment of this invention, valve 52 is a piston valve.

Figure 2:
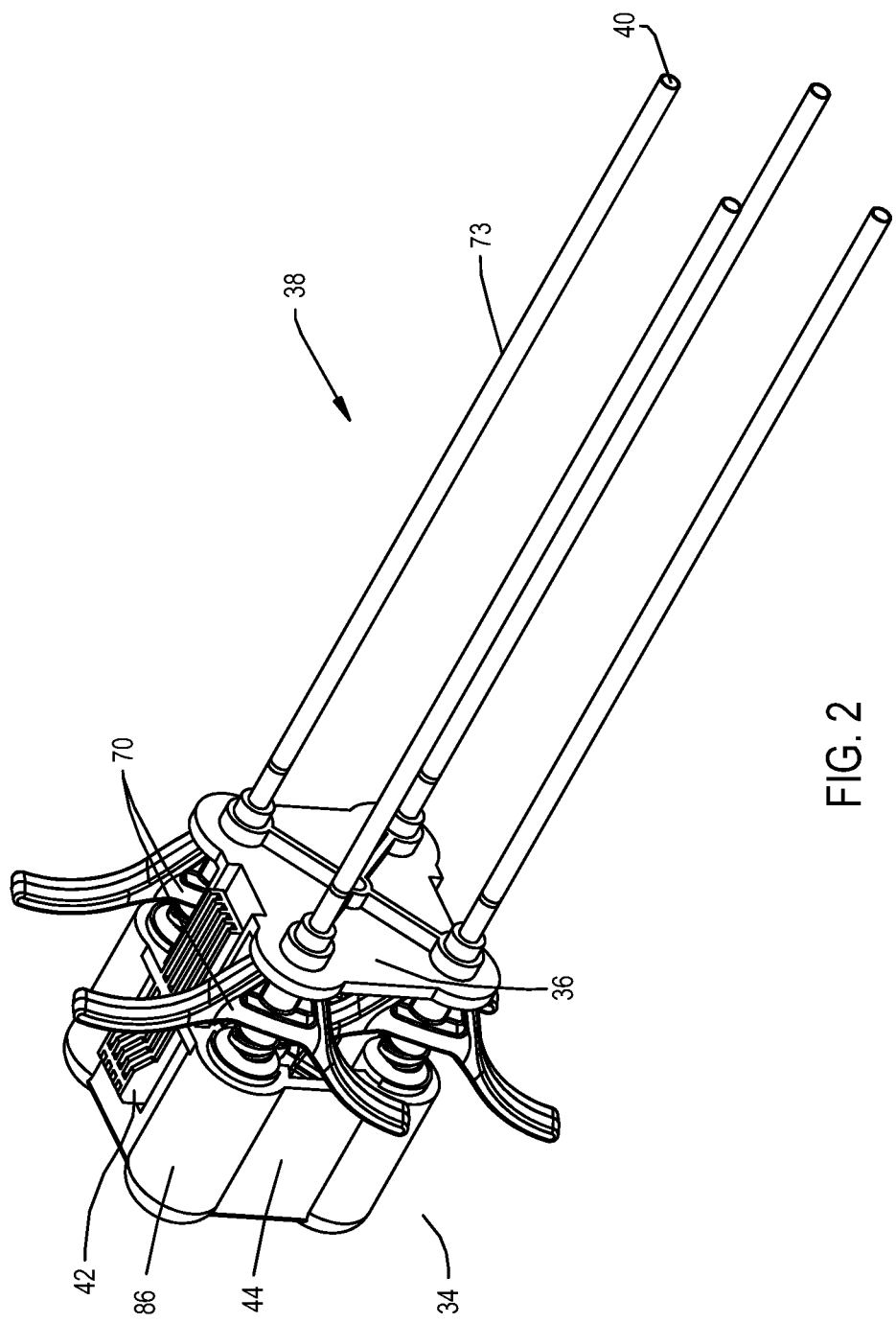
FIG. 2 is a perspective view of the manifold including a manifold housing, a plate and four attached cement cannulae.
Figure 7A:
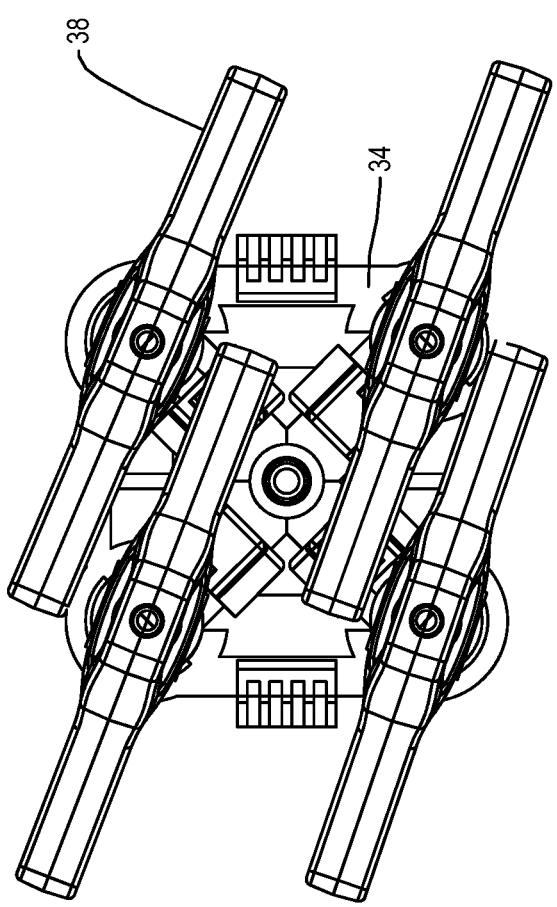
FIG. 7A is a plan view of the distal end of the manifold, without the plate, and four loaded cannulae secured to each valve opening.

As shown in FIG. 2, plural cement cannulae 38 are attached to the manifold 34. Each cement cannula 38 has opposed proximal and distal ends. As shown in FIG. 6, cannula 38 is comprised of a finger-hold 70, a hub 66, female fitting 69, a hub bore 71 (not shown), and a tube 73. Finger-hold 70 is generally wing-shaped and flares outwardly from the cannula hub 66. Owing to their wing-shaped finger-hold 70, cannulae 38, as shown in FIGS. 2 and 7, are positioned at an angle relative to one another so that up to four cannulae may be simultaneously held by manifold 34 for plural filling. Hub 66 is a boss that extends radially outwardly from the proximal end of cannula tube 73 and is seated over the proximal end of tube 73. Tube 73 is seated within hub bore 71 at the distal end. Tube 73, with hub bore 71, defines a lumen or void space that extends the length of cannula 38 opening into cannula opening 40, as shown in FIG. 2.

As shown by FIG. 8, female fitting 69 has a threaded section (not identified), and a tapered bore 103. Tapered bore 103 has a tapered inner surface 110 that is conical in shape and which angles inwardly from the proximal end of the cannula 38. Tapered inner surface 110 defines the bore space of female fitting 69. In a preferred version of this invention, female fitting 69 is a standard ISO Luer fitting generally found on bone cement cannulae.

As shown in FIGS. 8 and 15, at a closed end of each turret bore 88 is a spring 80. As shown in FIG. 8, spring 80 is coaxially positioned around post 91 of housing 44 proximally away from O-ring 82. Spring 80 is a coil compression spring and is comprised of metal, plastic or stainless steel. The inner diameter of spring 80 is equal to the outer diameter of post 91. Spring 80 is present in all four bores 88 of turrets 86. In an alternative embodiment of the invention, the biasing force of spring 80 may be replicated with a gasket, a rubber fitting, a piece of foam, or a molded-in feature.

Figure 10:
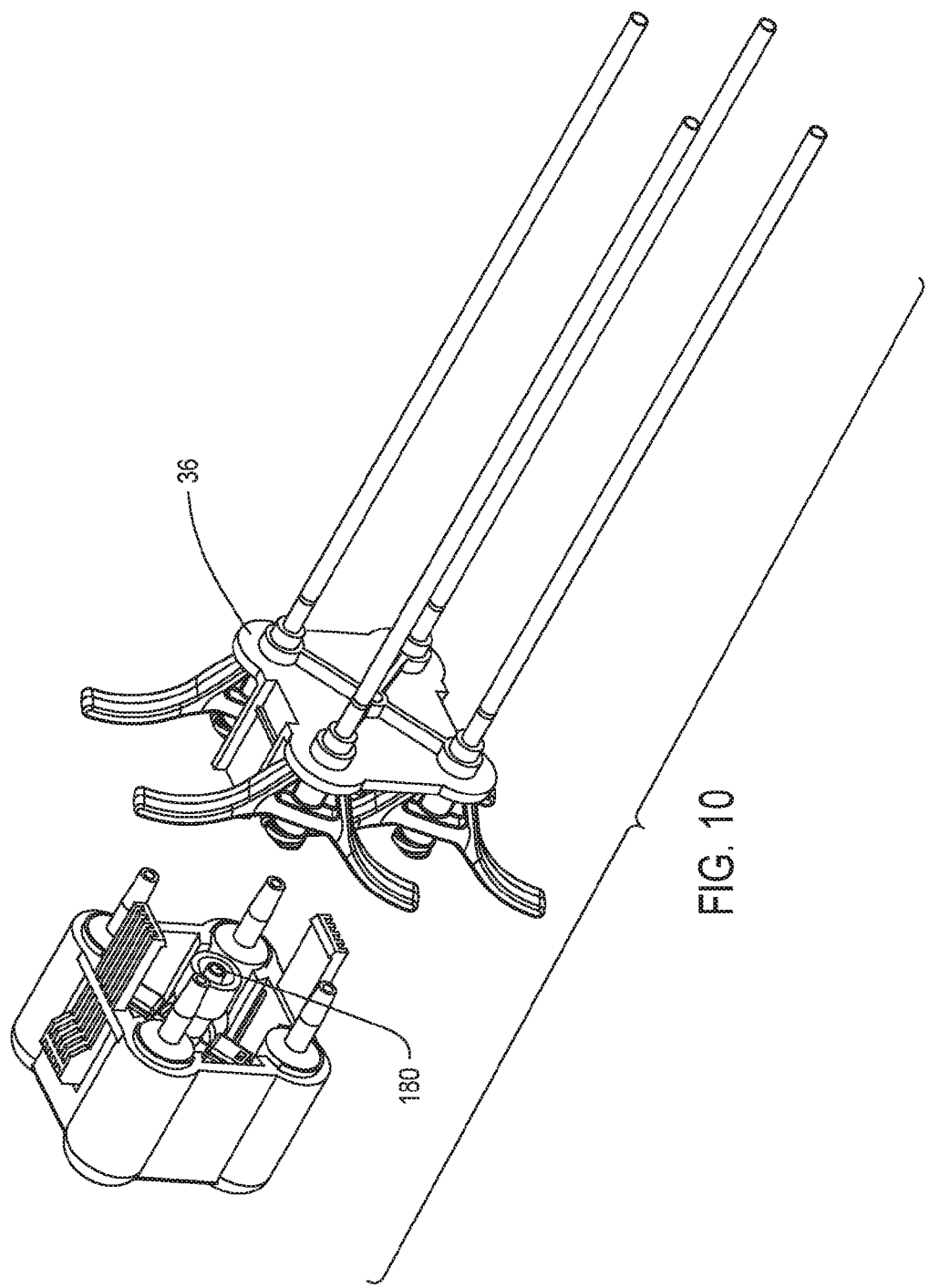
FIG. 10 is an exploded view of the manifold illustrating the manifold housing with a block and a plurality of valve assemblies, and the plate with a plurality of attached cannulae.
Figure 17:
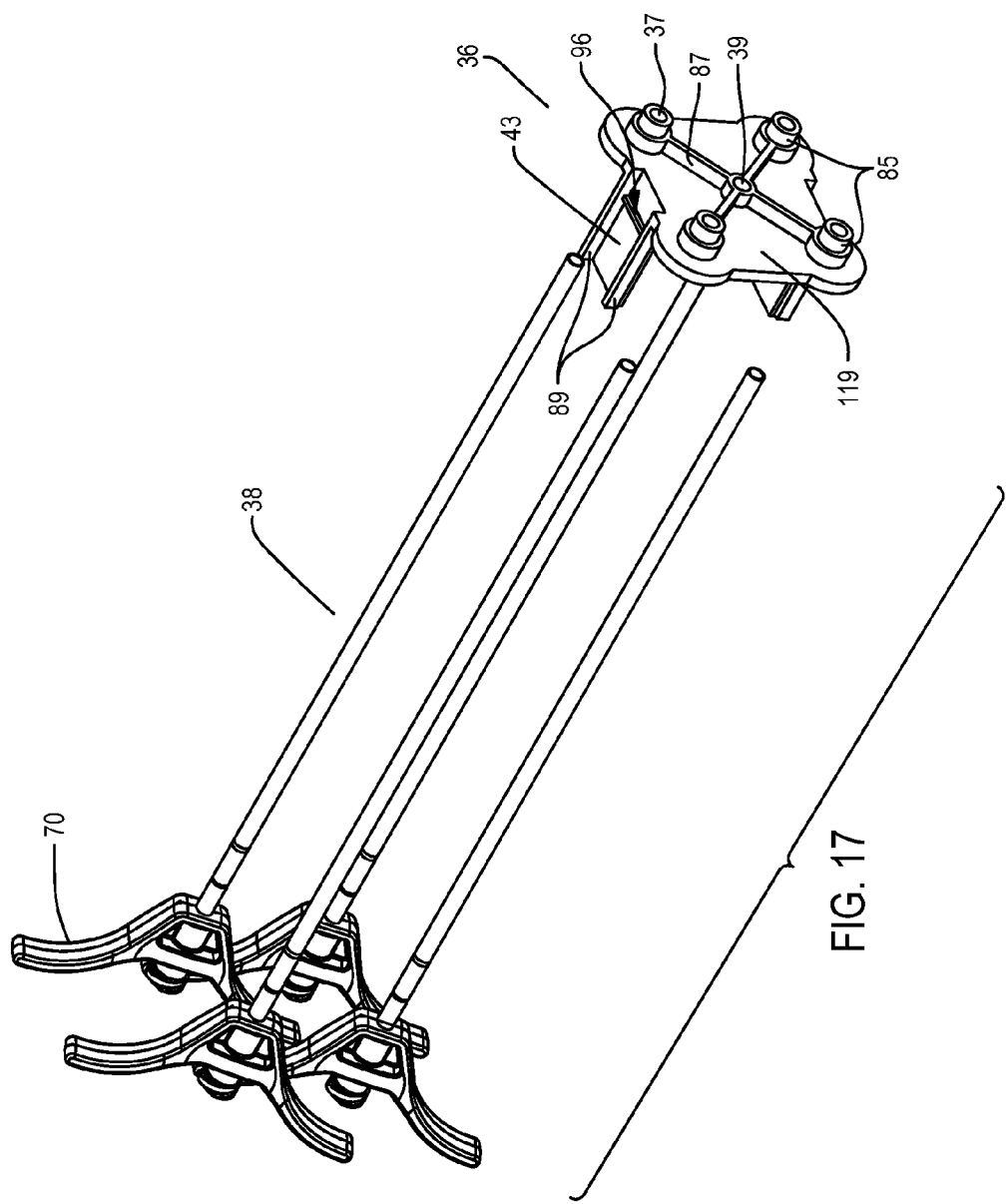
FIG. 17 is an exploded view of a plurality of cement cannulae and the plate illustrating a pair of opposed arms.

Furthermore, as shown in FIGS. 1, 10, and 17, manifold 34 includes a plate 36. Plate 36 holds the cement cannulae 38 to manifold housing 44 during filling. Plate 36 has a base 119. Base 119 is flat with a thickness ranging from approximately 1.25 mm to 3.0 mm. Four openings 37 extend through the opposed faces of plate 36. Each opening 37 is spaced on plate 36 to correspond with, and coaxially align a separate one of the valve fittings 97. Each opening 37 is also diametrically equivalent to the diameter of cannula tube 73. Plate 36 additionally has a cylindrical post 39 (not shown) that extends from the proximal face of the plate 36. Post 39 is located centrally on plate 36 so as to correspond co-axially with block fitting 55. Post 39 defines a closed-end bore (not identified) that extends upwardly from the proximal end of the post. The diameter of closed-end bore of post 39 is equal to the outer diameter of fitting 55.

Rings 85 integral with the plate 36 extend outwardly from the distally directed face of the plate. Each ring 85 is located around a separate one of the openings 37. Ribs 87 that are arranged in an "X" pattern also extend outwardly from the distally directed face of the plate 36. Each rib 87 extends inwardly from one of the rings 85 to the center of the plate. Ribs 87 serve to stiffen plate 36.

Two legs 43 are integral with and extend proximally away from plate 36. Legs 43 are formed integrally with the plate and are flexible relative to the plate 36. Each leg 43 is generally in the form of a rectangularly shaped tab. Two raised edges 89 extend outwardly from the longitudinally extending sides of the leg 43. A web 96 extends outwardly from the outer surface of each leg 43 between the raised edges 89. Web 96 is located closer to the plate 36 than the proximal ends of each leg 43. The distance between each pair of raised edges 89 is equal to the width across an arm 42. Also, the distance across the outer surfaces of the opposed legs 43 is slightly less than the distance across the opposed fingers 59 integral with manifold housing arms 42.

Manifold is assembled by inserting springs 80 coaxially over posts 91 internal to the manifold housing 44. O-rings 82, 83 and 84 are seated over valve grooves 120, 122 and 124, respectively, as shown in FIG. 16. Valve 52 of valve assembly 46 is then seated within valve seat 54 along with O-rings 82, 83 and 84, as shown in FIGS. 15 and 16. This process is repeated until all four valves 52 are seated within valve seats 54.

O-ring 126 is seated over boss groove 128, as shown by FIG. 14. Next, molded-in snap feature 133 of each valve seat boss 130 is then snap-fitted with each respective block 50 molded-in snap feature 132, as shown by FIG. 14. Boss 130 is integral with valve seat 54. This process is repeated until all four valve seats 54 are snap-fitted with block 50, as shown by FIGS. 13, 14 and 15. Block 50 with all four valve assemblies 46 attached is next slip-fitted over respective spring 80 and post 91 of manifold housing 44, as shown in FIG. 8. Angularly spaced apart tabs 10 at base of block 50, as seen in FIG. 4A, are then used to snap-fit block 50 between the complementary manifold housing slots 41. Consequently, block 50 along with all four valve assemblies 46, are attached to manifold housing 44, as best seen in FIG. 13. When the manifold is in this state, springs 80 press against the valves. Each spring 80 pushes the valve away from the housing base. Each valve 52 is thus positioned so that the valve bore is out of registration with the complementary block sub channel. Caps 61 prevent the springs 80 from pushing the valves 52 out of the valve seats 54. In alternative versions of this invention, block 50 is secured to manifold housing 44 by using screws, fasteners, a retaining plate, heat staking, or welding.

Cannulae 38 are slip fit through respective plate openings 37. Plate 36 is then position so that the cannulae are disposed over valve fittings 37.

The continued pressing of the manifold housing 44 and plate 36 together overcomes the outwardly directed force that springs 80 impose on the valves. The valves are pressed downwardly over posts 91. Eventually, the valves are displaced by a sufficient distance so that each valve opening 92 aligns with the complementary block sub-channels 58, 60, 62 or 64. As a result of this registration of the valves 52 with the block sub-channels, the valves are in an open state. Simultaneously, with the displacement of the valves to the open state, the fingers 59 integral with the housing arms 42 snap over the webs 96 integral with the plate legs 43. The abutment of the fingers 59 against the webs 96 blocks the force imposed from the springs 80 that push the valves 52 and, by extension, the plate 36 and cannulae 38, away from the manifold housing 44. In order to facilitate this engagement of the manifold housing fingers 59 with the plate 36, it may be necessary to press inwardly on the shoulders 98 in order to pivot the fingers outwardly.

Tapered inner surface 110 angles inwardly from the proximal end of each cannula 38, as shown in FIG. 8, to complement tapered end of valve fitting 97. Tapered male fitting 97 of valve 52 is seated within female fitting 69 so as to create a male-female connection. Exterior walls of valve male fitting 97 create an abutment with the tapered inner surface 110 of female fitting 69, as shown by FIG. 8. This male-female connection provides a continuous flow path from each valve opening 90 to each respective cannula female fitting bore space for fluid communication. In a preferred embodiment of the invention, valve male fitting 97 is Luer-activated. Finger-holds 70 of cannulae 38 are present for the user to grasp the cannulae 38 in order to create a secure male-female connection. Opening 90 of valve male fitting 97 and tapered bore 103 of female fitting 69 are both standard ISO Luers that provide a complete seal between each cannula 38 and each valve 52.

As a consequence of the seating of plate 36 over housing 44, fitting 55 integral with manifold seats in the closed end bore integral with plate post 39.

A. Plural Fill Mode

Once manifold 34 is assembled with four cannulae 38 using plate 36, as show in FIG. 1, cannulae 38 are filled with bone cement. Bone cement is mixed in chamber 283 using paddle 284 of FIG. 1C. Once the bone cement is mixed, the piston 264 is actuated to force cement into delivery tube 32. Threaded section of delivery tube 32 is threadedly attached to manifold block bore 16. Distal end opening of delivery tube 32 is in fluid communication with Luer fitting 18 of block bore 16. Plunger 288 is advanced beyond piston 264 to move the mixed bone cement out of delivery tube 32 into manifold 34. Bone cement flows from tube 32 of the mixing and delivery system 30 into the proximal end opening of central channel 56, via the manifold inlet opening 33, of the block 50. Cement advances distally forward through the central channel 56 of block 50 past cross-bore opening 68. Once cement travels through cross-bore opening 68, cement continues further down central channel 56 into fitting 55. Plate post 39, which extends over the open end of the fitting 55, blocks the flow out of fitting 55.

Once cement has filled the segment of central channel 56 internal to fitting 55, cement is forced to flow through the sub-channels 58, 60, 62 and 64. Cement flows through sub-channels 58, 60, 62 and 64 into the valve bores. O-rings 82, 83, 84 prevent cement leakage between the valve 52 and valve seat 54. O-ring 126 of valve seat boss 130 prevents cement leakage from between the boss 130 and the surrounding socket 67.

The cement then flows from each valve bore into the lumen 40 of the associated cannula 38. Due to pressure exerted by user from the delivery device, cement travels simultaneously through the cannulae lumens 40 until each cannula 38 is filled.

Once cement has simultaneously filled plural cement cannulae 38, the user un-clips the plate 36 from the manifold 34 by depressing the arms 42 inwardly. This results in the arm fingers 59 pivoting away from webs 96 integral with plate legs 43. The plate 36, with the cannulae 38 attached, is then pulled away from the manifold 34 as seen in FIG. 10. The cement-filled cannulae are individually withdrawn from the plate for use.

Once plate 36 is pulled away from the manifold 34, plate 36 carries the cement-filled cannulae. Each cannula 38 is withdrawn from plate 36 one at a time by withdrawing tube 73 from plate opening 37.

As a further consequence of removing the plate 36 from the manifold housing 44, each cannula 38 no longer pushes associated valve 52 into the valve seat. Each valve is free to move within the valve seat. Each spring 80 therefore pushes valve 52 forwardly until valve 52 abuts cap 61. Due to the valve being forward within valve seat, the valve bore moves out of registration with the associated block sub-channel. In other words, the valve returns to a closed state from an open state, as seen in FIG. 9.

If additional cannulae are required during the surgical procedure, the user may re-stock the plate 36 with any combination from one, two, three or four cannulae for filling. Again, where a cannula is mounted to the plate, the cannula 38 overcomes the force of spring 80 and again displaces the associated valve 52 rearwardly within valve seat 54. The valve is returned to the open state. Where a cannula is not mounted to the plate 36, when the plate is reattached, the valve is not displaced by the re-attachment of the plate. The valve, therefore, remains in the closed state.

It should be appreciated that the volume of cement within delivery tube 32 is substantially greater than the volume of cement within all four cement cannulae 38, plus any volume of cement contained within the manifold central channel and sub-channels. The volume of cement in delivery tube 32 is enough to fill at least eight cement cannulae 38. Therefore, a user may perform multiple iterations of the plural fill mode in order to fill a first set of four cannulae followed by a second set of four cannulae.

B. Single Fill Mode

Figure 11:
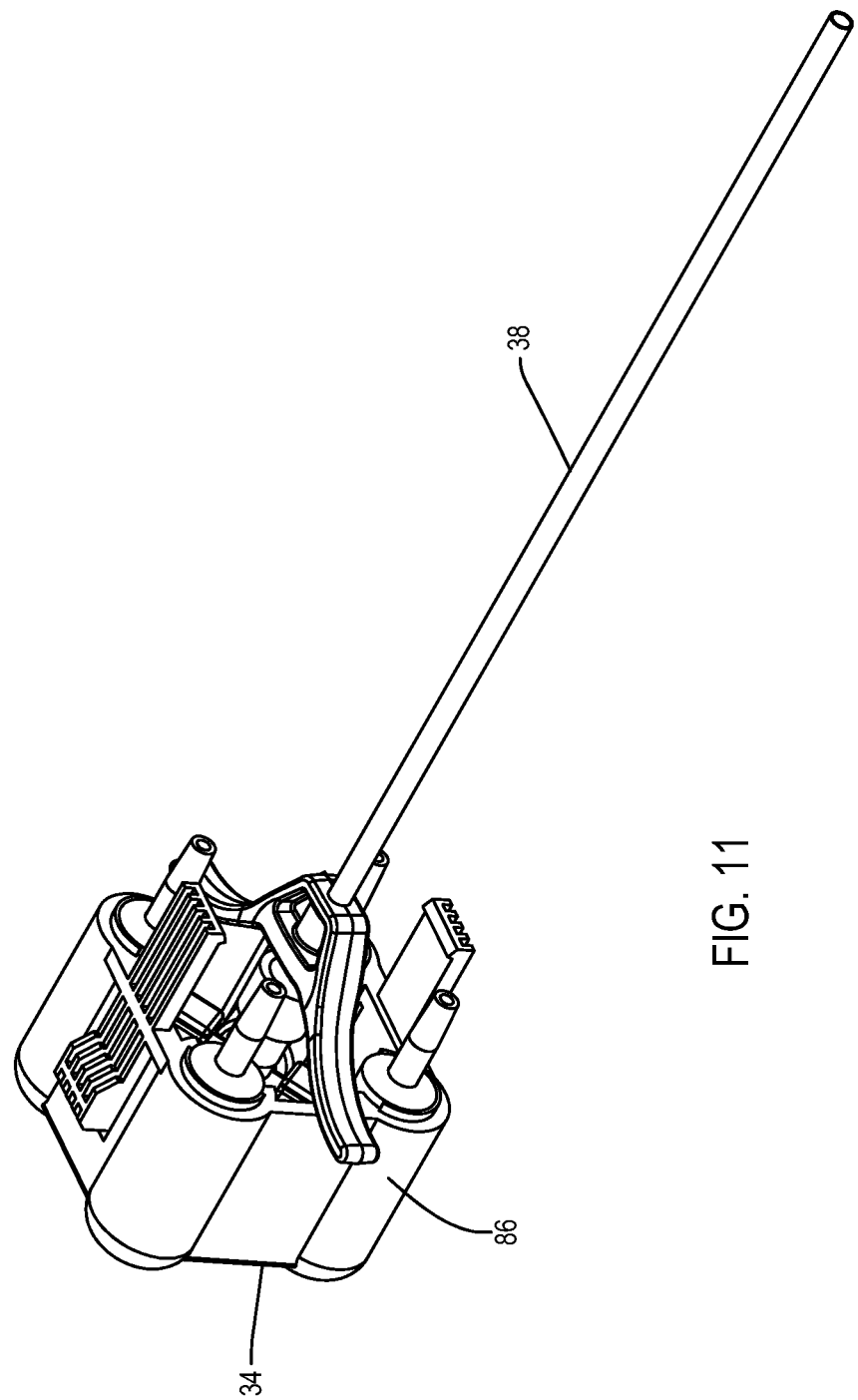
FIG. 11 is a perspective view of the manifold in the single fill mode without the plate and a single cannula attached to the central fitting.
Figure 12:
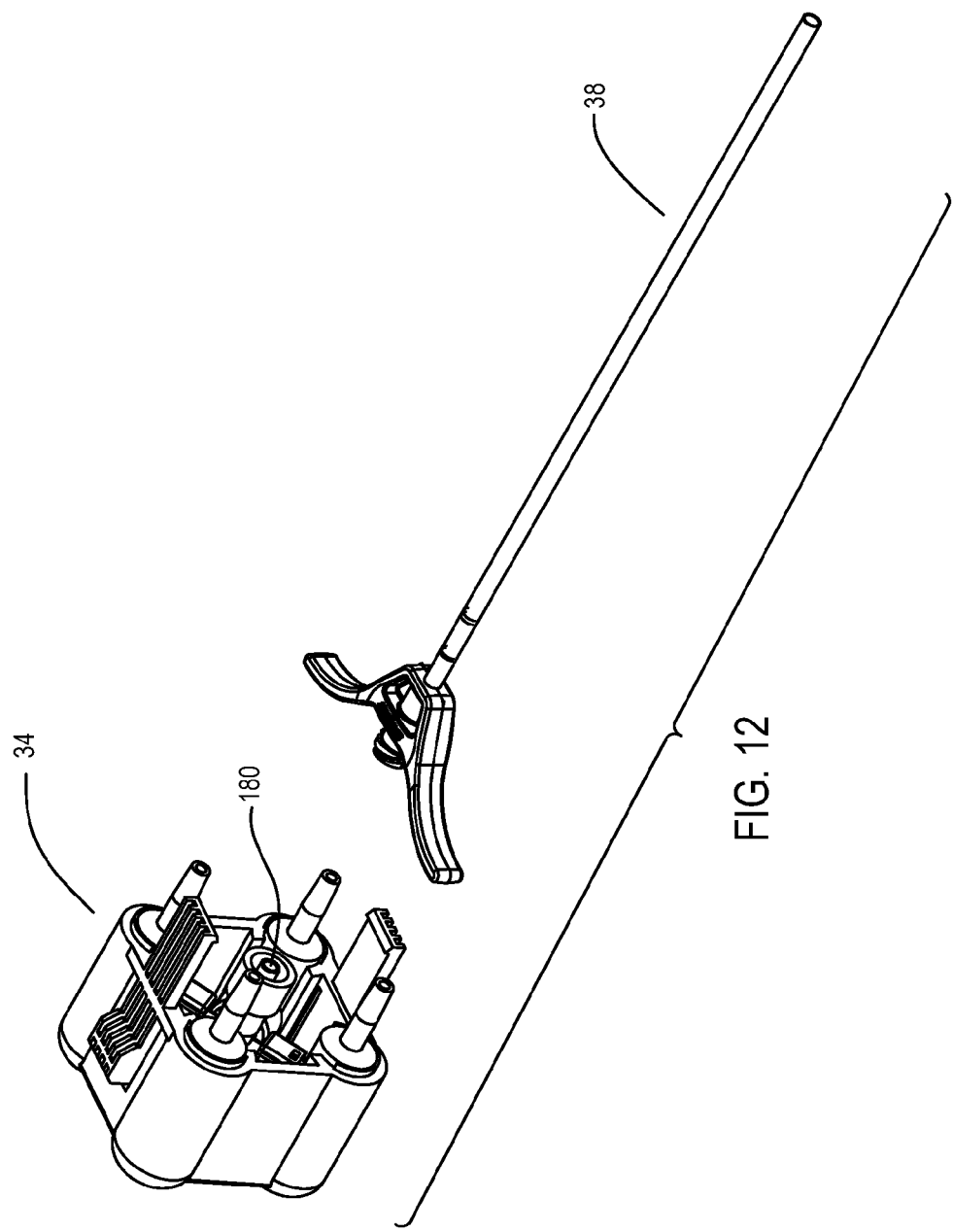
FIG. 12 is an exploded view of the manifold in the single fill mode illustrating the central fitting.

In the event the practitioner only wants to fill cannulae one at a time, system can be operated in a single fill mode, illustrated shown by FIGS. 9, 11 and 12. In this mode, the user does not fit a cannula to the plate or mount the plate to the manifold housing. Instead, the user simply attaches the cannula to the manifold male fitting 55, as shown in FIGS. 9, 11 and 12, via collar 219. Distal opening 180 is defined by the male fitting 55 distal section opening. Since there are no cannulae 38 depressing against the valves 52, the springs 80 continue to hold the valves 52 in the closed state. Consequently, when plunger 288 forces cement through the manifold 34, there is no cement flow of out valve fittings 97. There is only cement flow through block fitting 55 into the attached cannula 38. If the user desires to sequential single fill mode instead of a second plural simultaneous filling, it is within the discretion of the user to do so.

II. First Alternative Embodiment

Figure 18:
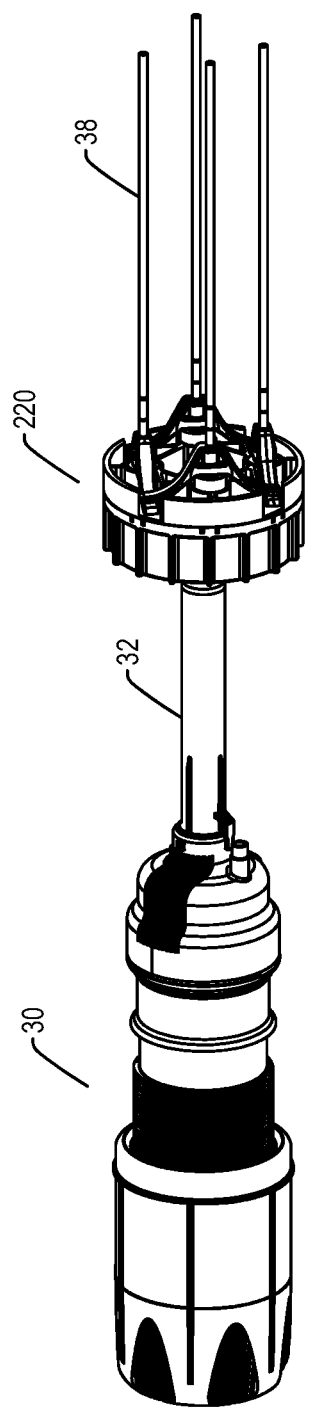
FIG. 18 is a perspective view of an alternative embodiment of the manifold with the mixing and delivery system.
Figure 19:
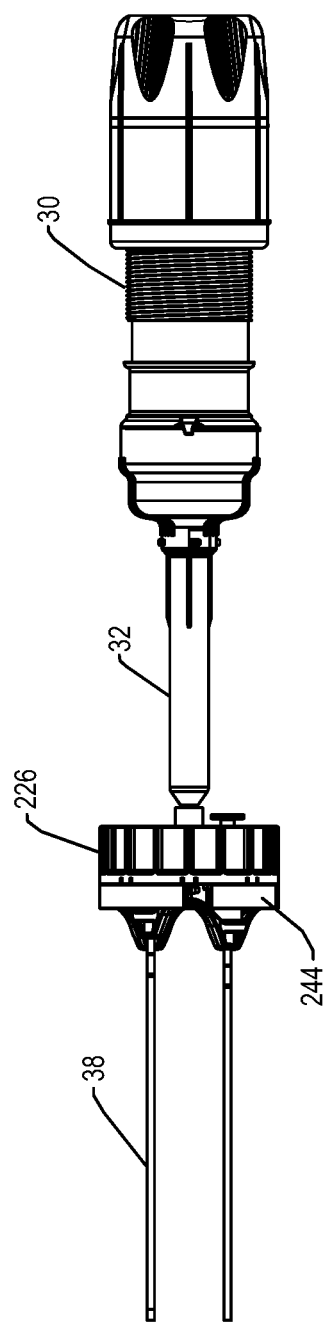
FIG. 19 is a plan view of an alternative embodiment of the manifold with the mixing and delivery system.

Likewise, the manifold of this invention may be alternatively designed to achieve plural simultaneous filling of cement cannulae with a simultaneous release of said cannulae once filling is complete. In this version of the invention, a plurality of cannulae are attached at four separate distally located outlet openings 246. The cannulae 38 are attached to a plurality of respective Luer fittings 232 and 234. FIG. 18 illustrates a bone cement mixing and delivery device 30 with an alternative embodiment of manifold 220.

FIGS. 18-21 illustrate an alternative system of this invention. This system includes the previously described cement mixing and delivery unit 30 and an alternative manifold 220. Manifold 220 is comprised of a two-part cap system including a proximal cap 226 and a distal cap 244. Manifold 220 includes a plurality of gears 238 and 242, a circular plate 268 with a plurality of Luer fittings 232 and 234 extending from a distal face of plate 268, and a locking pin 223. Plate 268 defines a plurality of channels for bone cement to travel within manifold 220.

Figure 20:
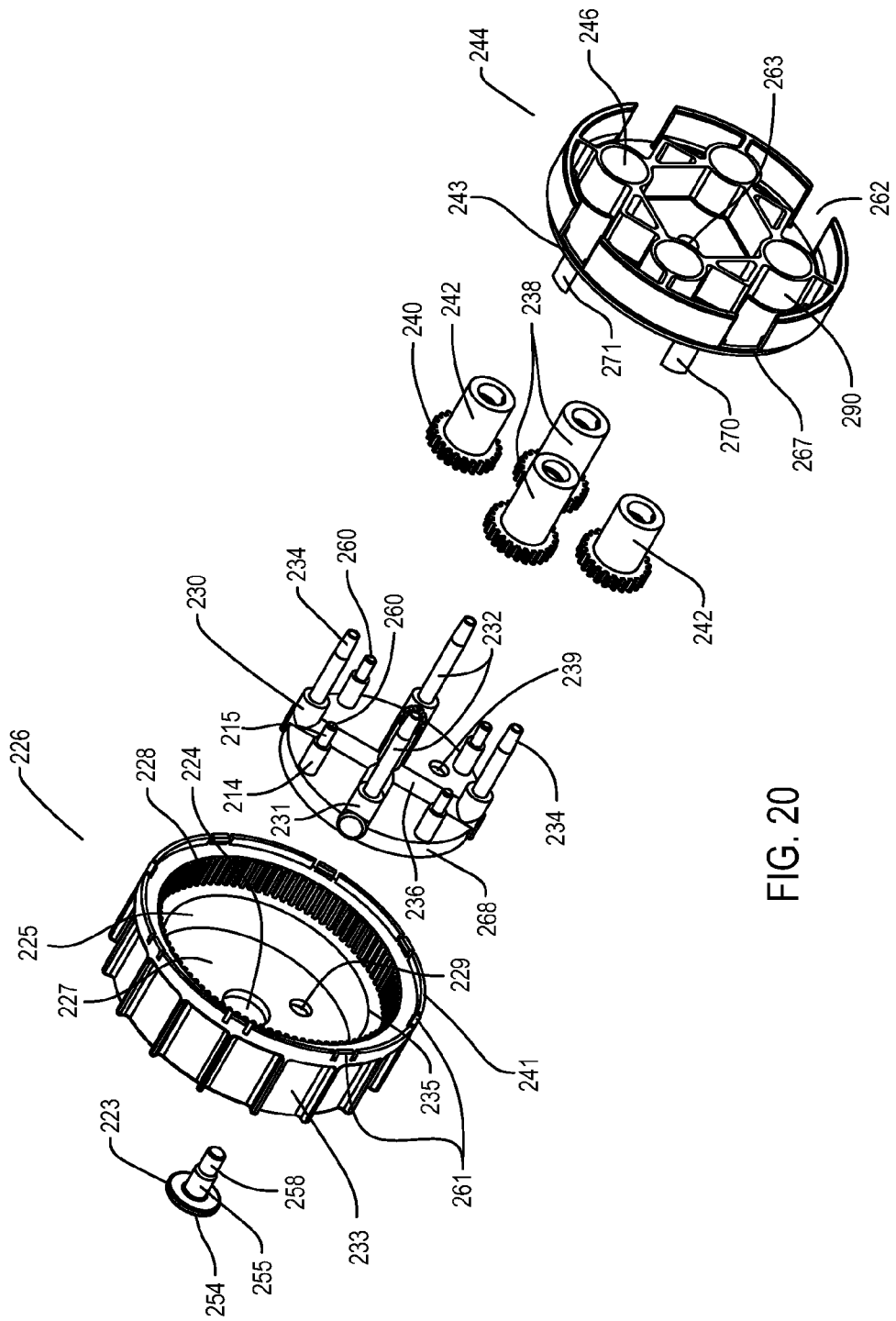
FIG. 20 is an exploded view of an alternative embodiment of the manifold illustrating a proximal cap, a proximal cap locker, a channel body, a plurality of gears, and a distal cap.
Figure 21:
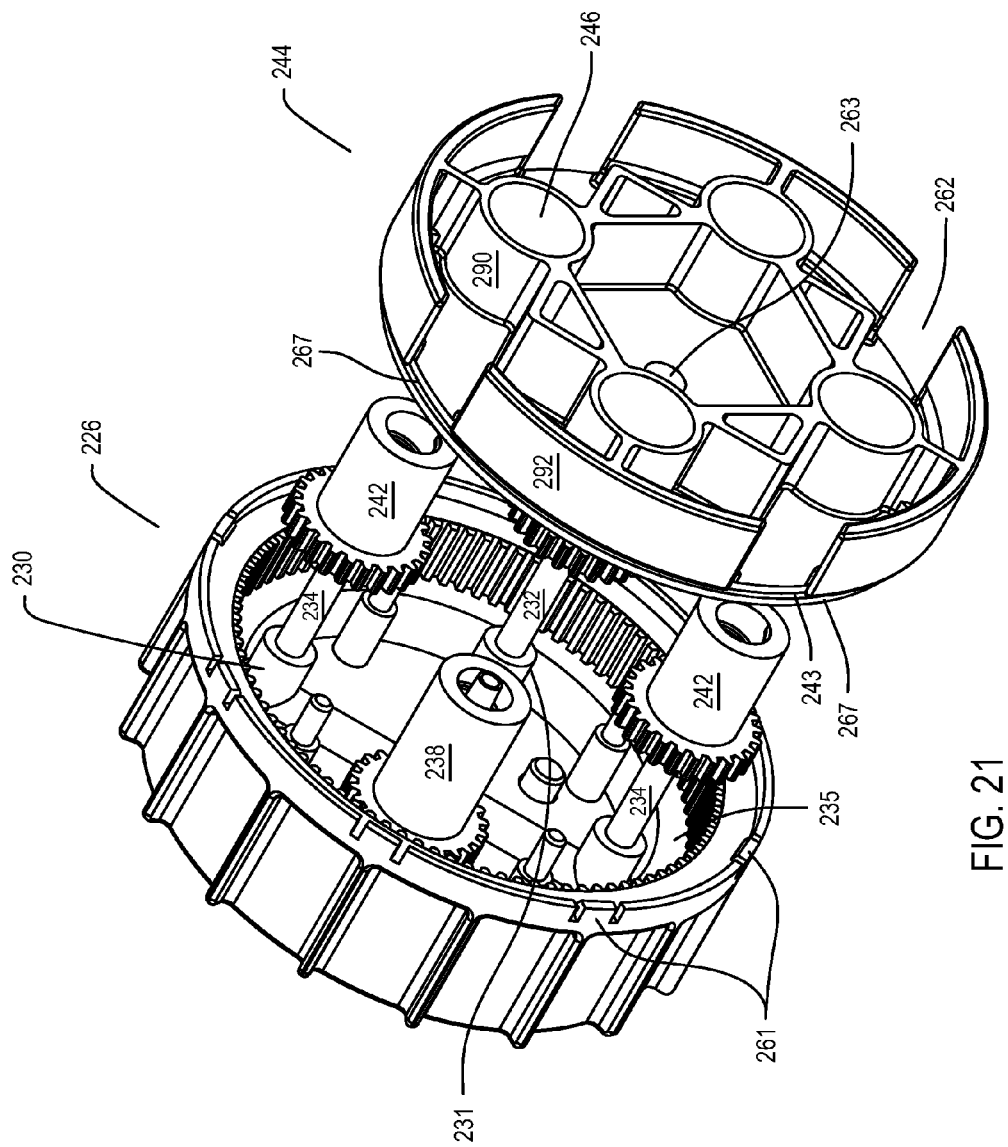
FIG. 21 is an exploded view of an alternative embodiment of the manifold where the channel body and plurality of gears are secured within the proximal and distal caps.

Proximal cap 226 is shown with a distal cap 244 in FIGS. 20 and 21. Proximal cap 226 has a base 227 and a rim 233. Rim 233 extends distally from a distal face of base 227. Rim 233 has a plurality of ribs (not identified) that are spaced circumferentially apart on an outer surface (not identified) of rim 233. Rim ribs are used for grasping proximal cap 226. Internal proximal cap rim 233 is two inner surfaces 225 and 228. Inner surface 225 is located on a proximal section (not identified) of rim 233. Inner surface 228 is located on a distal section (not identified) of rim 233. Inner surface 225 has a smaller diameter than inner surface 228. This relationship creates a lip boss 235 on a distal face of inner section 225.

A plurality of teeth 228 are disposed over rim inner surface 228, as shown in FIG. 20. Teeth 228 extend circumferentially around rim inner surface 228. An outer post 241 extends circumferentially from a distal face of proximal cap 226, as shown in FIG. 20. A plurality of spaced-apart snap features 261 is disposed along the circumference of post 241. Proximal cap 226 is integral with post 241, snap features 261 and teeth 228, and is comprised of a single piece of plastic.

Proximal cap 226 has a central channel opening 224. The diameter of proximal central channel opening 224 ranges from approximately 1 mm to 5 mm. Located off-center on the base 227 of proximal cap 226 is a locking pin opening 229. Locking pin opening 229 is configured to receive a proximal cap locking pin 223, as shown in FIG. 20. Locking pin 223 is comprised of a circular plate 254. Extending distally from the center of a distal face of pin plate 254 is a cylindrical boss 255. Extending distally further from boss 255 is a second cylindrical boss 258. Boss 258 has a diameter that is less than the diameter of boss 255. Bosses 255 and 258 and pin plate 254 are integral and are comprised from a single piece of plastic.

Figure 24:
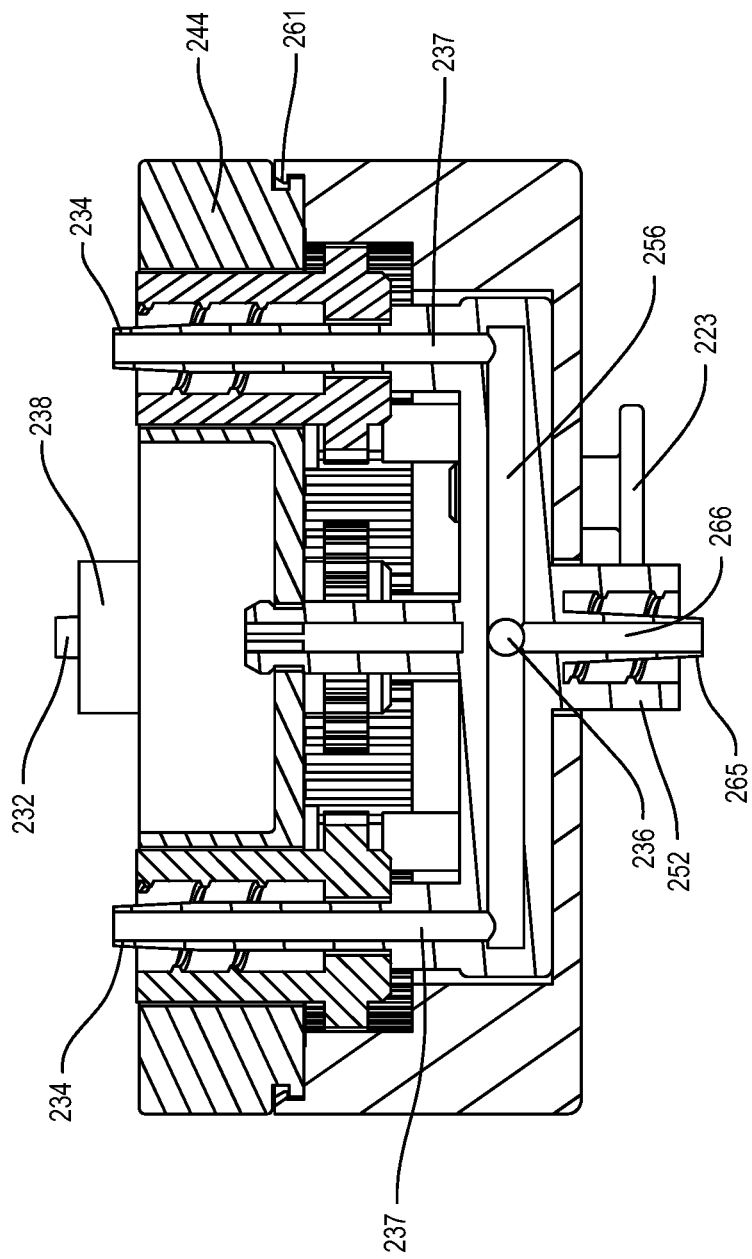
FIG. 24 is a cross-sectional view of an alternative embodiment of the manifold illustrating a continuous flow path between a central channel and a plurality of sub-channels.
Figure 25:
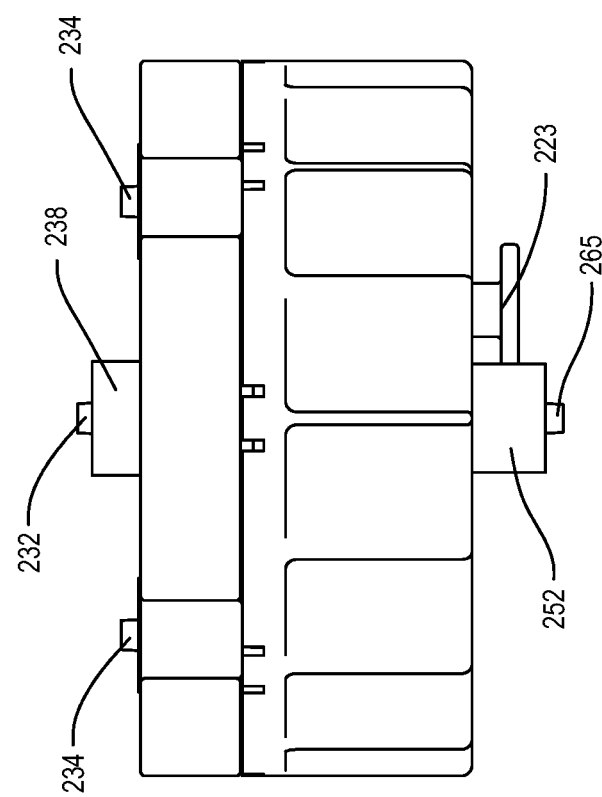
FIG. 25 is a plan view illustrating the top of an alternative embodiment of the manifold.
Figure 26:
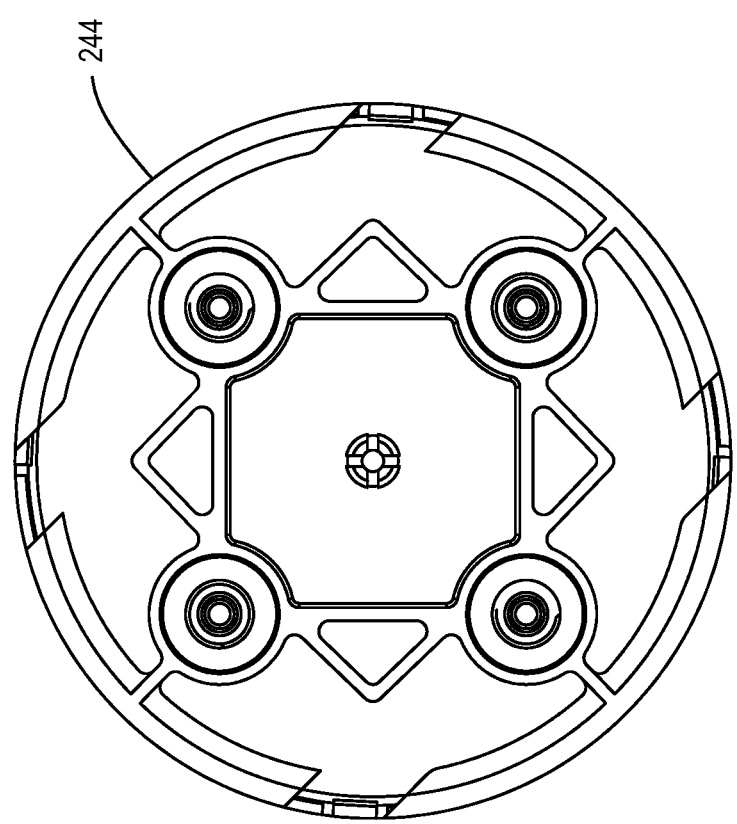
FIG. 26 is a plan view of an alternative embodiment of the manifold illustrating the distal view of the distal cap.

Circular plate 268 is distal to proximal cap 226 and is seated within proximal cap 226, as shown in FIGS. 20 and 21. Circular plate 268 is comprised of a single piece of plastic. Circular plate 268 is dimensioned to seat against proximal cap base 227. A plurality of semi-spherical ribs 236 are disposed on a distal face of plate 268. Ribs 236 extend from the center of plate 268 towards the outer edge of plate 268. Each rib 236 is formed to define a sub-channel 256, as seen in FIG. 24. A post 252 extends from a proximal face of plate 268, as seen in FIGS. 24 and 25. Post 252 is integral plate 268. Post 252 is located centrally on the proximal face of plate 268 and has a bore (not identified). Extending proximally from the base of the bore is a Luer fitting 265. Fitting 265 is centrally located on the proximal face of plate 268. Fitting 265 has an inlet opening 266. Plate inlet opening 266 leads into the rib sub-channels 256. Two cylindrical bosses 230 extend distally from a first pair of diametrically opposed ends of ribs 236. Two cylindrical bosses 231 extend distally from a second pair of diametrically opposed ends of ribs 236. Bosses 230 and 231 each have a through bore 237 that extend the length of the bosses. Two Luer fittings 232 extend distally from a distal end section of bosses 231. Two Luer fittings 234 extend distally from a distal end section of bosses 230. Both fittings 232 are equal in length and are longer than both fittings 234. Fittings 234 are equal to each other in length. The rib sub-channels 256 extend into the bores 237 of bosses 230 and 231 so as to be in fluid communication. The bores 237 of bosses 230 and 231 lead into the lumen of fittings 234 and 232, respectively, so as to be in fluid communication. All four fittings 232 and 234 are equal in diameter and are integral with circular plate 268. Fittings 232 and 234 are standard ISO Luer fittings.

As shown in FIG. 20, circular plate 268 also has four anti-rotational pegs 260 that extend distally away from the distal face of plate 268. Anti-rotational pegs 260 are comprised of a cylindrical boss 214 and a stem 215. Boss 214 extends from the distal face of plate 268. Stem 215 extends distally from boss 214. Stem 215 has a diameter that is less than that of the cylindrical boss 214. Pegs 260 are integral with circular plate 268. Pegs 260 are located near the outer edge of plate 268.

A bore 239 is located off-center on plate 268. Bore 239 is the same diameter as proximal cap locking pin opening 229.

Manifold 220 further includes a plurality of planetary gears 238 and 242. Planetary gears 238 are equal in length. Gears 242 are also equal in length. Gears 238 are longer than gears 242. Gears 238 and 242 both have an equal inner and outer diameter. In one version of this invention, the inner diameters of gears 238 and 242 are approximately equal to the outer diameters of fittings 232 and 234. Gears 238 and 242 also have teeth 240. The teeth 240 are dimensioned to engage with cap teeth 228. Teeth 240 are located at a proximal end of planetary gears. Each gear 238 and 242 has a through bore (not identified) that extends the longitudinal length of the gear. A distal section of each gear through bore is threaded. This threading is dimensioned to accept a male threaded Luer fitting.

Distal cap 244 is shown in FIGS. 20 and 21. Distal cap 244 is comprised of a single piece of plastic. Distal cap 244 has a plurality of cylindrical posts 271. In FIG. 20 two posts 271 of exaggerated height are shown for purposes of illustration. Posts 271 are located near the outer edge of the step 243. Posts 271 are located so as to correspond co-axially with anti-rotational pegs 260. Each post 271 defines a closed-end bore (not identified) that extends inwardly from the proximal end of the post. A circular step 243 extends proximally away from a proximal face of distal cap 244. Step 243 is a cylindrical boss that has a slightly smaller diameter than the diameter of the proximal face of distal cap 244. An annular groove 267 is located on step 243. Groove 267 is disposed between a proximally directed outer edge of step 243 and the proximal face of distal cap 244. Proximal cap snap features 261 seat in grooves 267 to hold the caps together.

A number of sleeves 290 extend perpendicularly away from the distally directed face of cap 244. Each sleeve 290 is formed with an opening 246. Raised ribs 292 also extend perpendicularly away from the distal face of cap 244. Ribs 292 extend between the sleeves 290 and arcuate plates 292. The diameter of distal cap opening 246 is approximately equal to the outer diameter of planetary gears 238 and 242. A central bore 263 is located centrally within distal cap 244. Arcuate plates 292 extend inwardly from the outer perimeter of cap 244. Plates 292 are arcuately spaced apart from each other so as to define a plurality of slits 262 between each pair of plates. This manifold may be shipped with the cannulae already attached. Each cannula 38 has a finger-hold 70 that extends through one of the slits 262. The presence of the surrounding plates 292 prevents the finger-hold and by extension the whole of the cannula from rotating. This prevents rotation of the cannula that could result in the cannula rotation free of the manifold 220.

Manifold 220 is assembled by slip fitting all four planetary gears 238 and 242 over fittings 232 and 234 of plate 268, respectively.

Gears 238 and 242 with plate 268 are then inserted within proximal cap 226. The outer edge of plate 268 abuts the inner surface 225 of proximal cap rim section 233. Once plate 268 is inserted within cap 226, teeth 240 of gears 238 and 242 are in registration with the teeth 228 of proximal cap 226. Shown in FIG. 22, teeth 240 of gear 238 is in registration with proximal cap teeth 228.

Distal cap 244 is next introduced to proximal cap 226 and plate 268. Plate anti-rotational pegs 260 seated within the closed-end bores of distal cap posts 271. Plate 268 and distal cap 244 are now secured together. This abutment prevents the plate 268 from rotating within the manifold 220. As the proximal cap and distal cap engage during use, anti-rotational pegs 260 serve to provide an anti-rotational effect and secondarily serve as locators to lock/align proximal cap 226 with distal cap 244.

Figure 22:
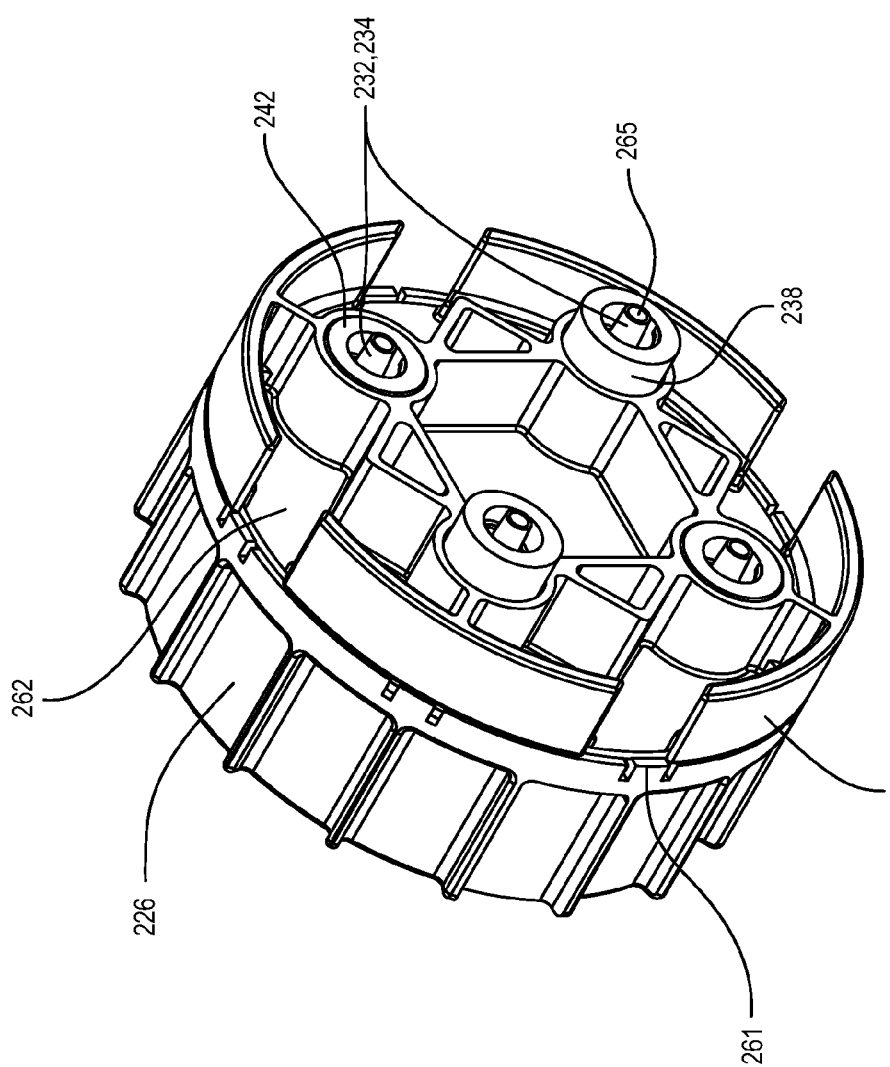
FIG. 22 is a perspective view of an alternative embodiment of the manifold illustrating four Luer fittings through a distal face of the distal cap.
Figure 23:
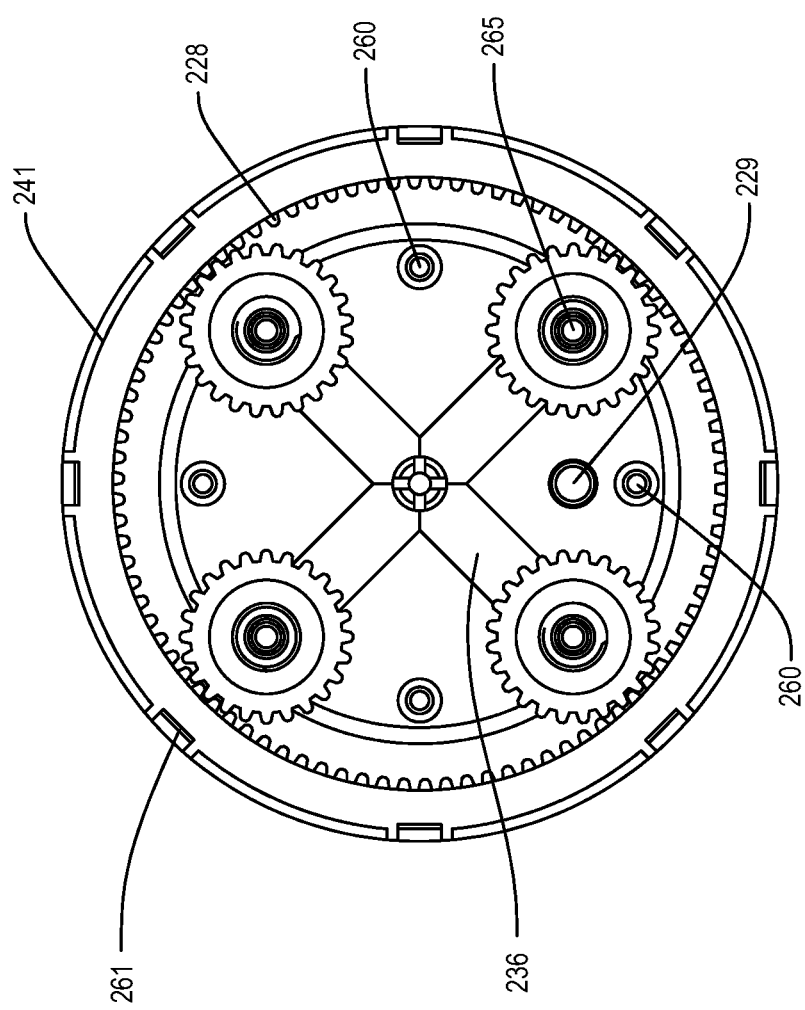
FIG. 23 is a plan view of an alternative embodiment of the manifold illustrating the channel body and plurality of gears secured within the proximal cap.

Once distal cap 244 is placed over proximal cap 226, with gear assembly and plate 268 inside, locking tabs 261 and annular groove 267 are used to seal proximal and distal caps together. A completely sealed manifold 220 is shown in FIG. 22. Manifold 220 is then introduced four cement cannulae 38 (or stylets or syringes, not identified) for simultaneous filling. All four fittings 232 and 234 have a tapered distal end. In a preferred version of the invention, fittings 232 and 234 are standard ISO Luer fittings. Cement cannulae 38 are attached to fittings 232 and 234 before filling. Each cement cannula 38 is then threaded onto complementary threaded gear distal section.

Figure 27:
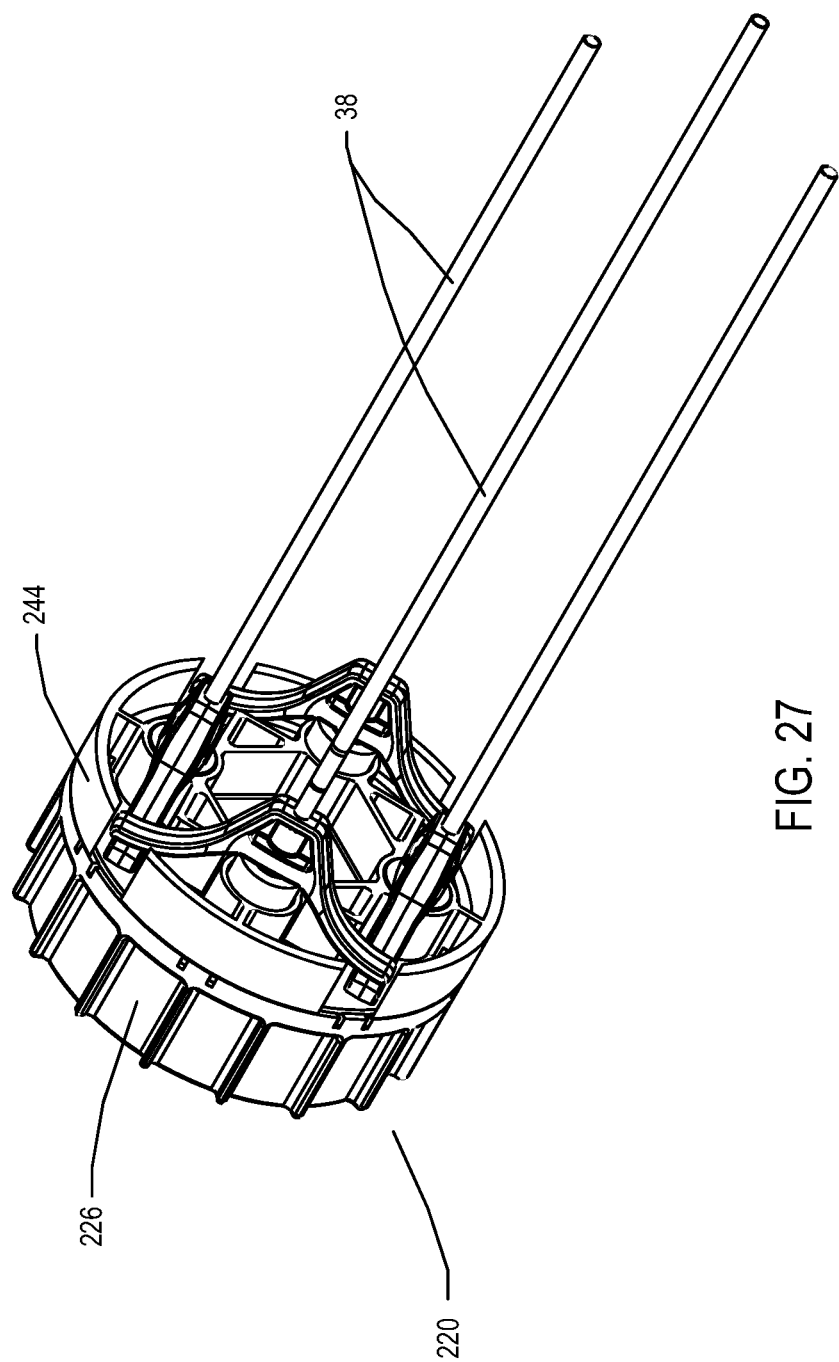
FIG. 27 is a perspective view of an alternative embodiment of the manifold with a plurality of cement cannulae attached to the manifold.

Once cement cannulae 38 are secured to manifold 220, as shown in FIG. 27, bone cement may now be injected into manifold 220 for simultaneous filling. Bone cement is then mixed and delivered using system 30. Once bone cement is mixed, it is delivered to the manifold 220 through the fitting inlet opening 266.

Bone cement consequently flows through the fitting inlet opening 266 and into each rib sub-channel 256, as shown in FIG. 24. From each rib sub-channel 256, cement flow is subsequently and simultaneously diverted to the lumen of all four fittings 232 and 234. Cement exits from the distal end openings of fittings 232 and 234 and into each respectively attached cement cannulae 38. Simultaneous filling of plural cannulae is achieved once flow is routed through manifold 220.

Once all four cannulae 38 have been filled with bone cement, the user then twists proximal cap 226 in a direction opposite that from distal cap 244 so as to rotate gears 238 and 242 along teeth 228 and 240. Once manifold 220 is rotated approximately 75 degrees, cannulae 38 are simultaneously released at once from the manifold 220. During this process tabs 261 rotate in grooves 267. Proximal cap locking pin 223 serves to prevent the user from prematurely releasing cannulae by twisting distal cap from proximal cap. Pin 223 must manually be removed by the user when simultaneous filling of cement cannulae 38 is achieved, and the user is ready for cannulae 38 to then be simultaneously released from the manifold 220. Slits 262 serve to keep cannulae 38 statically held within distal cap 244 during simultaneous release. Owing to this arrangement, when the user rotates the proximal cap 226 of the manifold 220, slits 262 aid in simultaneously releasing all four cement cannulae 38 from the fittings 232 and 234.

In the described version of the invention, as a consequence of the rotation of the proximal cap to the cannulae release position, each tab 261 has a lip that snaps into one of the slots 262 integral with the distal cap. This tab-in-slot engagement stops further rotation of the distal cap. The blocking of this rotation prevents reuse of manifold 220.

III. Second Alternative Embodiment

Figure 28:
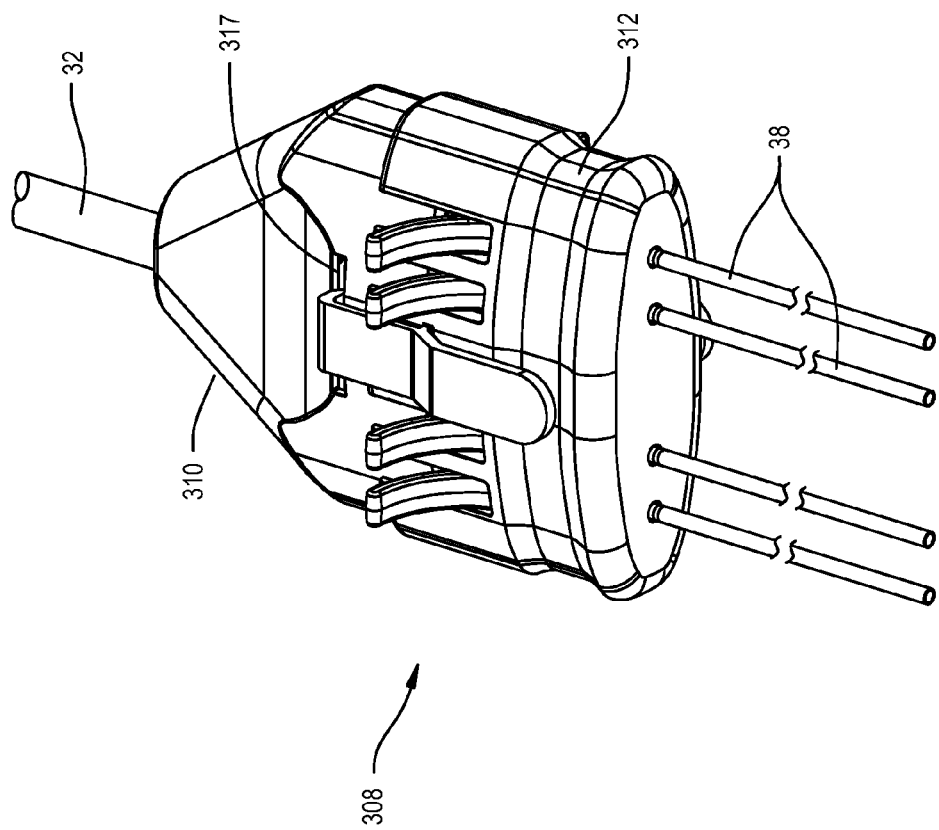
FIG. 28 is a perspective view of an alternative embodiment of the manifold with a plurality of cement cannulae attached to the manifold.
Figure 29:
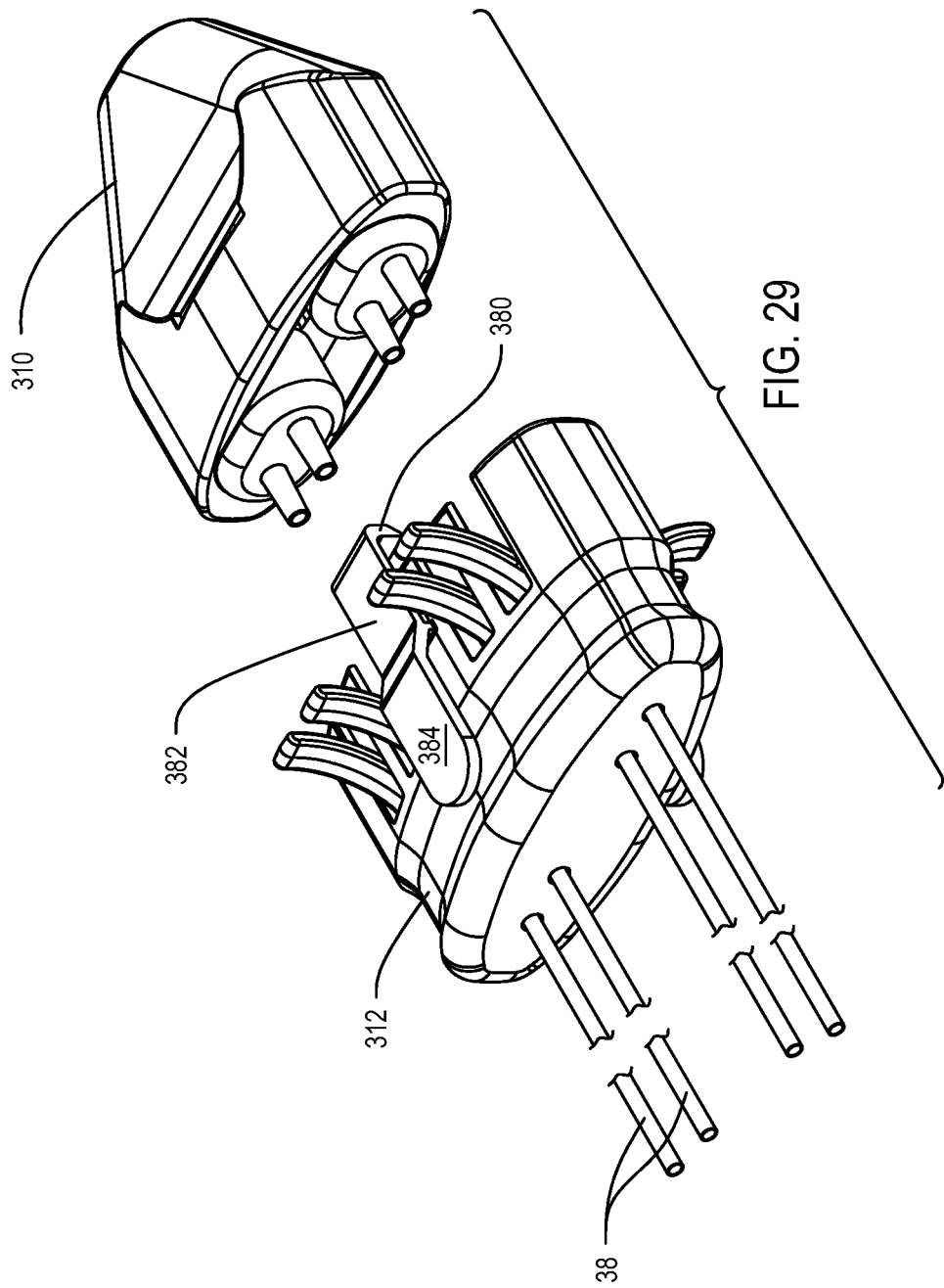
FIG. 29 is an exploded view of an alternative embodiment of the manifold illustrating a manifold housing, a plate and four attached cement cannulae.

A second alternative manifold 308 that can be part of the system of this invention is now described initially with respect to FIGS. 28 and 29. Manifold 308 includes a housing 310, a plurality of valves 336 and a cartridge 312 that is removably coupled to the housing 310. The manifold 308 is capable of simultaneously filling plural cement cannulae and subsequently simultaneously releasing said cannulae. In this version of the invention, the cartridge 312 is shaped to hold the cannulae on a flat surface, such as a table.

Figure 30:
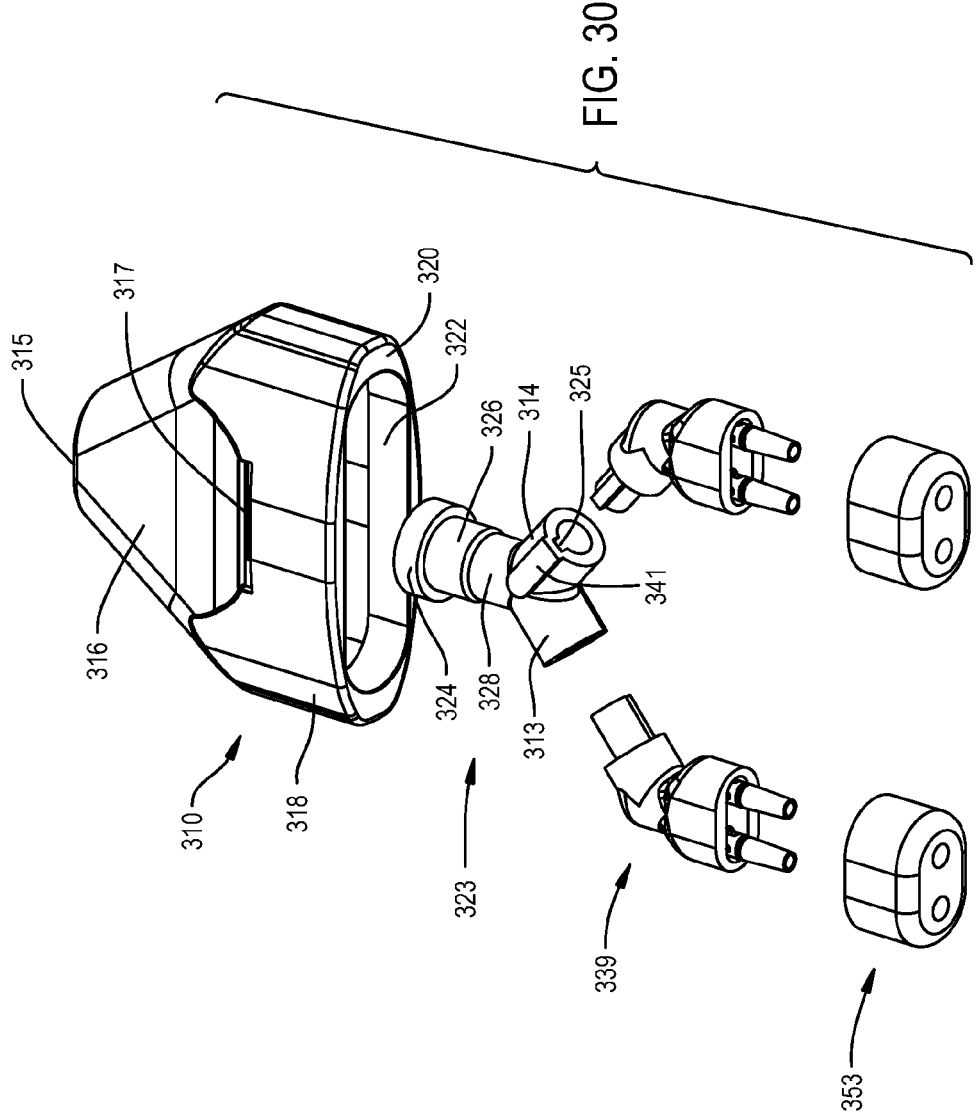
FIG. 30 is an exploded view of an alternative embodiment of the manifold illustrating the manifold housing, a Y-tube, a plurality of angled tubes, and a plurality of valve caps.

The housing 310 is a single-piece hollow structure, now described by reference to FIGS. 30 and 31, and is comprised of plastic. The housing 310 is comprised of two opposed proximal and distal sections 316 and 318, respectively. Section 316 is triangular in shape and includes a base 315 that forms the proximal end of the housing. Base 315 is formed with a center located manifold inlet opening 360. Located distally forward of base 315, internal to proximal section 316 are a plurality of tabs 319, two shown in cross section in FIG. 31, that extend radially inwardly from the outer perimeter of manifold housing inlet opening 360. Tabs 319 are located distally forward of opening 360.

Distal section 318 is elliptical in cross-sectional shape and extends distally away from housing section 316. The outer surface of the housing 310 is further formed to have two elongated grooves 317 (one groove 317 shown in FIG. 30). Each groove 317 extends laterally across the housing generally at the locations where the housing proximal and distal sections 316 and 318, respectively, meet. At the distal end of distal section 318 is an opening 322. Opening 322 is generally elliptical in shape. Internal to the housing is a void space, not identified. This void space generally has the shape of the housing proximal and distal sections 316 and 318, respectively.

Internal to the housing 310 is a Y-shaped tube 323. Tube 323 is comprised of a proximal section 324, first and second intermediate sections 326 and 328, respectively, and a pair of distal sections 313 and 314. Proximal section 324 has a larger diameter than the adjacent first intermediate section 326. First intermediate section 326 has a larger diameter than the immediately distal adjacent second intermediate section 328. Extending from the distal end of the second intermediate section 328 are the distal sections 313 and 314. Distal sections 313 and 314 extend distally and outwardly away from tube second intermediate section 328 so as to be symmetrically located relative to the common longitudinal axis through tube sections 324, 326, 328. A rib 341 extends outwardly and longitudinally on an outer surface of each distal section 313 and 314. Each distal section 313 and 314 includes a cylindrical lumen (not identified). Each distal section is further shaped to have a slot 325 that extends radially outwardly from the lumen along the length of each distal section. Slot 325 is longitudinally aligned with and extends into the respective distal section rib 341, as seen in FIG. 30. Slot 325 leads into an outlet opening (not identified) of each tube distal section 313 and 314. Extending through the entire length of tube 323 is a void space which defines a central channel 362. Tube proximal section 324 defines an inlet opening of channel 362. The open end of each lumen integral with sections 313 and 314 defines the outlet opening of each distal end branch of channel 362.

Figure 33:
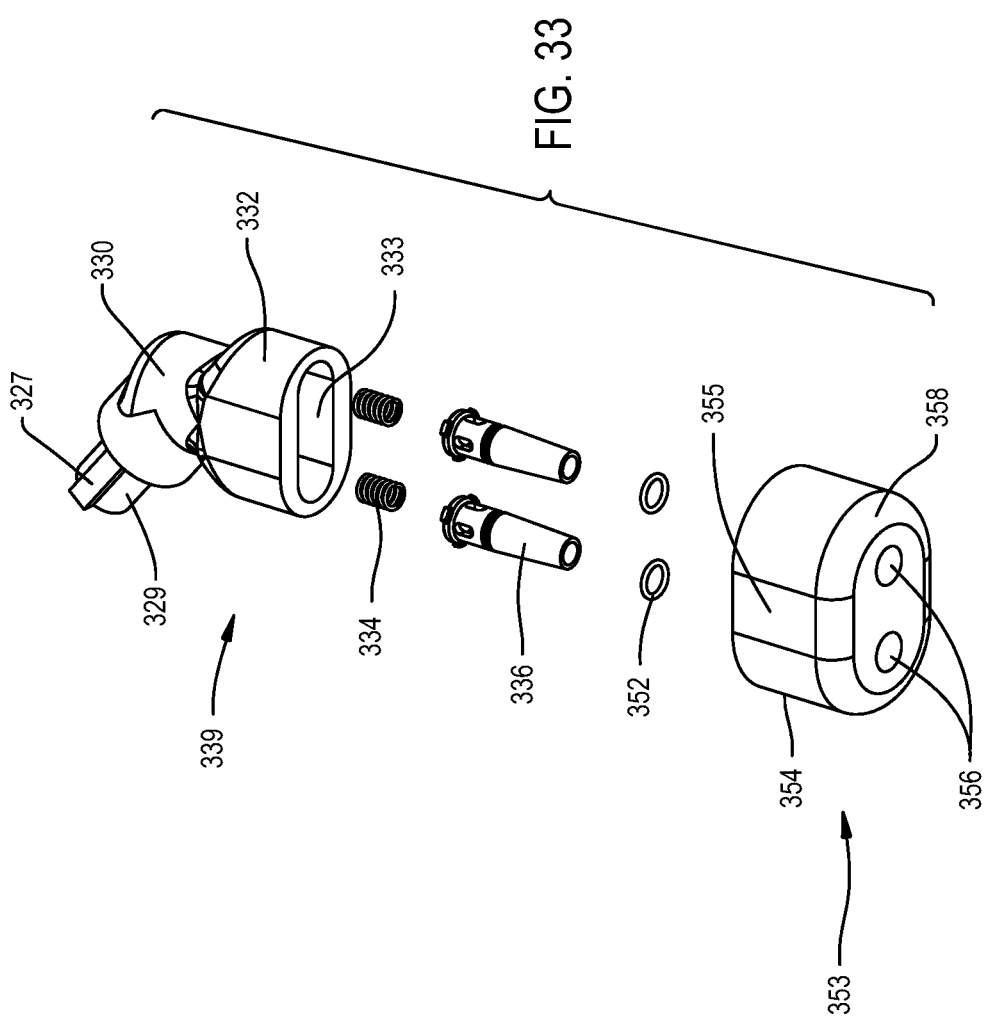
FIG. 33 is an exploded view of an alternative embodiment of the manifold illustrating the angled tube, a plurality of springs, the valves for each angled tube, an O-ring for each valve, and the valve cap.

Manifold 308 further includes a pair of angled tubes 339, now described by reference to FIGS. 30, 31 and 33. Angled tube 339 is comprised of a tabbed section 329, a middle section 330, and an oval section 332. Located on an outer surface of tabbed section 329 is a tab 327. Tab 327 extends the length of tabbed section 329. The dimensions of tab 327 are defined so as to be complementary with slot 325 of tube distal sections 313 and 314. Middle section 330 is generally elbow-shaped and has a cross-sectional area that is larger than the cross-sectional area of tabbed section 329. Tube middle section 330 extends distally away from tabbed section 329. Angled tube oval section 332 extends distally away from tube middle section 330. Oval section 332 has a cross-sectional area that is larger than the cross-sectional area of middle section 330. Oval section 332 is generally oval in shape and is comprised of two generally flat sides (not identified). Oval section 332 has an outlet opening 333. Extending through the entire length of each angled tube 339 is a pair of contiguous channels 364 and 370, as best seen in FIG. 31. Channel 364 extends from the proximally directed face of tabbed section 329 and the coaxial portion of middle section 330. Each channel 370 extends through the most forward portion of the middle section into the oval section opening 333.

Internal to the oval section 332 is a pair of proximally located walls 350. Walls 350 are located on the opposed sides of channel 370. Relative to the center axis of channel 370, walls 350 extend outwardly and distally. A post 323 extends distally away from the distal face of each wall 350 into opening 333. More specifically, a pedestal 366 extends distally away from each wall. Pedestals 366 have planar faces that are perpendicular to the longitudinal axis through oval section opening 333. Each post 323 has a cross-sectional area less than the diameter of the associated pedestal 366.

Seated over each post 323 is a spring 334. As shown in FIG. 31, spring 334 is coaxially positioned around post 323. Spring 334 is a coil compression spring and is comprised of metal or plastic. The inner diameter of spring 334 is approximately equal to the outer diameter of post 323. The proximal end of each spring rests against the distally directed face of the pedestal 366 from which the associated post 323 extends. Each spring 334 extends beyond the end of the associated post 323. In an alternative embodiment of the invention, the biasing force of spring 334 may be replicated with a gasket, a rubber fitting, a piece of foam, or a molded-in feature.

Figure 34:
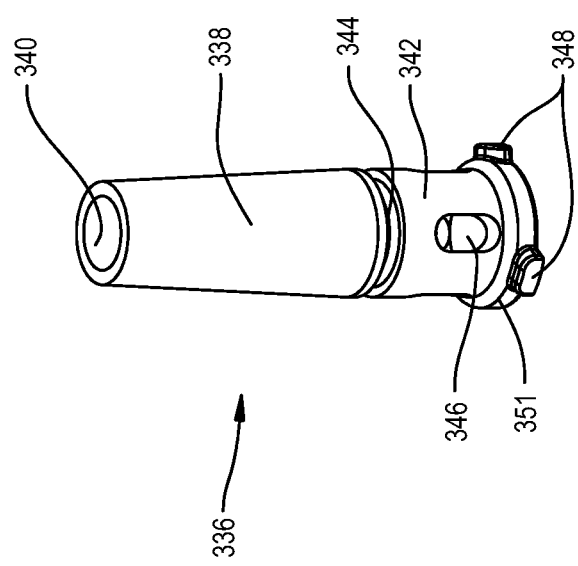
FIG. 34 is a perspective view of an alternative embodiment of the manifold illustrating a valve with circumferentially spaced apart tabs.

Manifold 308 includes a plurality of valves 336 and O-rings 352, now described by reference to FIGS. 33 and 34. Each valve 336 is a single piece component that has a core 342, a tapered male fitting 338, and a cylindrical head plate 351. Core 342 is in the form of a cylindrical tube. The valve body is shaped to have a plurality of circumferentially spaced apart inlet openings 346. Each inlet opening 346 is defined generally by an oval-shaped hole. Head plate 351 extends over and closes the open proximal end of the core 342. Head plate 351 has a diameter greater than that of the valve core. Head plate 351 has a plurality of circumferentially spaced apart tabs 348 that extend radially outward of the head. Tabs 348 have a thickness of approximately 0.5 mm to 4 mm. Male fitting 338 extends distally away from the valve core 343. Fitting 338 is tapered in that as the fitting extends away from the valve core, the outer diameter of the fitting decreases.

Between each valve core 342 and each tapered male fitting 338 is an annular groove 344. An O-ring 352 is seated in annular groove. Extending through the length of core 342 and fitting 338 is a channel 377, as seen in FIG. 31. An outlet opening 340 is located at the distal end of tapered male fitting 338 of valve 336 so as to define the outlet of channel 377. In one embodiment of this invention, valve 336 is a piston valve. In a preferred version of this invention, tapered male fitting 338 is a standard ISO Luer fitting generally found on bone cement cannulae.

A valve cap 353 extends over the distal end of each oval section 332, now described by reference to FIGS. 30, 31 and 33. In one embodiment of this invention, cap 353 is comprised of a single piece of plastic and is generally oval in shape. Each cap 353 has a body 354, a top 358 and a pair of through bores 356. Each cap body 354 has two parallel spaced apart side walls 355. Top 358 extends between side walls 355 (one identified in FIG. 33). A center wall 376 extends proximally away from a proximal face of cap top 358. Center wall 376 extends perpendicularly from side walls 355. In one embodiment of the invention, center wall 376 is thicker than each side wall. Bores 356 extend from a distal face of cap top 358 through the length of each cap 353. Cap bores 356 are approximately equal in diameter to valve core 342. Each cap bore 356 is coaxially aligned with each associated post 323.

As shown in FIGS. 6, 28, 29, 37 and 38, are previously described plural cement cannulae 38.

Figure 35:
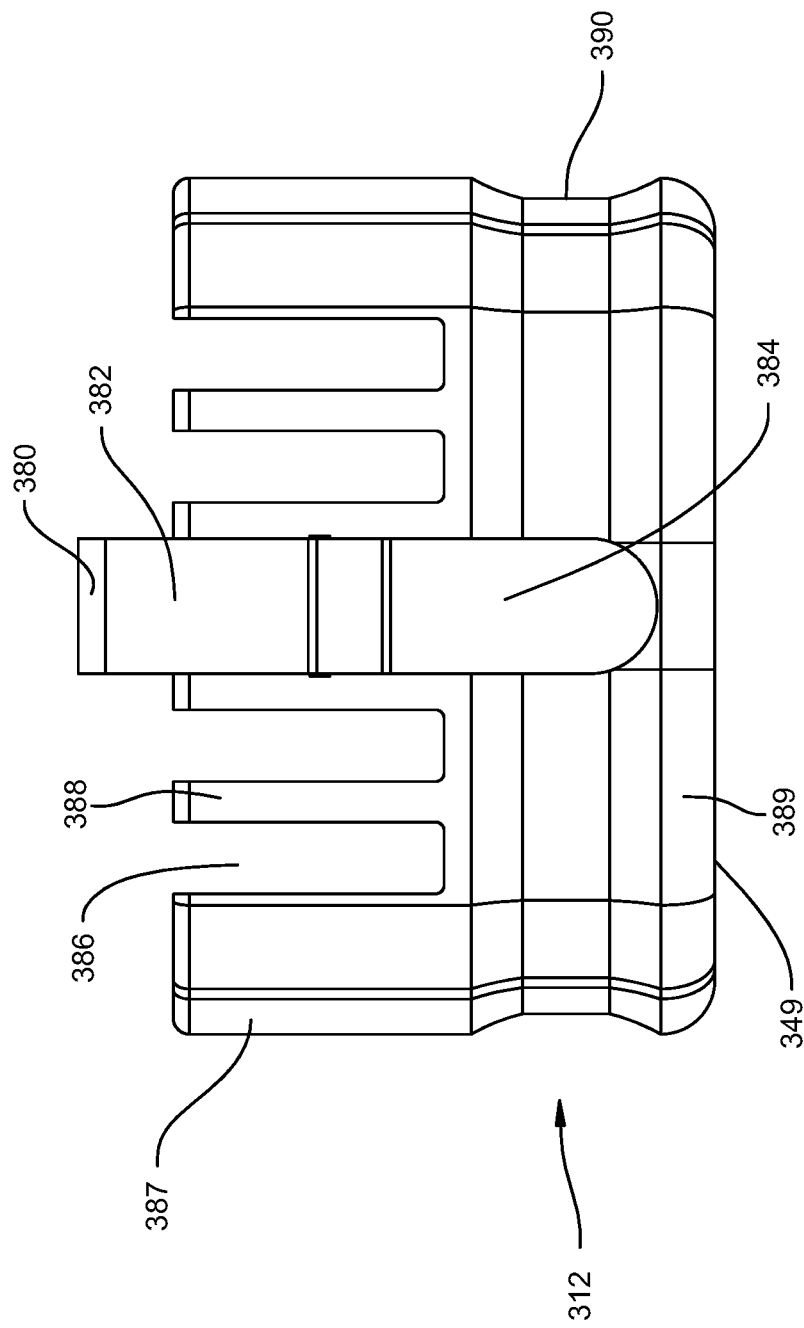
FIG. 35 is a plan view of an alternative embodiment of the manifold illustrating the plate.
Figure 36:
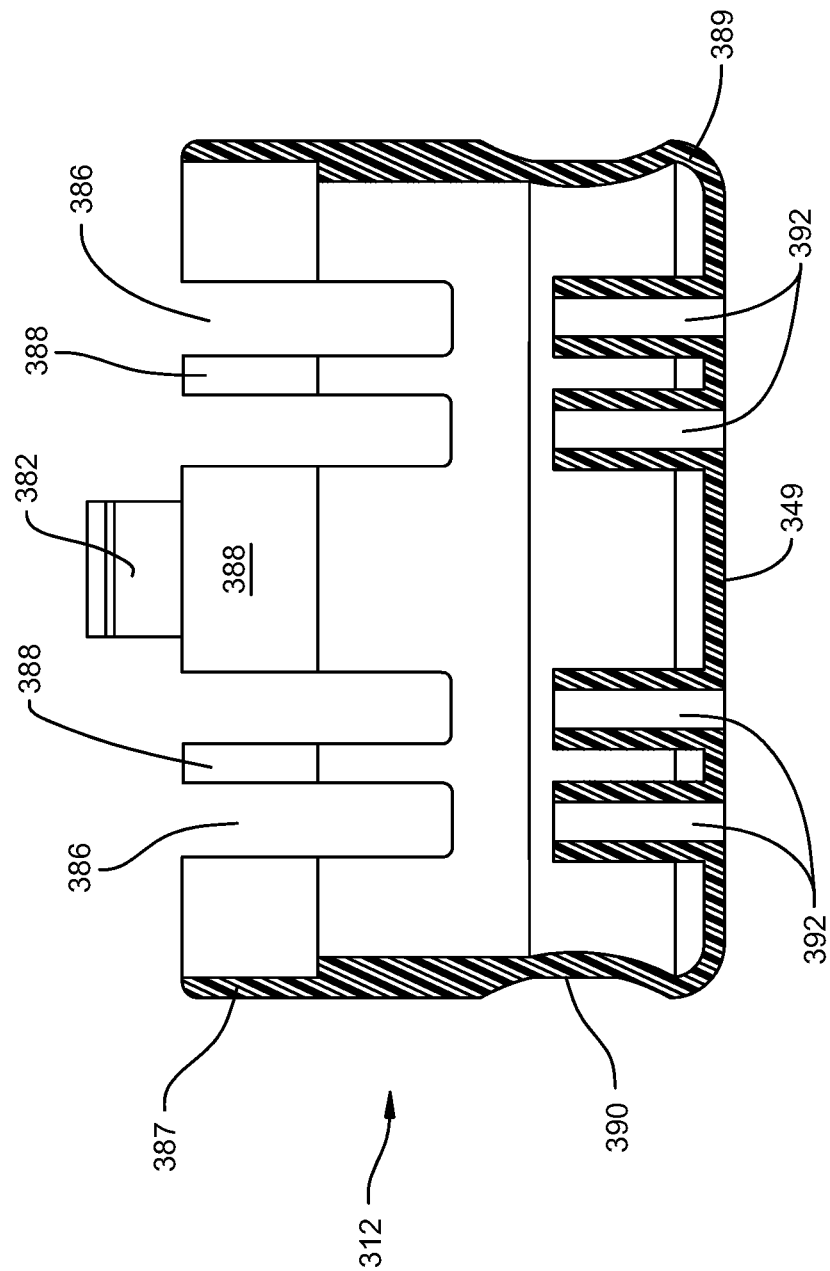
FIG. 36 is a cross-sectional view of an alternative embodiment of the manifold illustrating the plate.
Figure 37:
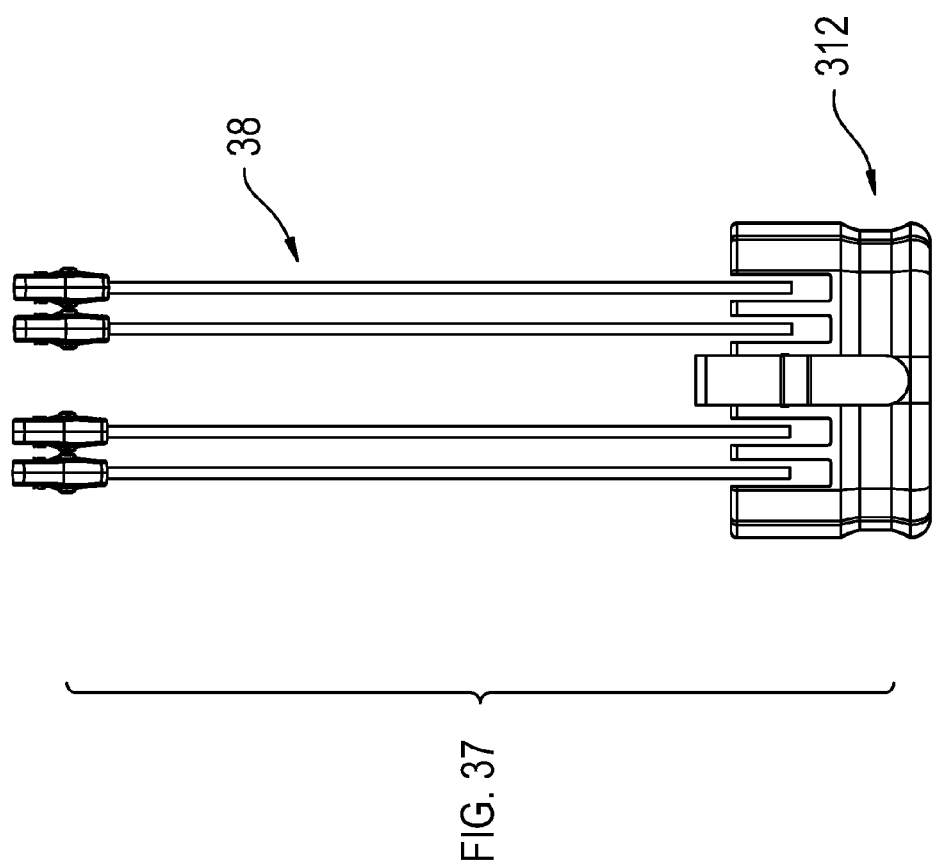
FIG. 37 is a plan view an alternative embodiment of the manifold illustrating the plate with plural removed cannulae.

Manifold 308 includes a cartridge 312, now described by reference to FIGS. 28, 35 and 36. Cartridge 312 holds the cement cannulae 38 to manifold housing 310 during filling. Cartridge 312 is generally elliptical in shape. Cartridge 312 has a head plate 349. A skirt 389 extends proximally away from the outer perimeter of plate 349. Skirt 389 is elliptical in shape and defines a recess 390. Skirt comprises a plurality of walls 387 and 388. Walls 387 are generally curved in shape and extend proximally from the associated curved sides of plate 349. Walls 388 are generally flat in shape and extend proximally from the associated flattened sides of plate 349. When manifold cartridge 312 is secured to manifold plate 310, plate walls 388 extend over manifold housing 310. Four tube-shaped posts 392 extend proximally rearwardly from the inner face of head plate 349. The center lumen of each post (lumens not identified) is dimensioned to facilitate the slip fitting of the post over the cannula tube 73. Each post 392 is spaced on cartridge 312 to correspond with, and coaxially align a separate one of the valve male fittings 338. Skirt 389 is further formed so as to have a plurality of notches 386. Four notches 386 are present in each wall 387. Notches 386 are arranged in pairs wherein one notch formed in one of the walls 388 is directly opposite a second notch formed in the opposed wall 388. The notches forming each pair of notches are located on opposed sides of a separate one of the posts. Each notch 386 extends from the proximal end of the skirt 389 approximately half the length of the skirt. The notches have a width slightly wider than the width of the cannula finger-holds.

A pair of opposed arms 382 are integrally molded with manifold cartridge 312, now described by reference to FIGS. 35 and 36. Each arm 382 is pivotally mounted to a separate one of the side walls 388. Each arm 382 has a shoulder 384 that projects outwardly above the associated side wall 388. The arm shoulder 384 is separate from the associated side wall 388 (gap between the arm and adjacent side wall not identified). Each arm 382 is able to flex relative to the associated side wall 388. A finger 380 extends from the proximal end of each arm 382. Each finger 380 extends inwardly, towards the opposed arm 382.

Manifold is assembled by inserting springs 334 coaxially over posts 323 internal to the angled tube oval section 332. O-ring 352 is seated over valve annular groove 344. Valves 336 are then seated by inserting the male fittings 338 through cap bores 356, as shown in FIGS. 31 and 33. Each cap with the valves attached is then welded on to associated tube oval section 332. This weld creates a hermetic seal so that cement cannot leak. As a consequence of the fitting of each cap and associated valves, each spring abuts a separate one of the valve heads. The spring goes into compression. The spring, consequently, biases the valve head away from the associated post and against the cap top 358. Owing to this displacement, valve tabs 348 abut the adjacent proximally directed face of cap top 358. This prevents the valve from passing through the associated cap bore. Also, as a result of this distal displacement of the valves, the valve core openings are not in fluid communication with the oval section void space 374. The valves are thus in the closed state. O-ring 352 prevents valves 336 from shifting within caps 353.

Next, angled tubes 339 are press fit with associated tube distal sections 313 and 314. Tabs 327 of each angled tube tabbed section 329 are press fit within each associated slot 325 of tube distal sections 313 and 314. This process is repeated until both tubes 339 are fitted with tube 323, as shown in FIG. 30. Angled tubes 339 are now connected to respective distal sections of Y-shaped tube 323. In alternative versions of this invention, tubes or tabs can be snap-fitted.

Next, proximal section 324 of Y-shaped tube 323 is snap-fit with manifold housing 310. Angularly spaced apart tabs 319 at base of tube proximal section 324 are then used to snap-fit tube proximal section 324 between the complementary manifold housing slots 321. Consequently, Y-shaped tube 323 along with both angled tubes 339, all four valves 336 and all four valve caps 353, are attached to manifold housing 310, as best seen in FIGS. 30 and 31. When the manifold is in this state, springs 334 press against the valves 336. Each spring 334 pushes the valve away from the oval section base 350. Caps 353 prevent the springs 34 from pushing the valves 336 out of the manifold 308. In alternative versions of this invention, Y-shaped tube proximal section 324 is secured to manifold housing 310 by using screws, fasteners, a retaining plate, heat staking, or welding.

Cannulae 38 are slip fit through respective plate openings 392. Cannulae are positioned so that those finger holds go into the notches. Cartridge 312 is then positioned so that the cannulae 38 are disposed over valve fittings 338. More particularly, so that the female fittings seat over the male fittings 338.

Figure 38:
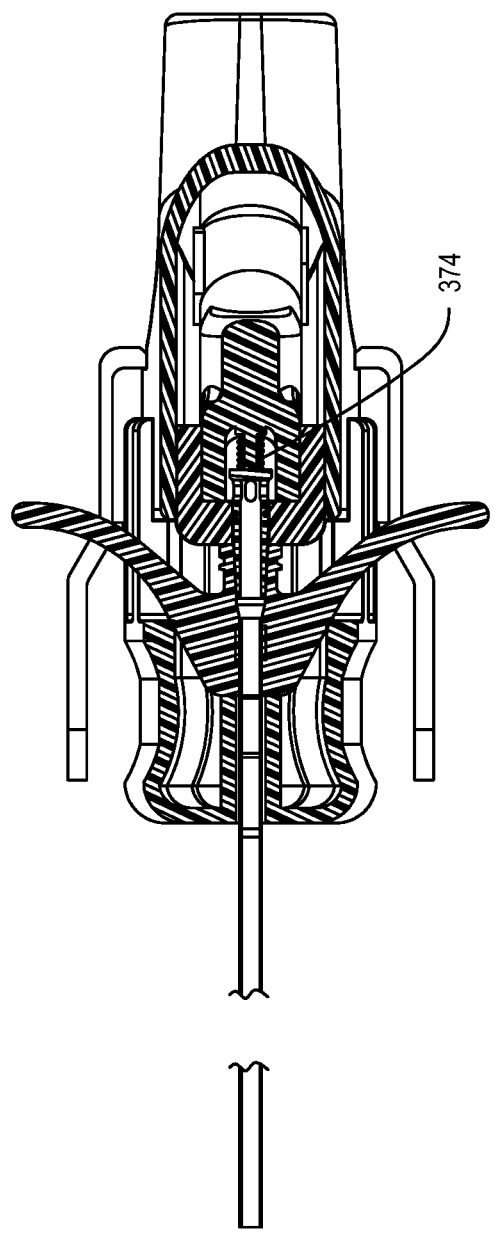
FIG. 38 is a cross-sectional view an alternative embodiment of the manifold illustrating a continuous flow path and the presence of the plate.

The continued pressing of the cartridge 312 against the manifold housing 310 overcomes the outwardly directed force that springs 334 impose on the valves 336. Each valve is pressed proximally toward the associated post 323, as seen in FIG. 38. Eventually, the valves are displaced by a sufficient distance so that each valve inlet opening 346 so that the valve core enters the void space 374. As a consequence of the repositioning of the valve core, the valve core openings are in fluid communication with the void space 374. As a result of this displacement of the valves, the valves are in the open state.

Figure 31:
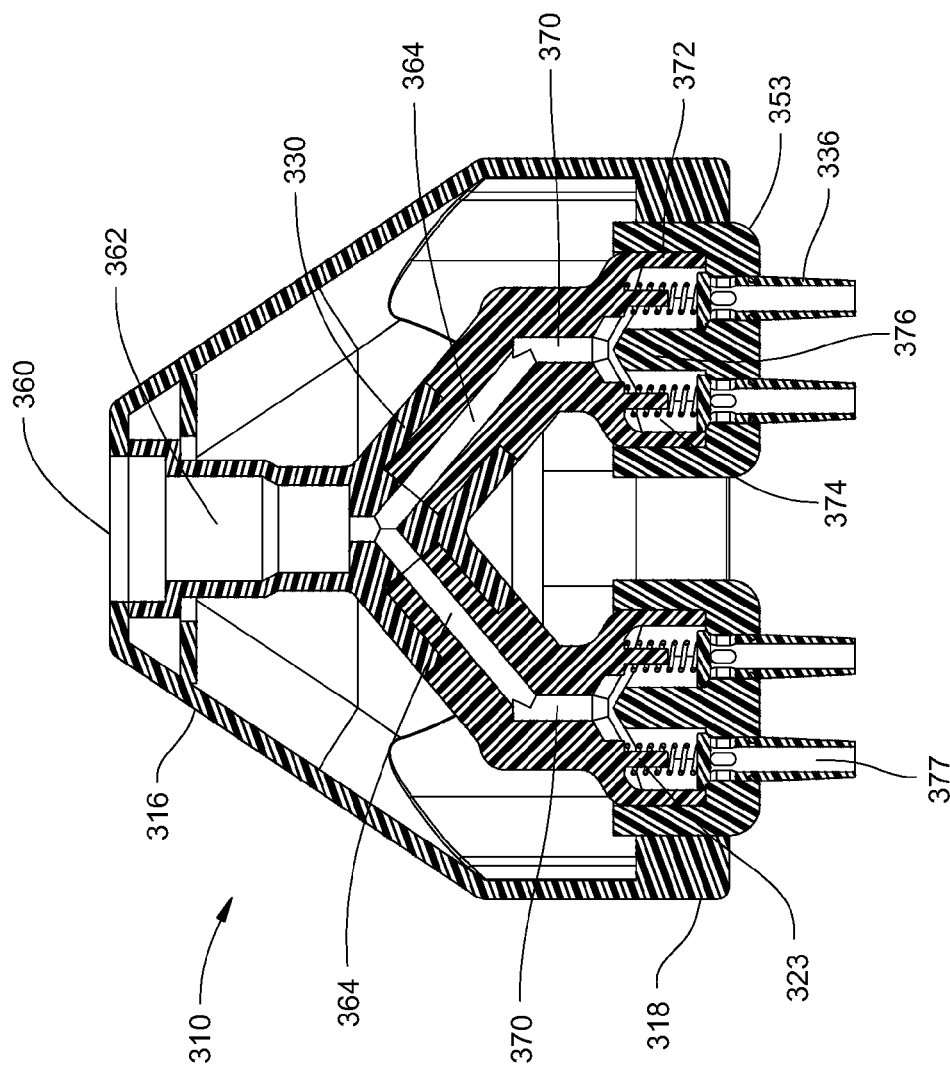
FIG. 31 is a cross-sectional view of an alternative embodiment of the manifold illustrating a non-continuous flow path and the absence of the plate.
Figure 31A:
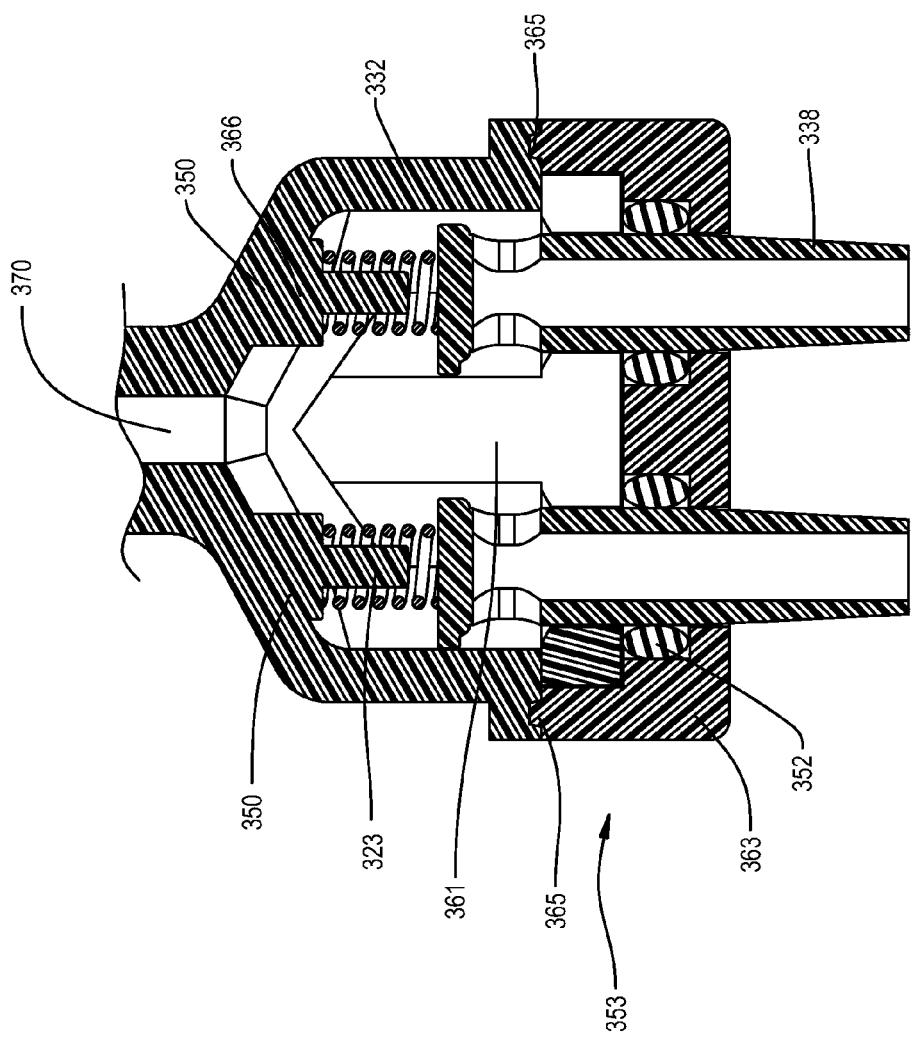
FIG. 31A is a cross-sectional view of an alternative embodiment of the manifold illustrating a two-part valve cap with an upper and lower section, and an O-ring seated within the cap lower section.
Figure 32:
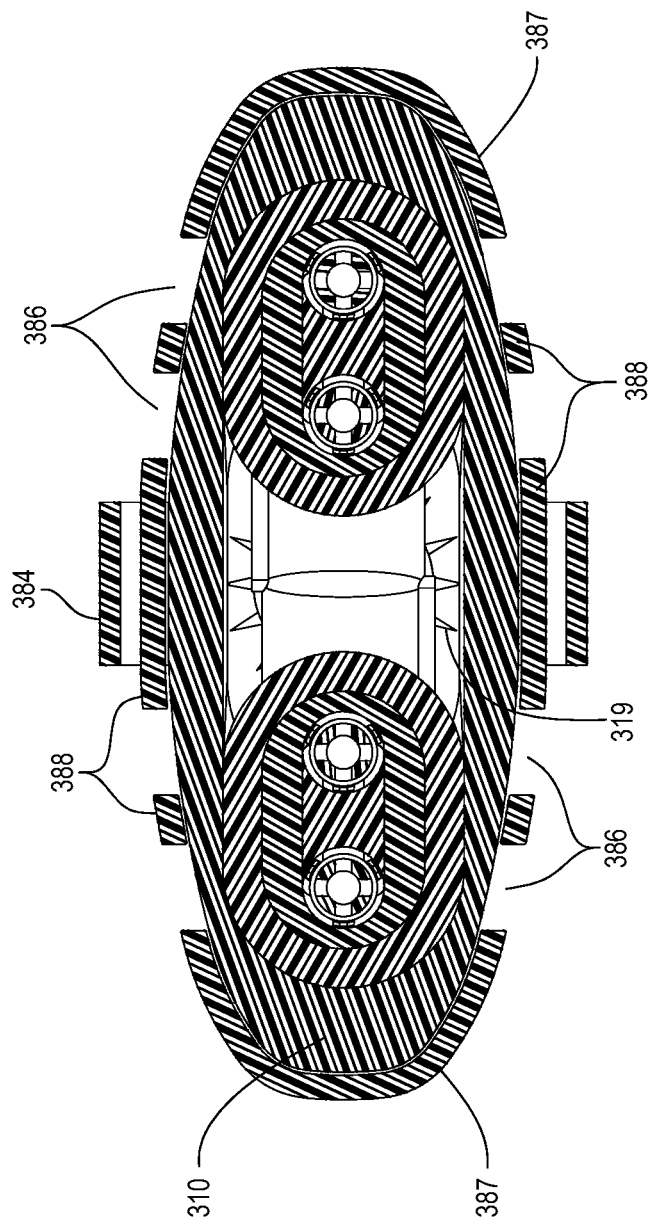
FIG. 32 is a cross-sectional view of an alternative embodiment of the manifold illustrating a plurality of valves, each valve having a plurality of tabs.

Due to the relative dimensions of the posts, valves and the cartridge, when the manifold is in the open state, there is a clearance established between the valve head plate 351 and the distal end of the post 323, clearance best seen in FIGS. 31 and 31A. This clearance substantially eliminates the likelihood that, when a valve is closed, the valve could impose a possibly damage-inducing pressure on the adjacent post.

Simultaneously, with the displacement of the valves to the open state, the fingers 380 integral with the plate arms 382 snap into the associated grooves 317 integral with the housing distal section 318. The seating of the fingers 380 in the grooves 317 blocks the force imposed by springs 344 against the valves 336 from pushing the cartridge away from the manifold housing 310. In order to facilitate this engagement of the manifold housing fingers 380 with the cartridge 312, it may be necessary to press inwardly on the shoulders 384 in order to pivot the fingers outwardly.

Once each male fitting 338 is seated within the complementary female fitting 69, a continuous flow path from each valve opening 340 into the female fitting is established.

The assembled manifold 308 is attached to the proximal end of delivery tube 32, as shown in FIG. 28. More specifically, the delivery tube 32 is seated in the proximal end inlet opening 360. Bone cement is mixed in chamber 283 using paddle 284 of FIG. 1C. Bone cement flows from tube 32 of the mixing and delivery system 30 into the proximal end inlet opening 360 of central channel 362. Cement advances distally forward through the central channel 362 of Y-shaped tube and into associated sub-channels 364, as shown in FIG. 31. Cement flows from each sub-channel 364 into the associated sub-channel 370. Cement flows through sub-channels 370 into the void space 374. FIG. 38 illustrates the open state of valves 336.

Since the valve core openings 346 are disposed within the void space 374, the cement then flows through the openings and into the associated valve channel 377. The cement then flows from each valve channel 377 into the lumen of each attached associated cannula 38. Due to pressure exerted by user from the delivery device, cement travels simultaneously through the cannulae lumens until each cannula 38 is filled.

Once cement has simultaneously filled plural cement cannulae 38, the user un-clips the cartridge 312 from the manifold 308 by depressing the shoulders 384 inwardly. This results in the arm fingers 380 pivoting away from elongated groove 317. The cartridge 312, with the cannulae 38 attached, is then pulled away from the manifold 308 as seen in FIG. 29. The cement-filled cannulae are individually withdrawn from the plate for use.

Upon the removal of the cartridge 312 from the housing 310, the force that the cannulae 38 impose on the valves is removed. Springs, therefore, return valves to the closed state. This substantially eliminates drip of cement out of the end of the housing.

Manifold can also be used fill just one, two, or three cannulae. If less than four cannulae are required, then only the one, two or three cannulae are attached to the cartridge 312. When the partially loaded cartridge is attached to the housing, the valve(s) adjacent the unloaded spaces of the cartridge are not urged into the open state. Consequently, when cement, which is under pressure, enters the void spaces adjacent these valves, the cement presses against the valve head plates. There is no cement flow out of these valves.

Once cartridge 312 is pulled away from the manifold 308, cartridge 312 carries the cement-filled cannulae. Owing to the design of cartridge 312, cartridge 312 is capable of resting on an even surface, such as an operating room table, so that a user may remove a cannula from the plate as needed.

In another version of this embodiment of the invention, the valve cap 353 is comprised of two separate pieces of plastic, now described by reference to FIG. 31A. Cap 353 is comprised of an upper section 361 and a lower section 363. A molded-in snap feature 365 extends proximally away from an outer edge of the cap lower section 363. Feature 365 is used to fasten lower section 363 with oval section 332. In a preferred version of this invention, lower section 363 is welded to oval section 332. Cap upper section 361 is now constrained between cap lower section 363 and oval section 332. Each cap section 361 and 363 has bores 356 through which each associated valve extends. Each cap bore 356 is coaxially aligned with each associated post 323. In this version of the invention, each O-ring 352 is now seated in a different location. O-ring 352 is now seated between the outer face of tapered male fitting 338 and cap lower section 363. This arrangement of the O-ring 353 prevents the male fitting 338 from rotating or shifting with either cap upper or lower section. O-rings, in all embodiments of this invention, act to prevent cement leakage.

Similarly, in some versions of the invention, there may not be a need to provide a spring or other biasing member to hold the valves 336 closed. This is because cement within the manifold void space 374 pushes the valve head plate 351 distally forward. Consequently, cement cannot access valve core openings 346 and valve channels 377. The force of the cement flow thus holds the valves in the closed state.

IV. Third Alternative Embodiment

Figure 39:
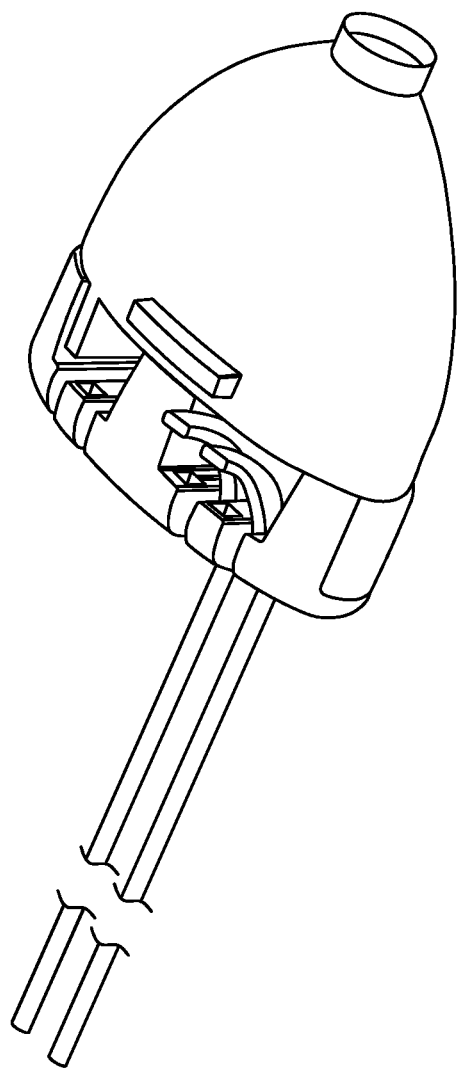
FIG. 39 is a perspective view of an alternative embodiment of the manifold used with the mixing and delivery system.
Figure 40:
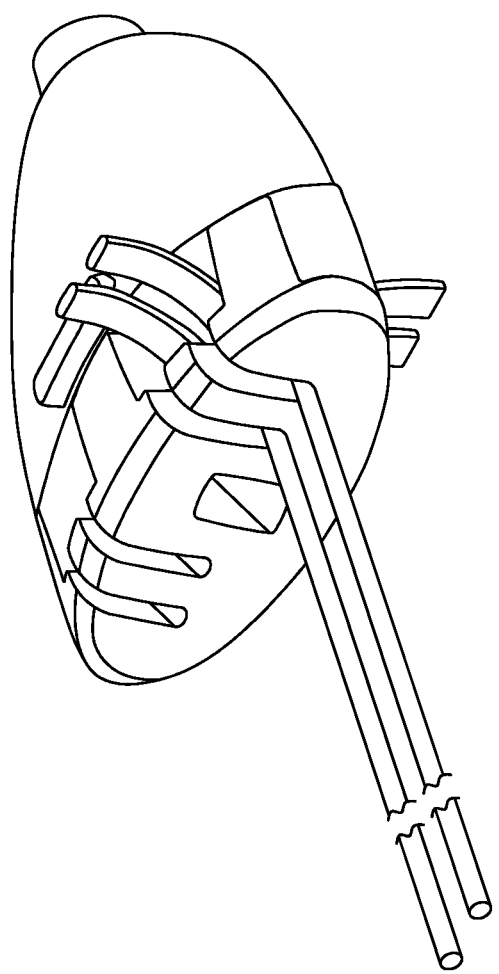
FIG. 40 is a perspective view of an alternative embodiment of the manifold used with the mixing and delivery system.

FIGS. 39-40 illustrate an additional alternative manifold assembly that can be used as part of the system of this invention. This manifold assembly includes a housing and cartridge similar in shape and function to the housing 310 and cartridge 312 of previously described manifold 308.

In this embodiment of the invention, the cartridge is moveably secured to the housing. More specifically, posts extend outwardly from the housing. These posts seat in complementary bores in the cartridge. This posts-in-bores arrangement allows the cartridge to slide relative to the housing.

A post extends proximally rearwardly from the cartridge. This post extends into the housing. Internal to the housing is a lock plate (not illustrated). This lock plate has a keyhole shaped opening through which the cartridge post extends. The lock plate is biased so that the small width portion of the plate opening seats in a groove formed in the post. A spring, not illustrated, internal to the housing, performs this biasing function. The spring thus holds the lock plate in the locked position. This seating of the plate against the post holds the cartridge against the housing. A release button integral with the lock plate extends beyond the outer wall of the housing. The release button is depressed to move the locked plate from the locked position to the release position. When the lock plate is in the release position, the wide diameter portion of the plate opening is positioned around and away from the cartridge post. Since the lock plate is spaced from the post, the cartridge can be moved away from the housing.

At the distal end of the manifold post, there is a head, not illustrated. This head has a diameter wider than that of the widest diameter portion of the lock plate opening. When the cartridge is moved distally relative to the housing, this head abuts the proximally directed surface of the lock plate. This head-against-plate abutment is what prevents the complete separation of the cartridge from the housing.

The cartridge is formed with a set of notches. The notches, which are equal in number to the housing valves, extend inwardly from one face of the manifold. The width across these notches allows the cannulae tubes to be seated in the notches. The cartridge is formed so that when each cannula tube is seated in the notches, the associated cannula female fitting will be in registration with the complementary male fitting of the adjacent valve. The cartridge may also be formed with features to facilitate the snap fitting of the cannulae in the notches. This minimizes the likelihood that the cannula/cannulae will inadvertently fall out of the notch/notches.

This manifold is prepared for use by positioning the cartridge in its most distal position relative to the housing. The cannulae are fitted in the notches. The cartridge is then slid against the housing. This displacement of the cartridge results in the like displacement of the cannula/cannulae. This displacement of the cannulae urges the housing valves to their open positions. The lock plate then snaps over the cartridge post to hold the cartridge and cannulae in position.

Once the cannula or cannulae is/are filled with cement, the user depresses the release button. Cartridge is then moved forward to allow removal of the cement filled cannula/cannulae.

A benefit of this version of the invention is that it minimizes the number of loose components forming the cannulae filling system of this invention.

V. Fourth Alternative Embodiment

FIGS. 41-48 illustrate an additional alternative manifold assembly 408 that can be used as part of the system of this invention. This manifold assembly 408 includes a housing 410 and a cartridge 420 similar in shape and function to the housing 310 and cartridge 312 of previously described manifold 308. This manifold assembly 408 is capable of simultaneously filling plural cement cannulae and subsequently simultaneously releasing said cannulae. Cartridge 420 holds plural filled cannulae upon filling. In this version of the invention, the cartridge 420 is shaped to hold the cannulae on a flat surface, such as a table.

Figure 41:
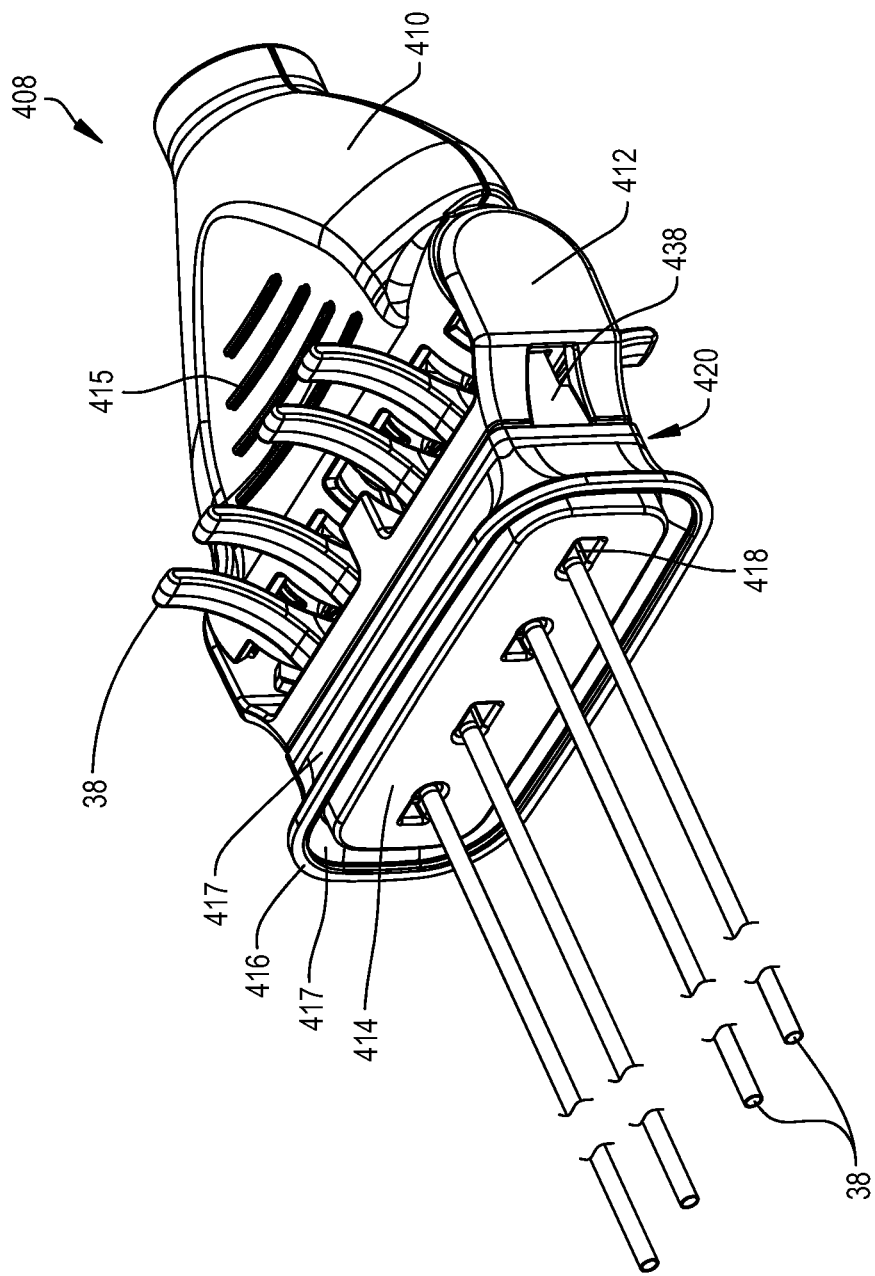
FIG. 41 is a perspective view of an alternative embodiment of the manifold with a plurality of cement cannulae attached to the manifold.
Figure 42:
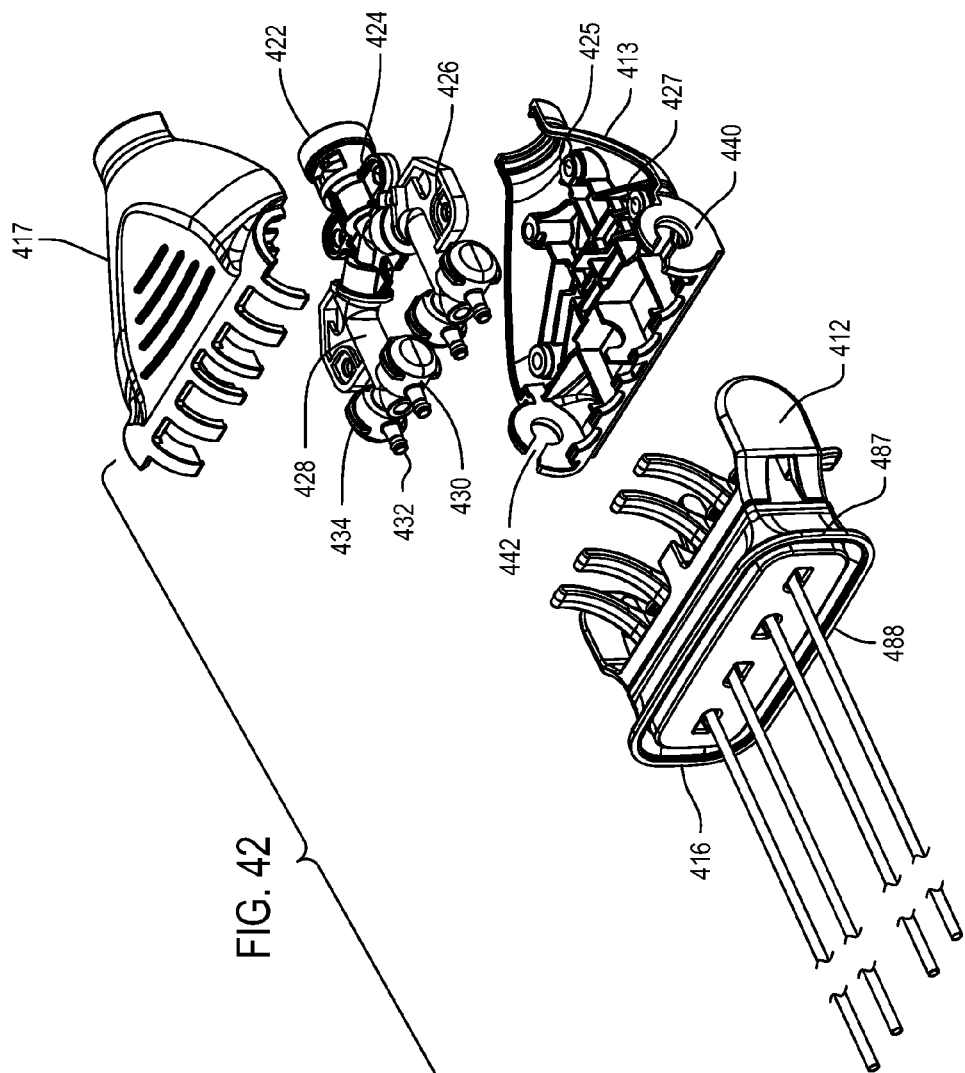
FIG. 42 is an exploded view of an alternative embodiment of the manifold illustrating a manifold housing, a cartridge and a plurality of valves.
Figure 43:
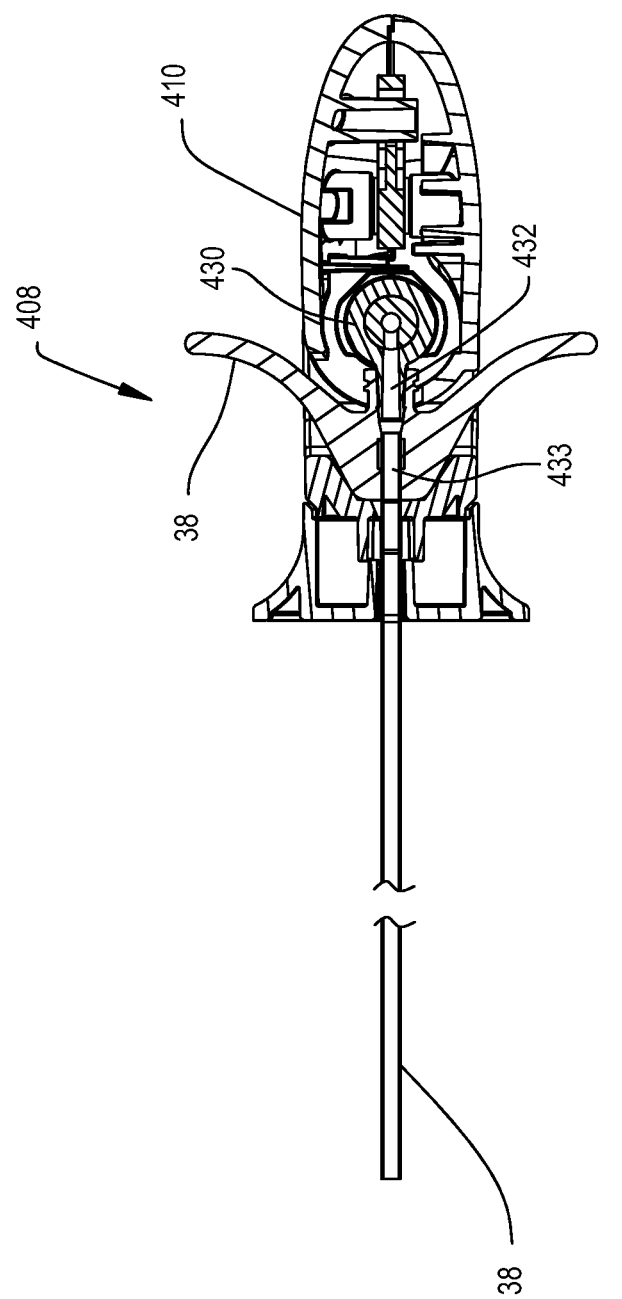
FIG. 43 is a plan view of an alternative embodiment of the manifold.
Figure 43A:
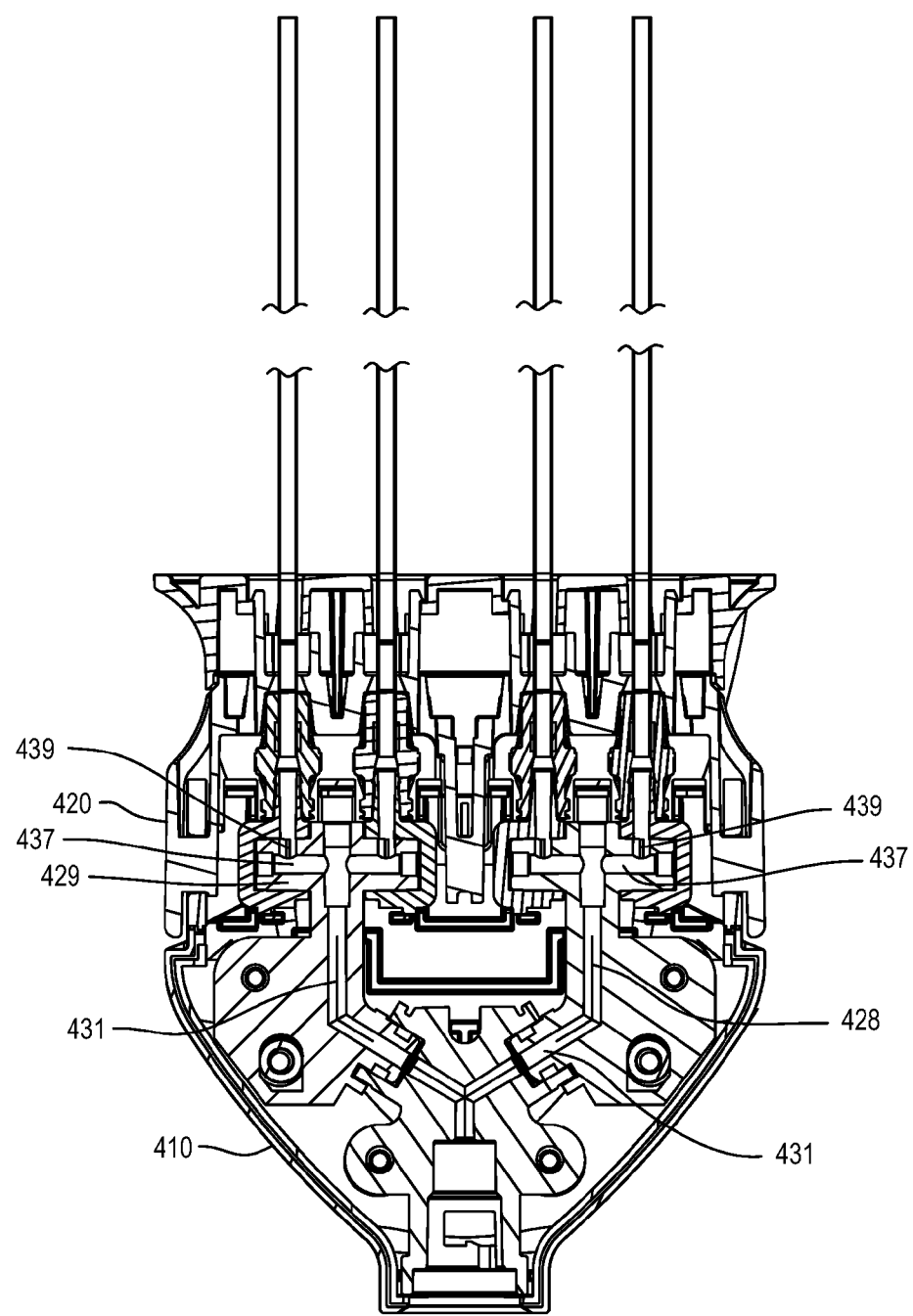
FIG. 43A is a cross-sectional view of an alternative embodiment of the manifold.
Figure 46:
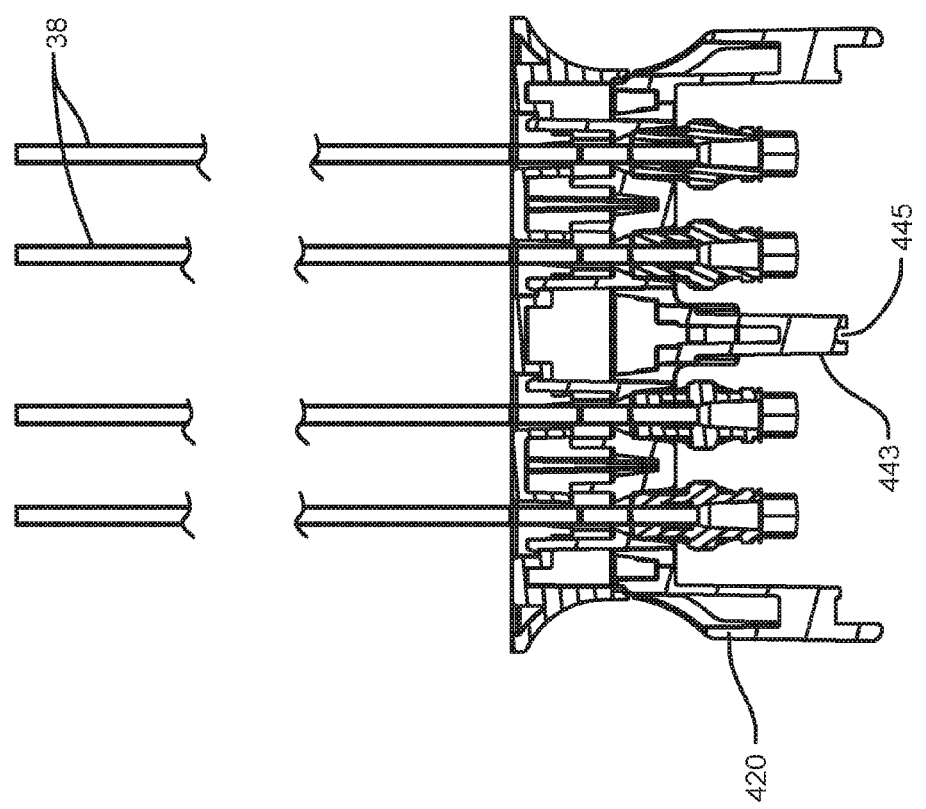
FIG. 46 is a cross-sectional view of an alternative embodiment of the manifold.

In this embodiment of the invention, the manifold housing 410 is similar in shape and function the manifold housing of the previously described manifold 308. Manifold housing 410 is comprised of a shell that is generally triangle-shaped, as shown in FIG. 41. Manifold housing 410 is comprised of an upper shell 417 and a lower shell 413, as shown in FIG. 42. Finger-grips 415 are located on opposed sides of housing shell 410 so that a user may grip the manifold housing 410. An inlet opening 422 defines a proximal end opening into housing 410. Manifold housing 410 includes a plurality of tubes 428 configured similarly to the tubes 323 and 329 of manifold 308. The flow path of bone cement or a similar substance travels along a "Tri-Y" shaped flow path, as shown in FIG. 43A. Each tube has a lumen 431 in which bone cement travels. Lumens 431 are similar in shape and function to the central channel 362 and associated sub-channels 363 of previously described manifold 308, as shown in FIG. 31. A plurality of tabs 424 and 426 extend outwardly from opposed sides of tubes 428, as shown in FIG. 42. Fasteners, not identified, extend through tabs 424 and 426 into complementary bosses 425 and 427, respectively, formed in the housing lower shell 413.

A pair of opposed bosses 429 extend perpendicularly outwardly from the ends of each tube 428. The longitudinal axis of the bosses 429 that extend outwardly from each of the tubes 429 are coaxial. Each boss 429 has a bore 437, (one identified), that extends from the lumen of the associated tube. The outer end of each bore 437 is closed. Each boss 429 is further formed to have an outlet opening 439, (one identified,) that extends radially outwardly from the bore 437. Outlet openings 439 are parallel with the inlet opening 422.

A plurality of fittings 432 are attached to the distal end openings of housing tubes 428, shown now with reference to FIG. 42. Each fitting 432 defines a lumen (not identified). Each fitting 432 extends from a cap like head 430. Disposed on a distal end of each fitting 432 is a barb 433. Barb 433 is a circumferential boss that extends radially outwardly from the outer surface of fitting 432. A ring 453 extends radially outwardly from said barb 433, said ring used to create a point of contact when said fitting is seated within the lumen of said attached cannula. Each head 430 has a rib 434 that is located on a top section of the fitting. Rib 434 extends arcuately along a top curved surface of the fitting 430. When the manifold is assembled, the ribs abut interior surfaces of the housing 410. Ribs 434 prevent the heads 430 from being ejected out of the manifold housing 410 due to pressure exerted during the filling of cement cannulae.

Each head 430 rotates around one of the bosses 429. Depending on the orientation of fitting 432, the lumen of the fitting 432 is or is not in fluid communication with the outlet opening 439 of the boss 429. Each head 430 and fitting 432 collectively function as a valve.

Disposed on opposed sides of the distally directed end of the manifold lower shell 413 are plates 440. Plate 440 is integral with manifold lower shell 413. Each plate 440 includes a slot 442. Each slot 442 has a closed end at the center of the associated plate 440. This closed end is circular in shape and has a diameter greater than the width of the portion of the slot 442 that leads to the center of the plate 440. This arrangement allows the cartridge 420 to rotate around plates 440.

Manifold 408 further includes cartridge 420, now described by reference to FIGS. 41, 42 and 44. Cartridge 420 holds the cement cannulae 38 to manifold housing 410 during filling. Cartridge 420 is generally elliptical in shape. Cartridge 420 has a head plate 414. A skirt 416 extends radially outwardly from the outer perimeter of head plate 414. Skirt 416 is elliptical in shape and defines a recess 417. Skirt 416 comprises a plurality of shallow walls 487 and 488. Walls 487 compose the associated curves sides of skirt 416 and are generally curved in shape. Walls 488 compose the associated flattened and elongated sides of skirt 416 and are generally flat in shape. Skirt 416, comprised of walls 487 and 488, is used to provide cartridge head plate 414 with additional surface area so that cartridge 420 may rest on a table vertically, and parallel with respect to gravity. Walls 487 of skirt 416 are elongated and flattened so that cartridge 420 may alternatively rest on a table horizontally and perpendicular with respect to gravity. In either positioning of the cartridge 420, filled plural attached cannulae may be easily removed from the cartridge 420.

Figure 47:
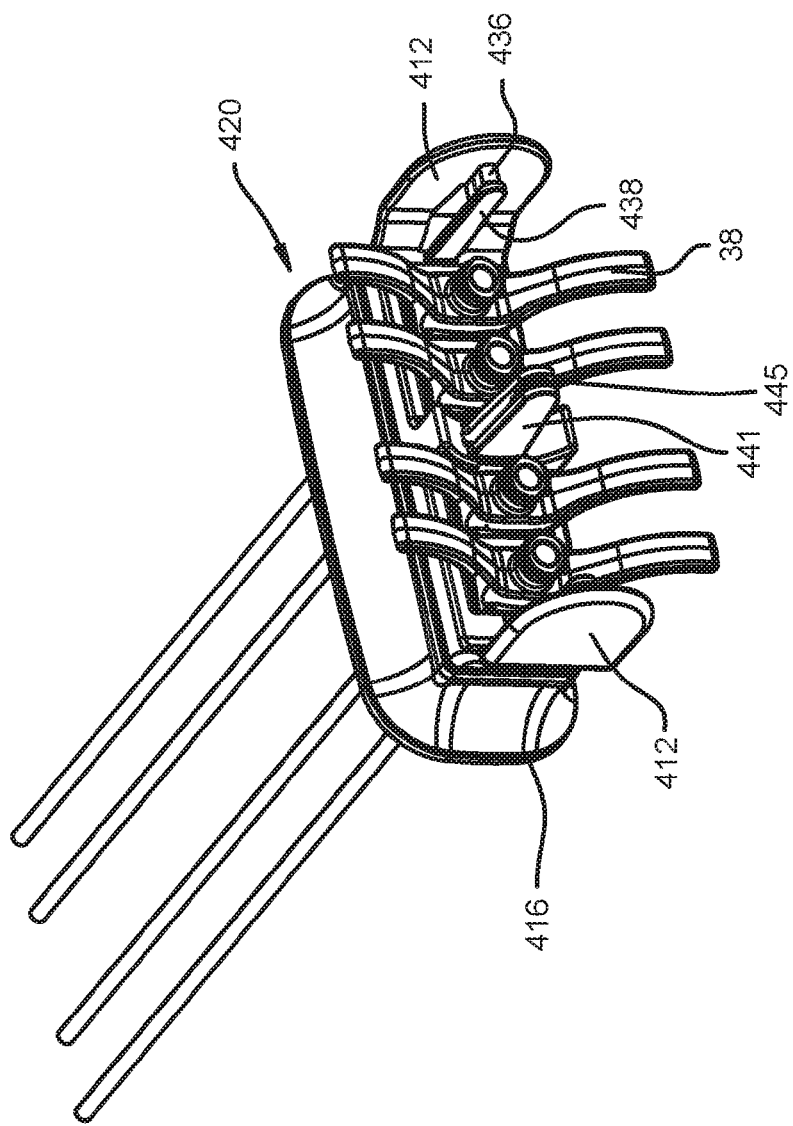
FIG. 47 is a perspective view of an alternative embodiment of the manifold.

Cartridge 420 is moveably secured to a housing 410. More specifically, a pair of opposed posts 412 extend proximally outwardly from a base 414 of cartridge 420. Attached on an inwardly directed surface of each post 412 is a tab 436, as shown in FIG. 44. Attached to the opposed side of tab 436 is a rib 438. Rib 438 is used for strengthening the post 412 and to also trap each tab 436 between the rib 438 and associated post 412. Also extending proximally outwardly from a center of cartridge 420 is a middle post 443, as shown in FIG. 47. Middle post 443 is comprised of two side walls 441 (one side wall identified in FIG. 47). Disposed between side walls 441 of post 443 is a tab 445. Tab 445 is spaced inwardly from the outer edge of post 443 to create a grooved recess (not identified). Tab 445 is located at a proximal end of post 443 so that a void space exists between cartridge 420 and tab 445.

Disposed on a proximal face of cartridge head plate 414 is a plurality of bores 418. Each bore 418 extends through cartridge 420, as shown in FIG. 41. Bores 418 are the bores in which plural cannulae 38 are seated within cartridge 420. Disposed within each bore 418 is a polygonal collar 423 that extends circumferentially inwardly from an inner wall of bore 418. In different embodiments of this invention, polygonal collar 423 can be comprised of four, five, six, seven, eight or nine sides.

Manifold 408 is first assembled by attaching valves, which include fittings 432 and heads 430, to the associated distal ends of tubes 428. Tubes 428 and valves are seated within the lower shell 413. Fasteners, not identified, extend through tabs 424 and 426 into complementary bosses 425 and 427, respectively, formed in the housing lower shell 413 to retain tube assembly to shell 413. Upper shell 417 is attached to lower shell 413 using methods not relevant to this invention. Plural empty cannulae 38 are seated within the cartridge 420 as shown in FIG. 47. Cartridge 420, together with empty plural cannulae 38, is then attached to manifold housing 410, as shown in FIG. 44. As a consequence of the attachment of cartridge 420, the cannulae female fittings 69 seat over manifold fittings 432.

In some versions of this invention, manifold 408 is shipped in a state whereby the cartridge 420 is attached to the manifold housing 410 and is a plane that is angled from the plane of the housing 410. When the manifold is in this state, the fittings are not in registration with the boss outlets 439. The manifold valves are, therefore, in the closed state. Manifold 408 is then connected to the mixing system 30 by delivery tube 32. When it is time load the cement into the cannulae, cartridge 420 is rotated downwardly so that the cartridge 420 is horizontal with housing 410, as shown in FIG. 41. This places the cartridge 420 in a constrained position because cartridge tabs 436 abut the inner surfaces of housing plate 440. As cartridge 420 rotates to this orientation, fittings 432 rotate correspondingly. As consequence of this rotation, the lumen of each fitting 432 goes into registration with the bore 439 of the associated boss 429. The valves thus go into an open state and allow for fluid communication with the lumen of the attached cement cannulae 38. The plural cannulae 38 of cartridge 420 are simultaneously filled with cement by the forcing of cement through delivery tube 32 by plunger 288. Bone cement advances through the lumen 431 of tubes 428, through the lumen of fittings 432 and into the cannulae 38.

In order to remove filled cannulae, the cartridge 420 must be pivoted to the angled orientation of FIGS. 44 and 45. When the cartridge is pivoted back, the fittings 432, since they remain engaged with the cannulae, are rotated with the cartridge 420. Owing to this rotation of the fittings, the fitting lumens go out of registration with the associated boss outlet opening 439. In other words, the valves shift to a closed state. Cement is not able to flow out of the fitting 432.

As shown in FIGS. 44 and 45, at this stage in the process, cartridge 420 is attached to manifold housing 410 at approximately 45 degrees relative to the longitudinal axis of a housing inlet opening 422. Consequently, tabs 436 are aligned with associated slots 442 of housing shell 413. This tabs-in-slots arrangement allows the cartridge to slide relative to the housing.

Polygonal collars 423 apply compressive forces that are greater than the compressive force applied by the cannula female fittings 69 against the valve barbs 433. Consequently, the cannulae 38 remain attached to cartridge 420 when it is removed from the housing 410. Plural filled cannulae 38 can now be removed individually from cartridge 420.

Owing to the flat surface of a head plate 414, filled cannulae are able to be placed on a flat table, and oriented as shown in FIG. 47 or 48. Filled cannulae are able to be removed individually from cartridge 420 for use by a user, such as a nurse or staff found in a typical operating room.

Once this first set of cannulae is used, the procedure may require the use of additional filled cannulae. A second set of cannula are then fitted to cartridge 420. At this time, the procedure may not require the cement loading of all the cannulae that can be fitted to the cartridge. To use the manifold of this invention it is not necessary to load a second cannula in each cartridge bore 418. When the partially loaded cartridge is reattached to the housing 410, the female fittings 69 of the attached cannula/cannulae seat over the complementary housing fitting/fittings 432. When the cartridge is again rotated to the fill state the valve/valves to which the cannula/cannulae is/are attached again rotate to the open state.

At this time though there is no connection between the cartridge and the valve/valves associated with the empty cartridge bores 418. Accordingly, the rotation of the cartridge back to the fill state does not result in the transition of these valves back to the open state. Consequently, when the cement is again forced through the manifold housing, the cement only flows out of the valve/valves to which the cannula/cannulae is/are attached. The remaining valves remain closed.

When the cartridge is less than fully loaded with cannulae, the cannulae are often not seated in the cartridge bores so as to be symmetrically arranged around the longitudinal axis through the cartridge. When cannulae that are asymmetrically arranged within the cartridge are filled with cement, an asymmetric pressure is applied to the cartridge. As this pressure is applied, the cartridge begins to flex to one side. As this flexure continues, the tab 445 of middle post 443 abuts a complimentary slot (not identified) located in the housing lower shell. Once the middle post tab 445 abuts the slot of housing lower shell, flexure of the cartridge is limited. Consequently, the middle post 443 prevents the bending of the cannula/cannulae with the associated fitting/fittings 432.

An advantage of this version of the invention is that the valve does not require a biasing member to return the valve to a closed state.

VI. Additional Alternative Embodiments

In another version of the invention, extending from base 119 are four side walls (not identified). Each side wall extends proximally away from the base 119. These side walls extend over the outer surfaces of the manifold housing 44. These side walls cover the components in between the manifold housing 44 and the plate 36. In this version of the invention, the legs 43 are not present. Instead, posts extend from the proximal face of the plate 36. The posts are located inwardly from the side walls. In this version of the invention, the arms 42 are also not present. Instead, disposed in manifold housing 44 is a frame. The frame is moveably mounted in the manifold housing 44. The frame locks against the plate posts. A spring that extends between the frame and the manifold housing 44 latches the frame against the plate posts. A tab is connected to the frame. The tab extends through an opening on the proximal face of the manifold base 45. The tab is manually actuated to overcome the force imposed by the spring. The actuation of the tab moves the frame causing the frame to disengage from the plate posts.

In another alternative embodiment of this invention, a second mixing chamber, mixing blade and plunger that can be incorporated into the mixing and delivery system 30 of this invention is described in Applicant's Assignee's U.S. Pat. No. 7,658,537, issued on Feb. 9, 2010, and is also herein incorporated by reference. In this system 30, a mixer and a piston of this assembly are motor-driven. A motor operatively engages a mixing paddle to mix bone cement components in a mixing chamber. After a predetermined period of mixing has elapsed, the motor automatically actuates a transfer mechanism, which engages the piston to transfer the bone cement from the mixing chamber to a removable attached delivery device. It should be appreciated that the delivery device can be delivery tube 32 of system 30.

Alternative embodiments of this invention can include different sub-assemblies for mixing the bone cement and forcing the cement through the manifold into the cannula or cannulae. In one alternative system, a mixing and delivery gun mixes bone cement-forming components. The gun of this version of the invention includes a housing, a handle, an auger, a plurality of plungers, a plurality of tubes, and a trigger. An epoxy-like cement comprised of a two-part glass ionomer is used as bone cement within this system. Attached to the mixer housing is a first and second tube. Each tube has a distally located outlet opening. A first glass ionomer bone cement component is stored in the first tube. A second glass ionomer bone cement component is stored in the second tube. Disposed within each separate tube is a plunger. When the user actuates, or depresses the mixer trigger for mixing the bone cement, both plungers advance each glass ionomer bone cement component through each respective tube and into an auger. Actuation of the trigger, therefore, simultaneously mixes and delivers bone cement. The cement-forming components flow towards the auger. The auger acts as a mixer. Within the auger, the two bone cement-forming components are mixed together. As the user continues to actuate the mixer trigger, mixed cement travels through the length of the auger and into a removable attached delivery device. One again, it should be appreciated that the delivery device can be delivery tube 32 of system 30.

Still other cement mixing sub-assemblies of this invention may not include any moving paddle or auger-like components that mix the cement. At a minimum, the cement mixing unit of this system includes a chamber in which the bone cement-forming components are mixed and a transfer mechanism for transferring the mixed bone cement into the manifold.

Furthermore, while the manifold of this invention is designed for use with bone cement mixing and delivery systems, its use is not limited to this type of system. The manifold of this invention may be designed for use with a substance, other than bone cement, that is injected into living tissue using a cannula. One example of this substance is an epoxy or resin. The manifold may be used to divert the flow of fluid in other systems which necessitate the simultaneous filling and release of attached plural filling containers. Thus, it is an object of the appended claims to cover all such variations and modifications that come within the true spirit and scope of this invention.

Other alternative embodiments of this invention may be designed to not include a plate 36, or a cartridge, for simultaneously releasing plural attached cannulae. In this version, attached cannulae may be released from the manifold individually once filled with cement or a similar substance capable of being injected into living tissue.

It should likewise be understood that the cannulae be used as part of the system of this invention are not limited to cannulae that essentially consist only of an elongated tube of constant diameter. This invention can be used to fill a cannula that consists of a syringe-like proximal section from which a narrow diameter tube-like section extends distally forward. Only these tube-like distal sections are configured for insertion into a living body. The piston that forces the substance through the cannulae may only travel in the syringe-like proximal section.

In some versions of the invention, the cement or other substance stored in the shell may not require a mixer associated with the delivery device. In some versions of the invention, a mixer, with blades or paddles integral with the delivery device, may not be required.

The system of this invention is not limited to manifolds capable of filling four cannulae. Other versions of the invention may include manifolds capable of filling two, three or five or more cannulae.

What is claimed is:

1. An assembly for loading cannulae with a substance that is injected into living tissue, the assembly including:
    a shell, said shell defining a reservoir in which the substance for injection into living tissue is held, said shell having opposed proximal and distal ends and being open at the distal end;
    a plunger that is moveably mounted to the shell so as to move proximally to distally through the reservoir so as to force the substance out of the distal end of the shell; and
    a manifold attached to said shell, said manifold including:
        a housing, said housing having: an inlet opening for receiving the substance ejected from the distal end of said shell; and a plurality of channels that branch away from the inlet opening so that the substance introduced through the inlet opening simultaneously flows through the channels;
        a plurality of fittings attached to the housing, each fitting configured to removably receive a cannula configured for insertion into a living being and shaped to define a flow path from an associated housing channel into the attached cannula, each said fitting having a valve, each said valve configured to allow or block the flow of the substance into the attached cannula from the fitting, wherein the valve cooperates with the attached cannula so that:
        upon releasing a first cannula from the associated said fitting, said valve shifts to a closed state; and
        upon the fitting of a second cannula to the said fitting to which the first cannula was attached, said valve shifts to an open state; and
        a cartridge, said cartridge configured to releasably hold a plurality of cannulae and configured to be releasably attached to said housing so that: when said cartridge with cannulae is attached to said housing, the cannulae attach to said fittings; and, when said cartridge is released from said housing, the cannulae are released from said fittings so as to cause the said valves associated with said fittings to which the cannulae were attached to shift to the closed state.

2. The assembly of claim 1, wherein:
    each said cannula is configured to displace the associated said valve to move the valve between the closed and open states; and
    said housing and said cartridge are collectively configured so that, to release said cartridge from said housing, said cartridge must be displaced in a manner that results in the displacement of the first cannula attached to a said fitting that results in the first cannula moving said valve associated with said fitting to the closed state and, when said cartridge is reattached to said housing with the second cannula for attachment to the said fitting, said cartridge is displaced in a manner that results in the displacement of the second cannula that moves the said valve to the open state.

3. The assembly of claim 2, wherein, to release and reattach said cartridge to said housing, said cartridge is rotated relative to said housing.

4. The assembly of claim 2, wherein:
    said housing is formed to have at least one groove; and
    said cartridge is configured to have at least one post, said at least one post having a tab, said tab configured to seat within the at least one groove of said housing.

5. The assembly of claim 1, wherein, each said valve is part of the associated fitting and each said fitting is movably mounted to said housing so that the movement of said fitting results in the associated valve moving between the closed and open states.

6. The assembly of claim 5, wherein, each said fitting moves in a rotational manner relative to said housing.

7. The assembly of claim 5, wherein, each said fitting moves in a linear manner relative to said housing.

8. The assembly of claim 1, wherein, each said valve includes a biasing member and said biasing member configured to, in the absence of an attached cannula, move said valve to the closed state.

9. The assembly of claim 1, wherein said assembly further includes:
    a mixer housing, said mixer housing defining a chamber that is separate from the reservoir of said shell, the chamber adapted to receiving components for forming the substance and wherein said mixer housing is connected to said shell so as to define a fluid communication path from the chamber of said mixer housing to the reservoir of said shell; and
    a mixer for mixing the substance-forming components in the chamber of said mixer housing.

10. The assembly of claim 9, further including a piston separate from said plunger that is mounted to said mixer housing and that is positioned to move through the chamber of said housing so as to urge the substance from the chamber to the reservoir of said shell.

11. The assembly of claim 1, wherein said manifold housing is formed with features that facilitate the removable attachment of said shell to said manifold housing so that, when said manifold housing is attached to said shell, a fluid communication path is established between the distal end outlet opening of said shell and the inlet opening of said manifold housing.

12. The assembly of claim 1, wherein:
said shell is configured so that the substance for injection into living tissue that is held in the reservoir is bone cement; and
said plunger is configured so that, when said plunger is moved through the reservoir of said shell, said plunger is able to urge the bone cement out of said shell and into said manifold housing and into any cannulae attached to said fittings.

13. An assembly for loading cannulae with a substance that is injected into living tissue, the assembly including:
a shell, said shell defining a reservoir in which the substance for injection into living tissue is held, said shell having a distal end with an opening;
a plunger that is moveably mounted in the reservoir of said shell so as to move towards the distal opening of said shell so as to force the substance out of the opening;
a manifold attached to said shell, said manifold including:
a housing, said housing having: an inlet opening for receiving the substance discharged from the distal end of said shell; and a plurality of channels that branch away from the inlet opening so that the substance introduced through the inlet opening simultaneously flows through the channels, each channel having an outlet opening;
a plurality of fittings that are moveably mounted to said housing wherein each said fitting is: located adjacent a separate one of the outlet openings of the housing channels; shaped to removably receive a cannula; shaped to have a lumen that extends from an inlet opening to the cannula attached to said fitting; and moveable between a first position in which the lumen inlet opening is not in registration with the outlet opening of the associated channel so that flow from the channel through the fitting is blocked and a second position in which the lumen inlet opening is in registration with the outlet opening of the associated channel so that there can be fluid flow from the bore through the fitting; and
a cartridge, said cartridge configured to releasably hold a plurality of cannulae, said cartridge configured to be releasably attached to said manifold housing so that when said cartridge is attached to said manifold housing, each cannula attached to said cartridge attaches to a separate one of said fittings and wherein said housing and said cartridge are collectively configured that:
to remove said cartridge from said manifold housing, said cartridge and the attached cannulae undergo a movement that cause the cannulae attached to said fittings to move said fittings to the first position; and
to attached said cartridge to said manifold housing, said cartridge and the attached cannulae undergo a movement that cause each cannulae attached to a said fitting to move the said fitting from the first position to the second position.

14. The assembly of claim 13, wherein said fittings are mounted to said manifold housing to move linearly between the first and second positions.

15. The assembly of claim 13, wherein said fittings are mounted to said manifold housing to rotate between the first and second positions.

16. The assembly of claim 13, further including a plurality of biasing members, each said biasing member extending between said manifold housing and one said fitting, each said biasing member positioned to, in the absence of another force, hold the said fitting against which said biasing member is disposed in the first position.

17. The assembly of claim 13, wherein:
said manifold housing further includes, in addition to said plural fittings that are moveably mounted to said housing, a single fitting that is integral with and static relative to said manifold housing and that is fluid communication with the inlet opening of said manifold housing; and
said cartridge is formed with a feature that, when said cartridge is attached to said manifold housing, blocks flow out of the static said fitting.

18. The assembly of claim 13, wherein:
said manifold housing is formed with at least one slot; and
said cartridge is formed with at least one tab and wherein the at least one slot of said manifold housing and said tab of said cartridge are collectively dimensioned so that, to attached said cartridge to said manifold housing, the at least one tab must seat in the at least one slot.

19. The assembly of claim 13, wherein:
said fittings are mounted to said manifold housing to rotate between the first and second positions; and
at least one of said manifold housing or said cartridge is formed with a feature that engages the other of said cartridge or said manifold housing that prevent the removal of said cartridge and the attached cannulae from said manifold housing unless said cartridge is displaced so the movement of said cartridge rotates the attached cannulae from the second position to the first position.

20. The assembly of claim 13, wherein:
said fittings are mounted to said manifold housing to rotate between the first and second positions;
one of said manifold housing or said cartridge is formed with a slot and the other of said cannula or said manifold housing is formed with a tab dimensioned to seat in the slot when the cartridge is attached to said manifold housing and the slot and said tab are collectively shaped so that, when the cannualae are in the second position, the abutment of said tab against a section of said manifold or housing against surfaces that define the slot block the removal of said cartridge and the attached cannulae from said manifold housing.

21. The assembly of claim 13, wherein:
said shell is configured so that the substance for injection into living tissue that is held in the reservoir is bone cement; and
said plunger is configured so that, when said plunger is moved through the reservoir of said shell, said plunger is able to urge the bone cement out of said shell and into said manifold housing and into any cannulae attached to said fittings.

* * * * *